(12) United States Patent
Li et al.

(10) Patent No.: US 9,388,132 B2
(45) Date of Patent: Jul. 12, 2016

(54) ISOBARIC TANDEM MASS TAGS FOR QUANTITATIVE PROTEOMICS AND PEPTIDOMICS

(75) Inventors: Lingjun Li, Madison, WI (US); Feng Xiang, Midland, MI (US); Tyler Greer, Middleton, WI (US); Dustin Frost, Madison, WI (US); Zhidan Liang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 426 days.

(21) Appl. No.: 13/619,164

(22) Filed: Sep. 14, 2012

(65) Prior Publication Data

US 2013/0078728 A1     Mar. 28, 2013

Related U.S. Application Data

(60) Provisional application No. 61/535,108, filed on Sep. 15, 2011.

(51) Int. Cl.
*G01N 37/00*    (2006.01)
*C07D 207/46*   (2006.01)

(52) U.S. Cl.
CPC .................................. *C07D 207/46* (2013.01)

(58) Field of Classification Search
None
See application file for complete search history.

(56) References Cited

U.S. PATENT DOCUMENTS

| | | | |
|---|---|---|---|
| 7,195,751 | B2 | 3/2007 | Pappin et al. |
| 7,355,045 | B2 | 4/2008 | Dey et al. |
| 7,732,378 | B2 | 6/2010 | Thompson et al. |
| 2010/0129842 | A1 | 5/2010 | Pappin et al. |

FOREIGN PATENT DOCUMENTS

| | | |
|---|---|---|
| EP | 2108654 | 10/2009 |
| WO | 2010/008159 | 1/2001 |
| WO | 2004/086050 | 10/2004 |
| WO | 2008/005846 | 1/2008 |
| WO | 2010/104981 | 9/2010 |

OTHER PUBLICATIONS

Applied Biosystems (2004) Applied Biosystems iTRAQ™ Reagents Chemistry Reference Guide.
Albericio et al. (1998) "Use of Onium Salt-Based Coupling Reagents in Peptide Synthesis," J. Org. Chem. 63:9678-9683.

(Continued)

*Primary Examiner* — Robert Xu
(74) *Attorney, Agent, or Firm* — Lathrop & Gage LLP

(57) ABSTRACT

Compositions and methods of tagging peptides and other molecules using novel isobaric tandem mass tagging reagents, including novel N,N-dimethylated amino acid 8-plex and 16-plex isobaric tandem mass tagging reagents. The tagging reagents comprise: a) a reporter group having at least one atom that is optionally isotopically labeled; b) a balancing group, also having at least one atom that is optionally isotopically labeled, and c) an amine reactive group. The tagging reagents disclosed herein serve as attractive alternatives for isobaric tag for relative and absolute quantitation (iTRAQ) and tandem mass tags (TMTs) due to their synthetic simplicity, labeling efficiency and improved fragmentation efficiency.

15 Claims, 27 Drawing Sheets

(56) References Cited

OTHER PUBLICATIONS

Aye et al. (2009) "Selectivity in Enrichment of cAMP-Dependent Protein Kinase Regulatory Subunits Type I and Type II and Their Interactors Using Modified cAMP Affinity Resins," Mol. Cell. Proteomics 8:1016-1028.
Boehm et al. (2007) "Precise Protein Quantification Based on Peptide Quantification Using iTRAQ™," BMC Bioinformatics 8(214):1-18.
Boersema et al. (2008) "Triplex Protein Quantification Based on Stable Isotope Labeling by Peptide Dimethylation Applied to Cell and Tissue Lysates," Proteomics 8:4624-4632.
Boersema et al. (2009) "Multiplex Peptide Stable Isotope Dimethyl Labeling for Quantitative Proteomics," Nature Protocols 4(4):484-494.
Carpino et al. (1995) "Tetramethylfluoroformamidinium Hexafluorophosphate: A Rapid-Acting Peptide Coupling Reagent for Solution and Solid Phase Peptide Synthesis," J. Am. Chem. Soc. 117:5401-5402.
Coste et al. (1994) "Coupling N-Methylated Amino Acids Using PyBroP and PyCloP Halogenophosphonium Salts: Mechanism and Fields of Application," J. Org. Chem. 59:2437-2446.
Dayon et al. (2008) "Relative Quantification of Proteins in Human Cerebrospinal Fluids by MS/MS Using 6-Plex Isobaric Tags," Anal. Chem. 80:2921-2931.
Falb et al. (1999) "In situ Generation of Fmoc-Amino Acid Chlorides Using bis-(trichloro-methyl)carbonate and Its Utilization for Difficult Couplings in Solid-Phase Peptide Synthesis," J. Peptide Res. 53:507-517.
Guo et al. (2007) "Stable-Isotope Dimethylation Labeling Combined with LC-ESI MS for Quantification of Amine-Containing Metabolites in Biological Samples," Anal. Chem. 79:8631-8638.
Guo et al. (2009) "Stereospecific Synthesis of Conformationally Constrained γ-Amino Acids: New Foldamer Building Blocks That Support Helical Secondary Structure," J. Am. Chem. Soc. 131:16018-16020.
Gygi et al. (1999) "Quantitative Analysis of Complex Protein Mixtures Using Isotope-Coded Affinity Tags," Nature Biotechnology 17:994-999.
Hansen et al. (2003) "Mass Spectrometric Analysis of Protein Mixtures at Low Levels Using Cleavable C-Isotope-Coded Affinity Tag and Multidimensional Chromatography," Mol. Cell. Proteomics 2:299-314.
Hsu et al. (2003) "Stable-Isotope Dimethyl Labeling for Quantitative Proteomics," Anal. Chem. 75:6843-6852.
Hsu et al. (2006) "Dimethyl Multiplexed Labeling Combined with Microcolumn Separation and MS Analysis for Time Course Study in Proteomics," Electrophoresis 27:3652-3660.
Huang et al. (2006) "Quantitation of Protein Phosphorylation in Pregnant Rat Uteri Using Stable Isotope Dimethyl Labeling Coupled with IMAC," Proteomics 6:1722-1734.
Ji et al. (2005) "Quantitative Proteome Analysis Using Differential Stable Isotopic Labeling and Microbore LC-MALDI MS and MS/MS," J. Proteome Research 4:734-742.
Ji et al. (2005) "Identification and Quantification of Differentially Expressed Proteins in E-Cadherin Deficient SCC9 Cells and SCC9 Transfectants Expressing E-Cadherin by Dimethyl Isotope Labeling, LC-MALDI MS and MS/MS," J. Proteome Research 4:1419-1426.
Ji et al. (2005) "Differential Dimethyl Labeling of N-Termini of Peptides After Guanidination for Proteome Analysis," J. Proteome Research 4:2099-2108.
Ji et al. (2006) "Effect of 2MEGA Labeling on Membrane Proteome Analysis Using LC-ESI QTOF MS," J. Proteome Research 5:2567-2576.
Ji et al. (2007) "A Study of Reproducibility of Guanidination—Dimethylation Labeling and Liquid Chromatography Matrix-Assisted Laser Desorption Ionization Mass Spectrometry for Relative Proteome Quantification," Anal. Chim. Acta 585:219-226.
Khidekel et al. (2007) "Probing the Dynamics of O-GlcNAc Glycosylation in the Brain Using Quantitative Proteomics," Nat. Chem. Biol. 3(6):339-348.
Lemeer et al. (2008) "Comparative Phosphoproteomics of Zebrafish Fyn/Yes Morpholino Knockdown Embryos," Mol. Cell. Proteomics 7:2176-2187.
Li et al. (2003) "Protein Profiling with Cleavable Isotope-Coded Affinity Tag (cICAT) Reagents," Mol. Cell. Proteomics 2:1198-1204.
Merrifield, R.B. (1963) "Solid Phase Peptide Synthesis. I. The Synthesis of a Tetrapeptide," J. Am. Chem. Soc. 85:2149-2154.
Morano et al. (2008) "Multiple Isotopic Labels for Quantitative Mass Spectrometry," Anal. Chem. 80:9298-9309.
Ong et al. (2002) "Stable Isotope Labeling by Amino Acids in Cell Culture, SILAC, as a Simple and Accurate Approach to Expression Proteomics," Mol. Cell. Proteomics 1:376-386.
Ong et al. (2005) "Mass Spectrometry-Based Proteomics Turns Quantitative," Nat. Chem. Biol. 1(5):252-262.
Ow et al. (2009) "iTRAQ Underestimation in Simple and Complex Mixtures: 'The Good, the Bad and the Ugly'," J. Proteome Research 8:5347-5355.
Raijmakers et al. (2008) "Automated Online Sequential Isotope Labeling for Protein Quantitation Applied to Proteasome Tissue-Specific Diversity," Mol. Cell. Proteomics 7:1755-1762.
Rogers et al. (2007) "The Dynamic Phagosomal Proteome and the Contribution of the Endoplasmic Reticulum," Proc. Natl. Acad. Sci. USA 104(47):18520-18525.
Ross et al. (2004) "Multiplexed Protein Quantitation in *Saccharomyces cerevisiae* Using Amine-Reactive Isobaric Tagging Reagents," Mol. Cell. Proteomics 3:1154-1169.
Synowsky et al. (2009) "Comparative Multiplexed Mass Spectrometric Analyses of Endogenously Expressed Yeast Nuclear and Cytoplasmic Exosomes," J. Mol. Biol. 385:1300-1313.
Thompson et al. (2003) "Tandem Mass Tags: A Novel Quantification Strategy for Comparative Analysis of Complex Protein Mixtures by MS/MS," Anal. Chem. 75:1895-1904.
Wang et al. (2009) "Targeted Quantitative Mass Spectrometric Identification of Differentially Expressed Proteins between Bax-Expressing and Deficient Colorectal Carcinoma Cells," J. Proteome Research 8:3403-3414.
Xiang et al. (2010) "N,N-Dimethyl Leucines as Novel Isobaric Tandem Mass Tags for Quantitative Proteomics and Peptidomics," Anal. Chem. 82:2817-2825.
Xiang et al. (Jun. 1-5, 2008) "N, N-Dimethyl Amino Acids as iTRAQ Reagent for Improved Peptdiomics and Proteomics," Proceedings of the 56th ASMS Conference on Mass Spectrometry and Allied Topics, Denver, CO.
Xiang et al. (May 31-Jun. 4, 2009) "Generating Neuropeptide Standard Curve in a Single LC-MS Run by N, N-Dimethyl Amino Acids Tandem Mass Tags," Proceedings of the 57th ASMS Conference on Mass Spectrometry and Allied Topics>.
Xiang et al. (Mar. 8-13, 2009) "Amino Acid iTRAQ Reagents," Pittcon Conference Presentation, Chicago, IL.
Xiang et al. (Mar. 24, 2010) "N, N-Dimethyl Leucines as Novel Isobaric Tandem Mass Tags for Quantitative Proteomics and Peptidomics," WARF departmental presentation, Madison, WI.
Xiang, Feng (Feb. 11, 2011) WARF departmental presentation, Madison, WI.
Zeng et al. (2009) "Revival of Deuterium-Labeled Reagents for Protein Quantitation," Chem. Commun. pp. 3369-3371.
Zhang et al. (2002) "Controlling Deuterium Isotope Effects in Comparative Proteomics," Anal. Chem. 74:3662-3669.
Zhang et al. (2010) "Deuterium Isobaric Amine-Reactive Tags for Quantitative Proteomics," Anal. Chem. 82(18):7588-7595.

| Residue | 3-letter code | 1-letter code | Immonium ion* | Related ions* |
|---|---|---|---|---|
| Alanine | Ala | A | 44 | |
| Arginine | Arg | R | 129 | 59,70,73,87,100,112 |
| Asparagine | Asn | N | 87 | 70 |
| Aspartic acid | Asp | D | 88 | 70 |
| Cysteine | Cys | C | 76 | |
| Glutamic acid | Glu | E | 102 | |
| Glutamine | Gln | Q | 101 | 56,84,129 |
| Glycine | Gly | G | 30 | |
| Histidine | His | H | 110 | 82,121,123,138,166 |
| Isoleucine | Ile | I | 86 | 44,72 |
| Leucine | Leu | L | 86 | 44,72 |
| Lysine | Lys | K | 101 | 70,84,112,129 |
| Methionine | Met | M | 104 | 61 |
| Phenylalanine | Phe | F | 120 | 91 |
| Proline | Pro | P | 70 | |
| Serine | Ser | S | 60 | |
| Threonine | Thr | T | 74 | |
| Tryptophan | Trp | W | 159 | 77,117,130,132,170,171 |
| Tyrosine | Tyr | Y | 136 | 91,107 |
| Valine | Val | V | 72 | 41,55,69 |

FIGURE 3

Dimethylated Leucine

Dimethylated Glycine

Dimethylated Alanine

Dimethylated Valine

Dimethylated Isoleucine

Dimethylated Phenylalanine

Dimethylated Leu-Ala
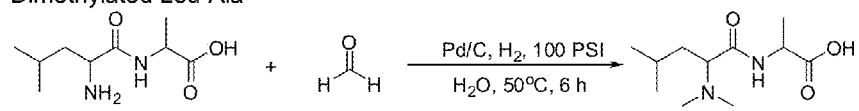
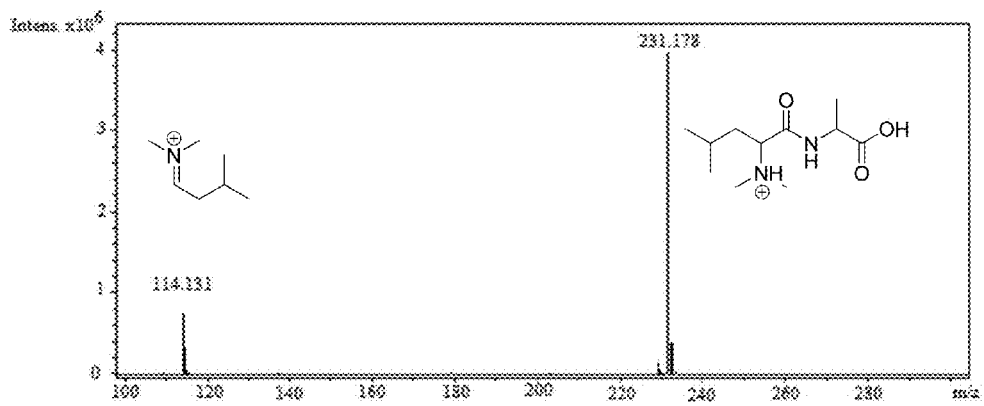
FIGURE 17a
Dimethylated Leu-Gly
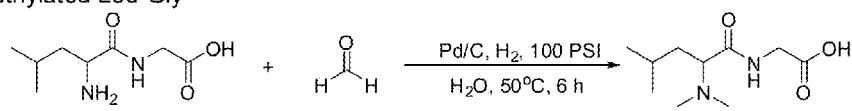
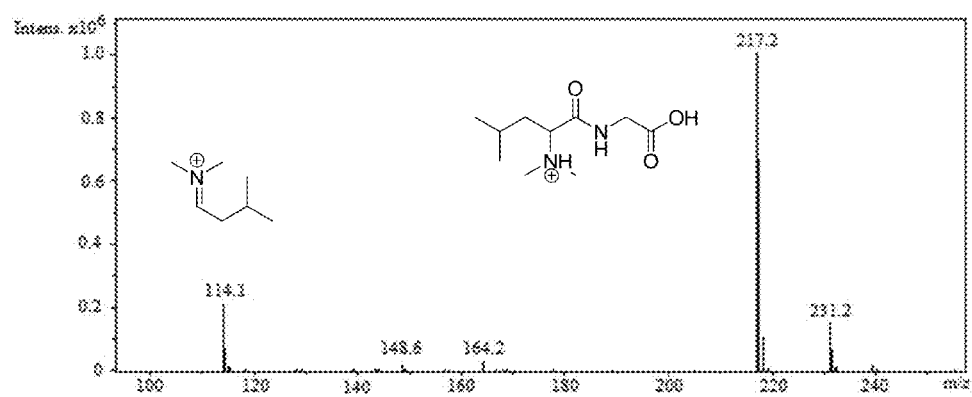
FIGURE 17b Dimethylated Ala-Leu Dimethylated Norleucine-Ala and Dimethylated Norvaline-Ala Dimethylated Leu- 2-Aminobutylric Acid and Dimethylated Leu- 3-Aminobutylric Acid Dimethylated Leu- 3-Aminobutylric Acid

ISOBARIC TANDEM MASS TAGS FOR QUANTITATIVE PROTEOMICS AND PEPTIDOMICS

CROSS-REFERENCE TO RELATED APPLICATION

This application claims priority from U.S. Provisional Patent Application No. 61/535,108 filed Sep. 15, 2011, which is incorporated by reference herein to the extent that there is no inconsistency with the present disclosure.

STATEMENT REGARDING FEDERALLY SPONSORED RESEARCH OR DEVELOPMENT

This invention was made with government support under DK071801 awarded by the National Institutes of Health. The government has certain rights in the invention.

BACKGROUND OF THE INVENTION

It has become increasingly important to determine the relative abundance of protein or endogenous peptide expression levels in different biological states using mass spectrometry (MS). MS is a technique growing in popularity in proteomics due, in part, to its ability to detect the presence of various chemical moieties such as metabolites, proteins, and nucleic acids. MS can provide both qualitative and quantitative information about the molecule provided that a proper internal standard or marker is used.

Numerous MS-based chemical derivatization quantitation approaches such as mass-difference labeling and isobaric labeling methodologies have been developed and widely used for quantitative proteomics and peptidomics (Ong et al., Nat. Chem. Biol. 2005, 1:252-262). Mass-difference labeling approaches introduce a mass difference for the same peptide by incorporating a light or heavy isotopic form of the labeling reagent. Light and heavy labeled peptides are combined prior to MS analysis, and quantitation is accomplished by comparing the extracted ion chromatogram peak areas of light and heavy forms of the same peptide. Methods such as isotope-coded affinity tags (ICAT), stable isotope labeling with amino acids in cell culture (SILAC), 4-trimethylammonium-butyryl (TMAB) labels, and reductive formaldehyde dimethylation have been widely used in mass-difference quantitation proteomics (Gygi et al., Nat. Biotechnol. 1999, 17:994; Li et al., Mol. Cell. Proteomics 2003, 2:1198-1204; Hansen et al., Mol. Cell. Proteomics 2003, 2:299-314; Ong et al., Mol. Cell. Proteomics 2002, 1:376-386; Zhang et al., Anal. Chem. 2002, 74:3662-3669; and Hsu et al., Anal. Chem. 2003, 75:6843-6852).

Although being well-established methodologies for quantitative proteomics, mass-difference labeling has two general limitations. First, only a binary set of samples can be compared due to the use of light and heavy labeling of a peptide. Second, mass-difference labeling increases mass spectral complexity by introducing an extra pair of labeled peptides, thus decreasing the confidence and accuracy of quantitation. The first limitation has been addressed and overcome by several research groups by introducing multiple heavy labeled reagents, rather than just one (Hsu et al., Electrophoresis 2006, 27:3652-3660; Morano et al., Anal. Chem. 2008, 80:9298-9309; and Boersema et al., Proteomics 2008, 8:4624-4632). However, the second limitation is an inherent drawback of the mass-difference approach, and the spectral complexity is only increased with the use of multiple heavy isotope labeling reagents.

These limitations can be addressed through the use of isobaric labeling. There are two popular brands of isotopic labeling reagents, iTRAQ and TMT, currently sold in order to tag peptides when performing quantitative analysis of peptides using MS. Tandem mass tags (TMTs) were the first isobaric labeling reagents used to improve the accuracy for peptide and protein quantitation by simultaneous identification and relative quantitation during tandem mass spectrometry (MS/MS or $MS^2$) experiments (Thompson et al., Anal. Chem. 2003, 75:1895-1904). Two generations of TMTs were reported (TMT1 and TMT2), and each generation had two isobaric labels. Amine groups (N-terminus and E-amino group of the lysine side chain) in peptides labeled with TMT1 produce fragments at m/z 270 and 273 at 70 V collision energy, whereas TMT2 produces fragments at m/z 287 and 290 at 35 V collision energy. Relative quantitation can be performed by comparing the intensities of these fragments to one another. A 6-plex version of TMTs was also recently reported (Dayon et al., Anal. Chem. 2008, 80:2921-2931).

iTRAQ follows the same principle as TMTs quantitation, but it improves the quantitation further by providing four isobaric labels with signature reporter ions that are one Da apart upon $MS^2$ fragmentation (Ross et al., Mol. Cell. Proteomics 2004, 3:1154-1169). Thus, iTRAQ allows for the quantitation of proteins present in four different biological states simultaneously (a 4-plex quantitation). These tags are structurally identical isobaric compounds with different isotopic combinations. Each sample is labeled individually, pooled together, and introduced into the mass spectrometer for quantitative analysis. Since samples are isobarically labeled, the same peptide from four samples produces a single peak in MS mode, but upon $MS^2$ fragmentation, each labeled sample gives rise to a unique reporter ion (m/z 114.1, 115.1, 116.1, and 117.1) along with sequence-specific backbone cleavage for identification. Relative quantitation is achieved by correlating the relative abundance of each reporter ion with its originating sample.

iTRAQ 8-plex quantitation follows the same quantitation principle as iTRAQ 4-plex quantitation (C. Leila, et al., Proteomics 2007, 7. 3651-3660). Instead of using four reporter ions (m/z 114.1, 115.1, 116.1, and 117.1) for quantitation of four samples, eight reporter ions (m/z 114.1, 115.1, 116.1, 117.1, 118.1, 119.1, 121.1 and 122.1) can be produced and used for simultaneous quantitation of eight samples. iTRAQ 8-plex reagents double the quantitation throughput over the 4-plex reagents. In addition to the higher throughput over a wider quantitation dynamic range, 8-plex reagents can also provide more accurate quantitation.

A common problem with the 4-plex iTRAQ reagent is that because the four reporter ions are only one Dalton apart, isotope peak gains from or losses to adjacent reporter ions affect both the accuracy and dynamic range of quantitation for 4-plex samples. The quantitation accuracy problem can be overcome by employing a complicated mathematic algorithm to quantify the reporter ions (A. Boehm, et al., BMC Bioinformatics 2007, 8. 214). A software package is needed for 4-plex quantitation which brings extra cost for data analysis. The mathematic approach works well for quantifying samples within ten-fold ratio difference. However, if two samples labeled by two adjacent reporter ions have abundance difference greater than ten-fold, the reporter ion representing lower concentration sample could potentially be buried by the isotope peak of the adjacent reporter ion representing high concentration sample (S. Y. Ow, et al., J. Proteome Res. 2009, 8. 5347-5355). Therefore, the quantitation dynamic range is reduced. Two adjacent reporter ions with one Dalton mass difference should be avoided to quantify samples varying in concentration greater than ten-fold. In this situation, 4-plex reagents can only be used to quantify two samples. 8-plex reagents can provide two Dalton mass difference reporter ions for quantitation of four samples. Because of the minimal interference of adjacent reporter ions, accurate quantitation and wider quantitation dynamic range can be achieved for four samples without sophisticated mathematical processing. Demand of high throughput protein/peptide LC/MS/MS quantitation in practice makes iTRAQ 8-plex highly desirable for multiple sample quantitation. However, the trade-off of accurate quantitation and wider dynamic range is the high price of iTRAQ 8-plex reagents (about $2,500 for a kit for five trials).

Isobaric $MS^2$ tagging approaches have also been successfully used in MS-based quantitative proteomics. However, their application as a routine tool for quantitative MS studies is limited by high cost. The high cost of commercial TMTs and iTRAQ comes from the challenge of synthesizing these compounds as multiple steps involved in the synthesis lead to moderate to low yields. A set of 6-plex deuterium-labeled DiART reagents was reported very recently with reduced cost of isobaric labeling. However, seven steps were still required to synthesize these compounds with only 30%-40% overall yield (Zeng et al., Chem. Commun. 2009, 3369-3371). Additionally, many alternate MS labels are too labile which leads to cleaving the tag from the peptide of interest during mass spectrometry analysis.

A new type of isobaric $MS^2$ tags with fewer steps involved in synthesis is desirable to further reduce experimental cost while taking full technical advantages of the isobaric $MS^2$ tagging approach. Formaldehyde dimethylation represents one of the most affordable approaches among all isotopic chemical derivatization techniques used for MS-based peptide and protein quantitation (Boersema et al., Proteomics 2008, 8:4624-4632; Ji et al., Proteome Res. 2005, 4:2099-2108; Ji et al., Proteome Res. 2005, 4:1419-1426; Ji et al., Proteome Res. 2005, 4:734-742; Huang et al., Proteomics 2006, 6:1722-1734; Ji et al., Proteome Res. 2006, 5:2567-2576; Ji et al., Anal. Chim. Acta 2007, 585:219-226; Guo et al., Anal. Chem. 2007, 79:8631-8638; Wang et al., J. Proteome Res. 2009, 8:3403-3414; Raijmakers et al., Mol. Cell. Proteomics 2008, 7:1755-1762; Synowsky et al., J. Mol. Biol. 2009, 385:1300-1313; Lemeer et al., Mol. Cell. Proteomics 2008, 7:2176-2187; Khidekel et al., Nat. Chem. Biol. 2007, 3:339-348; Rogers et al., Proc. Natl. Acad. Sci. U.S.A. 2007, 104:18520-18525; Aye et al., Mol. Cell. Proteomics 2009, 8:1016-1028; and Boersema et al., Nat. Protocols 2009, 4:484-494). However, isotopic formaldehyde labeling is a mass-difference labeling approach and, thus, lacks the advantages offered by the isobaric labeling approach.

The present inventors previously developed and demonstrated a set of novel and cost effective N,N-dimethylated leucine (DiLeu) 4-plex reagents as an attractive alternative to iTRAQ reagent for protein and peptide quantitation (F. Xiang, et al., Anal. Chem. 2010, 82. 2817-2825). However, there is no alternative to 8-plex iTRAQ reagents currently on the market. Therefore, what is needed are improved isobaric tandem MS tags that are simple to synthesize, highly efficient in labeling small molecules and peptides, more stable than the current commercial labeling reagents, and are significantly easier and less expensive to produce. Developing a set of novel 8-plex, or even 16-plex, reagents with greatly reduced experimental cost would be beneficial for increasing the throughput of multiple sample quantitation and achieving accurate quantitation of multiple samples in a routine manner.

SUMMARY OF THE INVENTION

The present invention provides improved compositions and methods of labeling peptides and other molecules using novel isobaric tandem mass spectrometry ($MS^2$) tagging reagents with high quantitation efficacy and greatly reduced cost for peptidomics, proteomics quantitation, and small molecule quantification. In particular, the present invention provides the design and synthesis of a set of novel N, N-dimethylated amino acid based isobaric 8-plex reagents as well as 16-plex reagents. Preliminary data of synthesis and peptide labeling is also presented.

The tagging reagents of the present invention comprise: a) a reporter group, having at least one atom that is optionally isotopically labeled; b) a balancing group, also having at least one atom that is optionally isotopically labeled, and c) an amine reactive group able to react with an amine group of the molecule to be tagged, such as the N-terminus and/or an ϵ-amino group of a lysine side chain of a peptide. The limiting factor of previous isobaric tagging reagents is the number of atoms able to be isotopically labeled in the balancing group. For example, the previously reported dimethylated leucine (DiLeu) 4-plex reagents utilize isotopic carbonyl groups, which only contain two atoms. As a result, only four isotopic combinations can be achieved within the balancing group. The isobaric tagging reagents of the present invention have balancing groups able to provide a greater number of isotopic combinations. As a result, the present invention provides compositions and methods of tagging peptides and other molecules using 8-plex and 16-plex isobaric tandem mass tagging reagents, including novel N,N-dimethylated amino acid based 8-plex and 16-plex tagging reagents.

In one embodiment, multiple tagging reagents are used to label two or more peptide or small molecule samples, or a mixture of peptides or small molecules wherein the tagging reagents have the same molecular weight as one another, but wherein the reporter group of each tagging reagent has a different mass due to the different isotopically labeled atoms in each reporter group. Similarly, the balancing group of each tagging reagent has a different mass from one another due to the different isotopically labeled atoms in each balancing group. In one embodiment, each peptide or small molecule sample is labeled individually, pooled together, and introduced into the mass spectrometer for quantitative analysis. Since the tagging reagents have the same mass, the labeled peptides or small molecules will produce a single peak in MS mode, but upon $MS^2$ fragmentation, each sample labeled with a different tagging reagent will produce a unique reporter ion due to the mass difference between the reporter groups. Preferably, a peptide or small molecule labeled with a tagging reagent of the present invention is able to form a strong immonium ion during $MS^2$ fragmentation. The peptides labeled using the compounds described herein may be enzyme digested peptides. The tagging reagents of the present invention can be used to label and quantify molecules other than peptides provided that the molecule contains an amine group able to react with the amine reactive group of the tagging reagent. Small molecules able to be effectively labeled using the tagging reagents of the present invention include, but are not limited to, amine-containing neurotransmitters and metabolites.

In one embodiment, the tagging reagents of the present invention are derived from a dipeptide comprising two amino acids. Preferably the amino acids are natural amino acids, but the present invention contemplates the use of unnatural, non-standard and synthetic amino acids, such as β amino acids, as the amino acid which makes up the reporter group, the balancing group, or both. In a further embodiment, the tagging reagents of the present invention are derived from a dipeptide where the amino group of one amino acid has been dimethylated. The free carboxyl group of the dipeptide can be attached to an amine reactive group or a target molecule, such as a peptide. During MS² fragmentation, the dipeptide will fragment to form a reporter ion, preferably an immonium ion, which can be readily detected. In a further embodiment, the tagging reagents are derived from N,N-dimethyl leucine (DiLeu); N,N-dimethyl isoleucine (Di Ile); N,N-dimethyl alanine (DiAla); N,N-dimethyl glycine (DiGly); N,N-dimethyl valine (DiVal); N,N-dimethyl histidine (DiHis); N,N-dimethyl phenylalanine (DiPhe); N,N-dimethyl tryptophan (DiTrp); N,N-dimethyl lysine (DiLys) or N,N-dimethyl tyrosine (DiTyr).

As an example, a series of isobaric tagging reagents may comprise a reporter group (which forms the reporter ion during fragmentation), a balance group, and an amine reactive group as shown below in Scheme 1 (using N,N-dimethyl leucine and alanine as the amino acids). One or more atoms in the reporter group, balancing group, or both, in each reagent are the isotopically heavy versions of the atom. Each tagging reagent in the series will have a different combination of atoms that are the isotopically heavy versions of the atoms, but with the condition that the total aggregate mass of each tagging reagent is the same as the other tagging reagents in the series. For example, the nitrogen atom in the reporter group shown in Scheme 1 may be $^{15}$N, one or more carbon atoms may be $^{13}$C, and one or more hydrogen atoms may be deuterium (D). This provides at least eight possible reporter groups each having a different mass, including one reporter group containing no heavy isotopes. The balancing groups of each reagent will contain the appropriate number of heavy isotopes, such as $^{18}$O, $^{13}$C, $^{15}$N or D, so that the combined mass of the balancing group and reporter group are the same for each reagent. Varying the atoms which contain the heavy isotope form in the reporter groups and balancing groups allows each tagging reagent to have the same combined mass but a different mass of the reporter group after fragmentation.

such as a peptide. The samples may then be combined together or with a known standard labeled with one of the tagging reagents. The combined sample is then analyzed using mass spectrometry. After fragmentation, the reporter group for each tagged peptide or molecule will present a different mass due to the differently isotopically labeled atoms. By comparing the relative signal strength of the detected reporter groups during tandem mass spectrometry, the amounts of each tagged molecule can be quantified, especially if a known standard is used as one of the tagged molecules.

In one embodiment, the tagging reagents (absent the amine reactive group) preferably have a molecular mass between approximately 125 and 400 Daltons, preferably between approximately 150 and 350 Daltons, even more preferably between approximately 180 and 250 Daltons. This allows the reporter group to have a large enough mass to be readily detected during mass spectrometry analysis, while larger tagging reagents may result in inefficient synthesis and labeling due to steric hindrance.

Fragmentation may be achieved using a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. The molecule fragments are then detected, identified and optionally quantified using methods as known in the art.

Methods of Analyzing a Mixture Using 8-plex or 16-plex Tagging Reagents

In one embodiment, the present invention provides a method of analyzing a molecule having an amine group comprising the steps of: a) providing the molecule; b) labeling the molecule with a compound having the formula of:

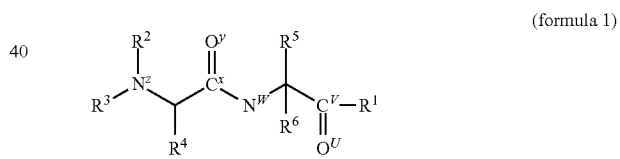

(formula 1)

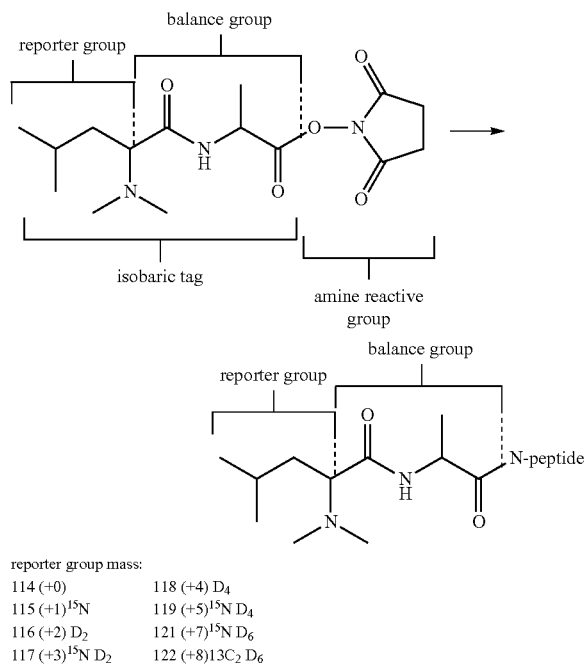

wherein
R¹ is an amine reactive group;
R² and R³, independently of one another, are CH₃, $^{13}$CH₃, CDH₂, $^{13}$CDH₂, CD₂H, $^{13}$CD₂H, CD₃ or $^{13}$CD₃;
R⁴ and R⁵, independently of one another, are selected from the group consisting of hydrogen, deuterium, branched and unbranched C₁ to C₁₂ alkyl groups, C₁ to C₁₂ cycloalkyl groups, C₁ to C₁₂ alkenyl groups, C₁ to C₁₂ cycloalkenyl groups, C₄ to C₁₂ aryl groups and C₄ to C₁₂ arylalkyl groups, wherein each of R⁴ and R⁵ optionally contain one or more $^{13}$C atoms and one or more deuterium atoms;
R⁶ is hydrogen or deuterium;
C$^V$ and C$^x$, independently of one another, are $^{12}$C or $^{13}$C, O$^U$ and O$^y$, independently of one another, are $^{16}$O or $^{18}$O; and
N$^z$ and N$^W$, independently of one another, are $^{14}$N or $^{15}$N, and
wherein at least one of R² or R³ contains a deuterium atom, N$^z$ is $^{15}$N, or N$^W$ is $^{15}$N,
c) fragmenting the labeled molecule to generate an immonium ion from the labeled molecule; and d) detecting and analyzing fragments of the labeled molecule. Label- The tagging reagents are reacted with one or more samples containing a molecule of interest containing an amine group, ing the molecule comprises the step of reacting the amine reactive group of the tagging reagent with the amine group of the molecule. In one embodiment, the molecule is a peptide, metabolite or neurotransmitter. Where the molecule is a peptide, labeling the peptide comprises the step of reacting the amine reactive group of the tagging reagent with the N-terminus of the peptide and/or reacting the amine reactive group of the tagging reagent with an E-amino group within peptide. In one embodiment, the peptide is an enzyme digested peptide. In one embodiment, the labeled peptide has the formula:

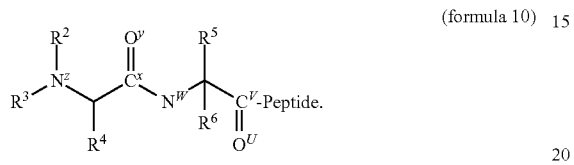

(formula 10)

Preferably, $R^4$ and $R^5$ are selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^4$ and $R^5$ are selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

In one embodiment, the compound comprises an amine reactive group covalently bound to a carboxyl group of a first amino acid, wherein the first amino acid also forms a peptide bond with a dimethylated amino acid. In a further embodiment, the compound has the formula:

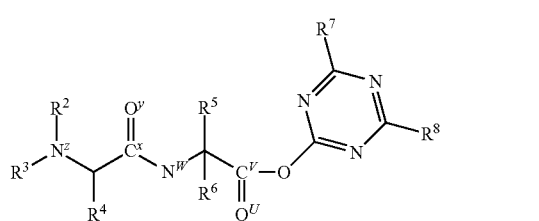

(formula 2)

wherein $R^7$ and $R^8$ are branched and unbranched $C_1$ to $C_{12}$ alkyl groups, preferably branched and unbranched $C_1$ to $C_3$ alkyl groups.

In a further embodiment, the compound has the formula:

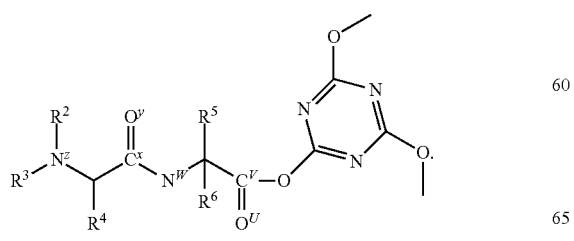

(formula 3)

In a further embodiment, the compound has the formula:

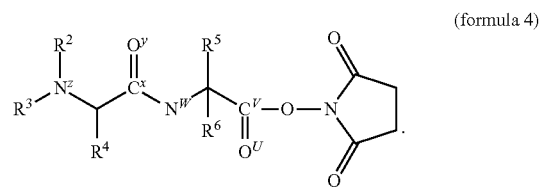

(formula 4)

In a further embodiment, the compound has the formula:

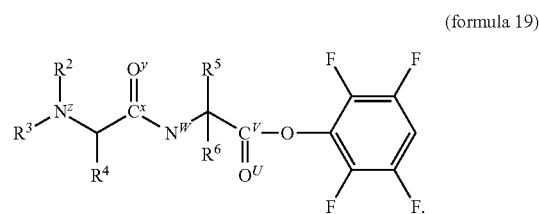

(formula 19)

In one embodiment, the compound has the formula:

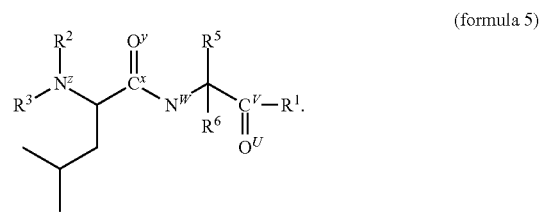

(formula 5)

In a further embodiment, $R^5$ is a methyl group optionally containing one or more deuterium atoms and wherein the carbon is $^{12}C$ or $^{13}C$; $R^5$ is hydrogen or deuterium; or $R^5$ is an isopropyl group optionally containing one or more deuterium atoms and one or more $^{13}C$ atoms.

In a further embodiment, the compound is selected from:

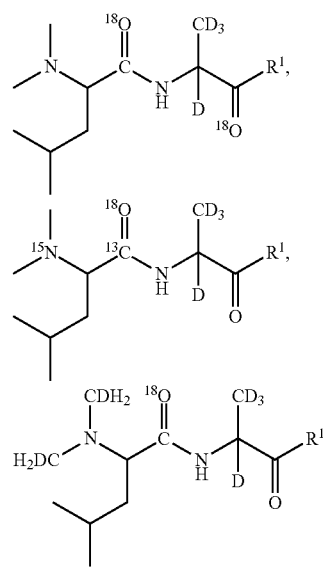

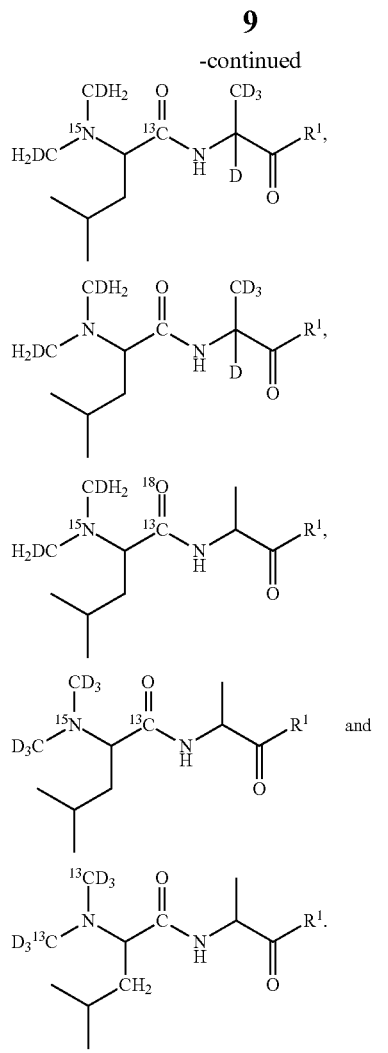
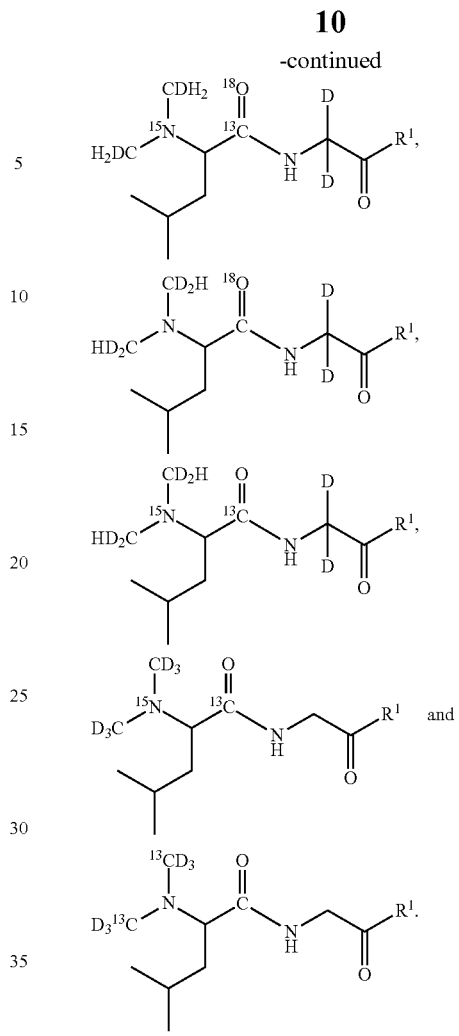
In a further embodiment, the compound is selected from:
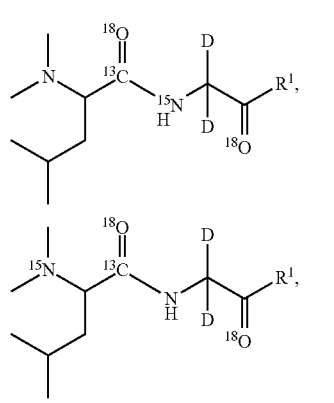
In a further embodiment, the compound is selected from:
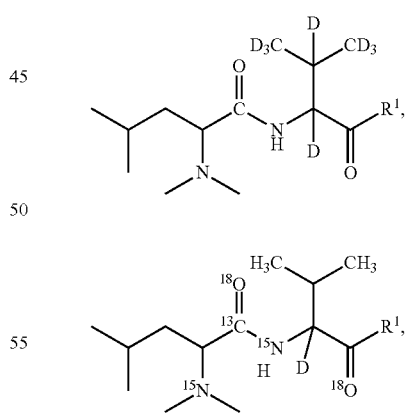
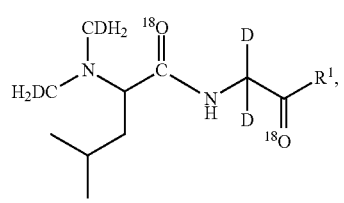
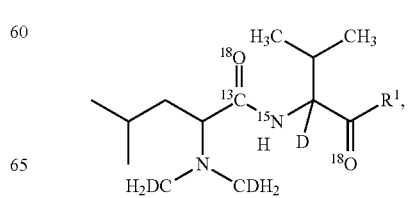

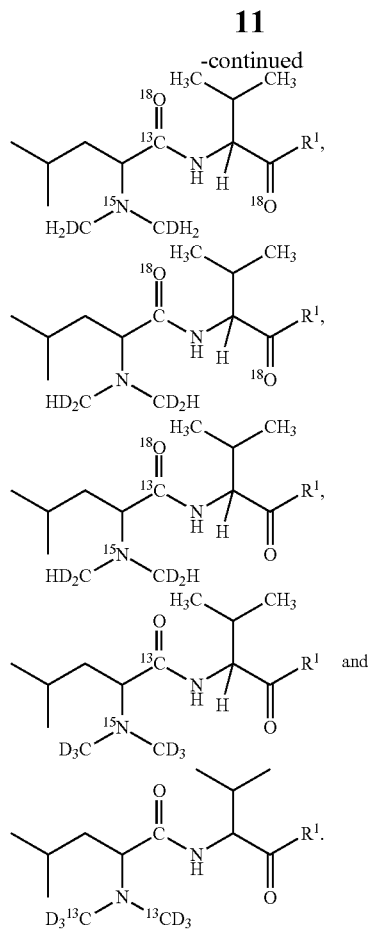

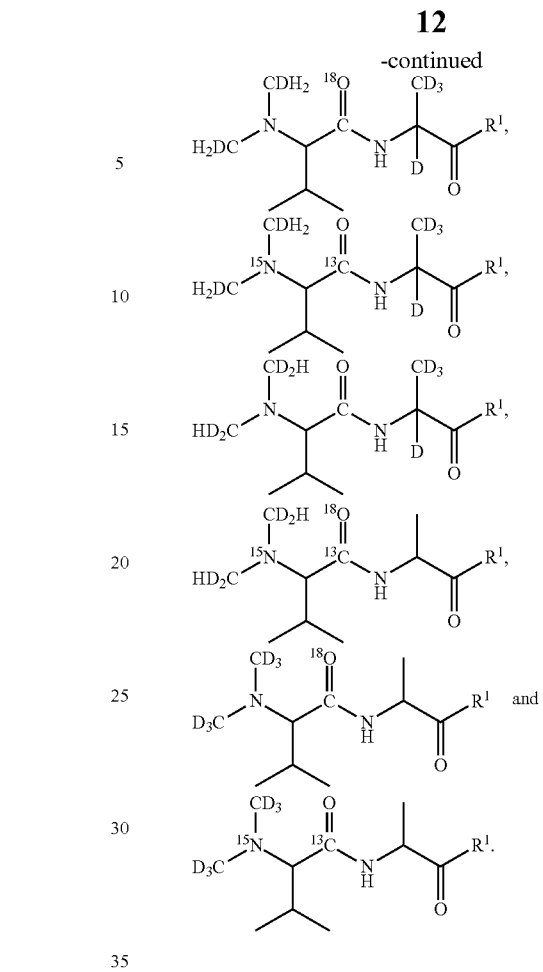

In one embodiment, the compound has the formula:

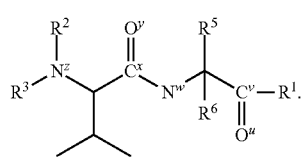
(formula 6)

In a further embodiment, R⁵ is a methyl group optionally containing one or more deuterium atoms and wherein the carbon is $^{12}C$ or $^{13}C$; R⁵ is hydrogen or deuterium; or R⁵ is a butyl group optionally containing one or more deuterium atoms and one or more $^{13}C$ atoms.

In a further embodiment, the compound is selected from:

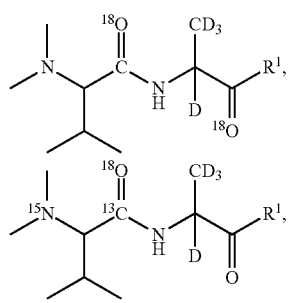

In a further embodiment, the compound is selected from:

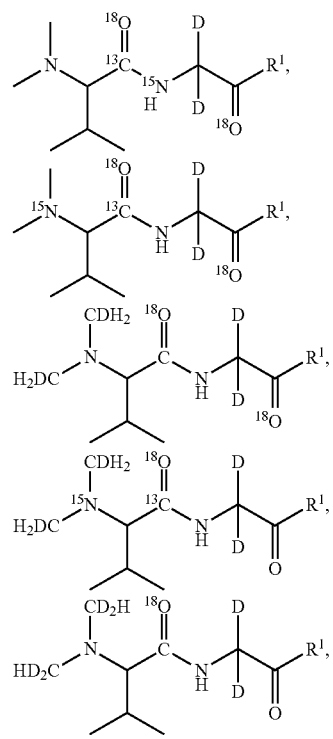

13
-continued
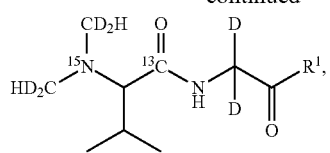
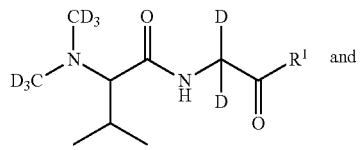 and
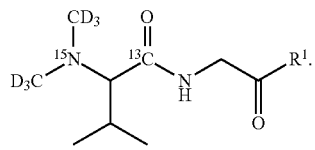
In a further embodiment, the compound is selected from:
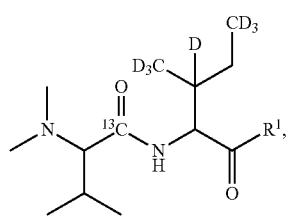
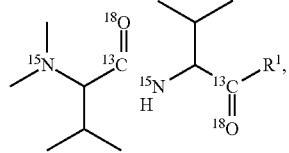
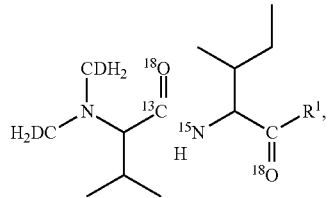
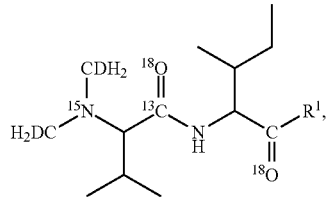
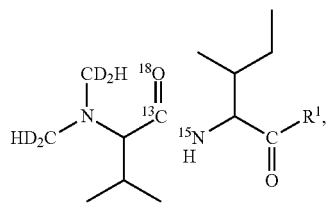
14
-continued
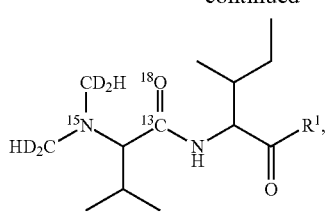
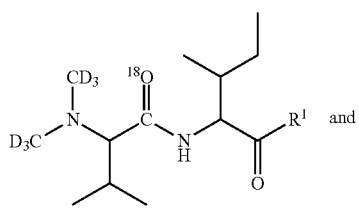 and
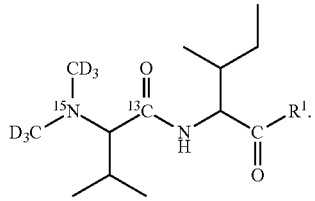
In a further embodiment, the compound is selected from:
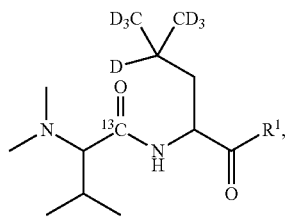
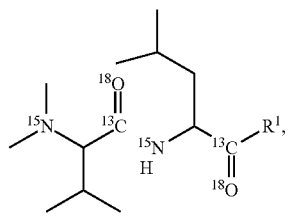
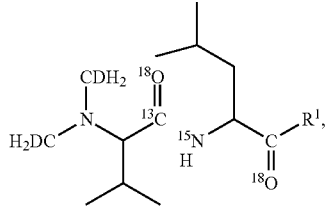
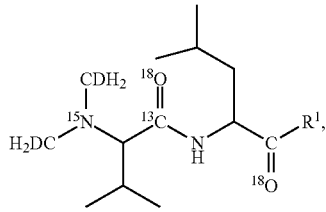

-continued

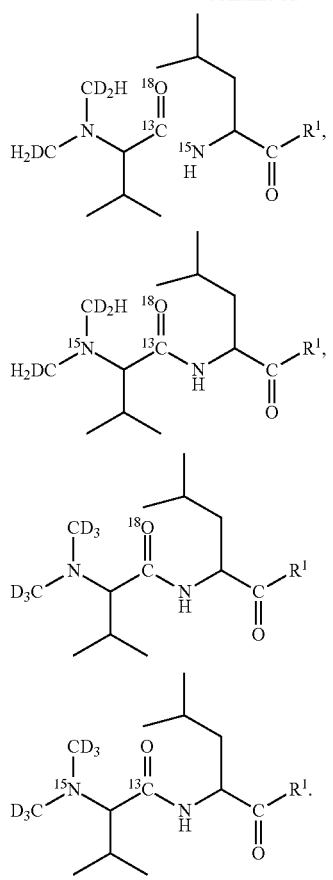

In one embodiment, the compound has the formula:

$$R^3\underset{R^2}{\overset{}{N^z}}\overset{R^2}{\underset{}{\phantom{N}}}\overset{O^y}{\underset{}{C^x}}\overset{}{\underset{R^6}{\overset{R^5}{\underset{}{\phantom{N}}}}}\overset{}{\underset{O^u}{\overset{}{C^v}}}-R^1.$$ (formula 7)

In a further embodiment, $R^5$ is a methyl group optionally containing one or more deuterium atoms and wherein the carbon is $^{12}C$ or $^{13}C$; $R^5$ is an isopropyl group optionally containing one or more deuterium atoms and one or more $^{13}C$ atoms; or $R^5$ is a butyl group optionally containing one or more deuterium atoms and one or more $^{13}C$ atoms.

In a further embodiment, the compound is selected from:

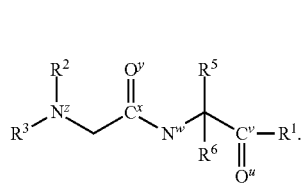

-continued

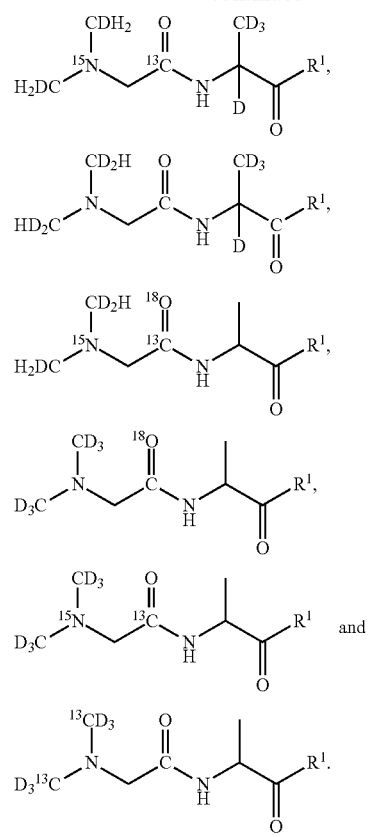

In a further embodiment, the compound is selected from:

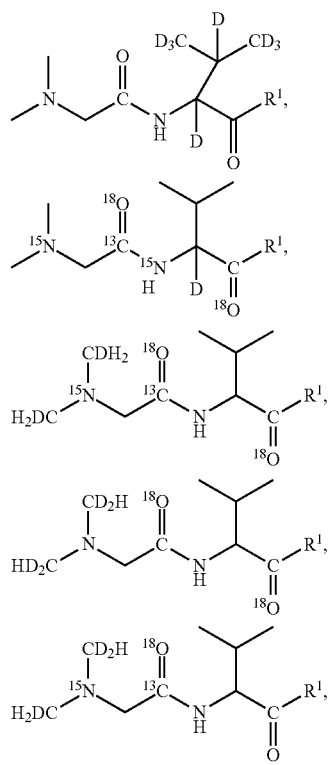

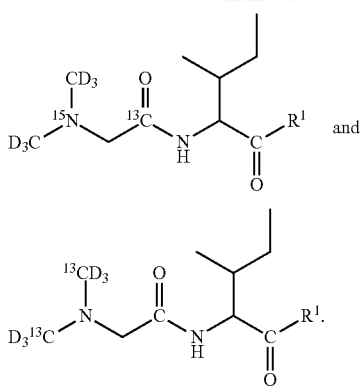
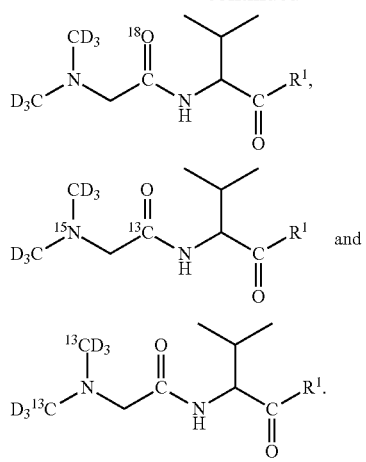
In a further embodiment, the compound is selected from:
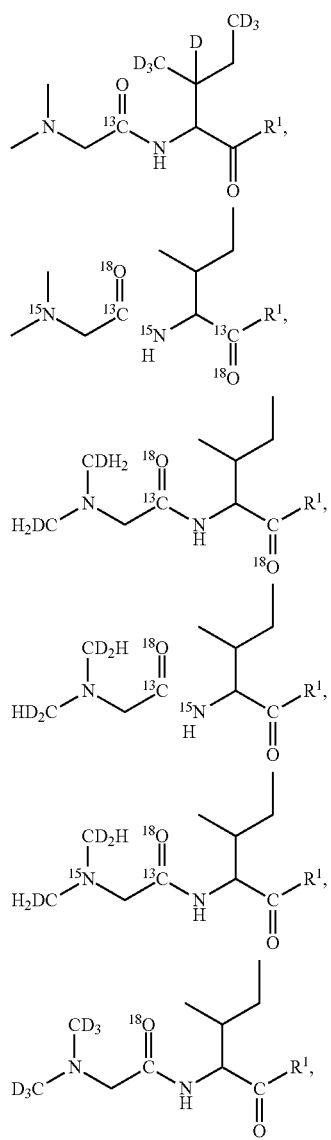
In a further embodiment, the compound is selected from:

-continued

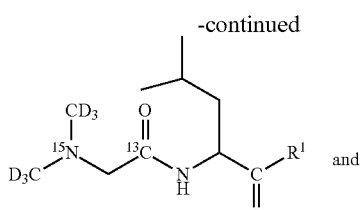 and

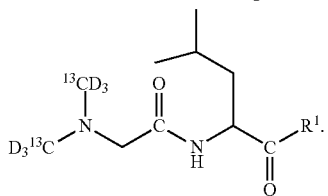

In one embodiment, the compound has the formula:

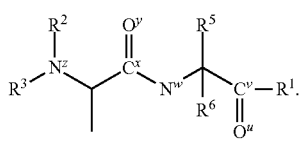 (formula 8)

In a further embodiment, $R^5$ is hydrogen or deuterium; $R^5$ is an isopropyl group optionally containing one or more deuterium atoms and one or more $^{13}C$ atoms; or $R^5$ is a butyl group optionally containing one or more deuterium atoms and one or more $^{13}C$ atoms.

In a further embodiment, the compound is selected from:

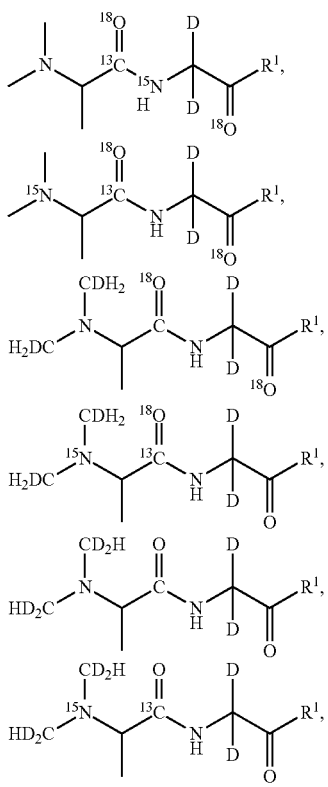

-continued

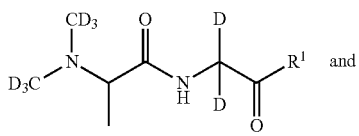

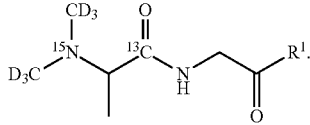

In a further embodiment, the compound is selected from:

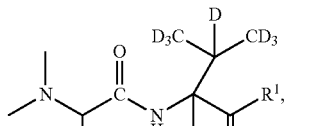

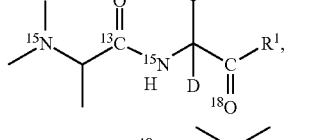

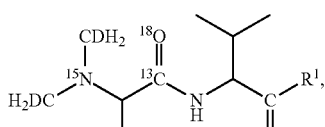

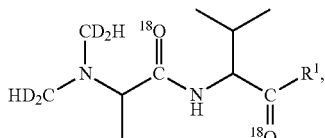

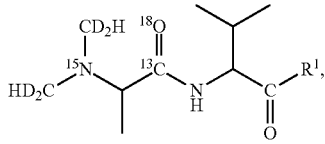

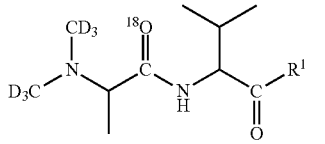 and

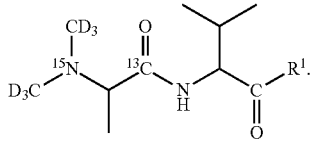

21
In a further embodiment, the compound is selected from:
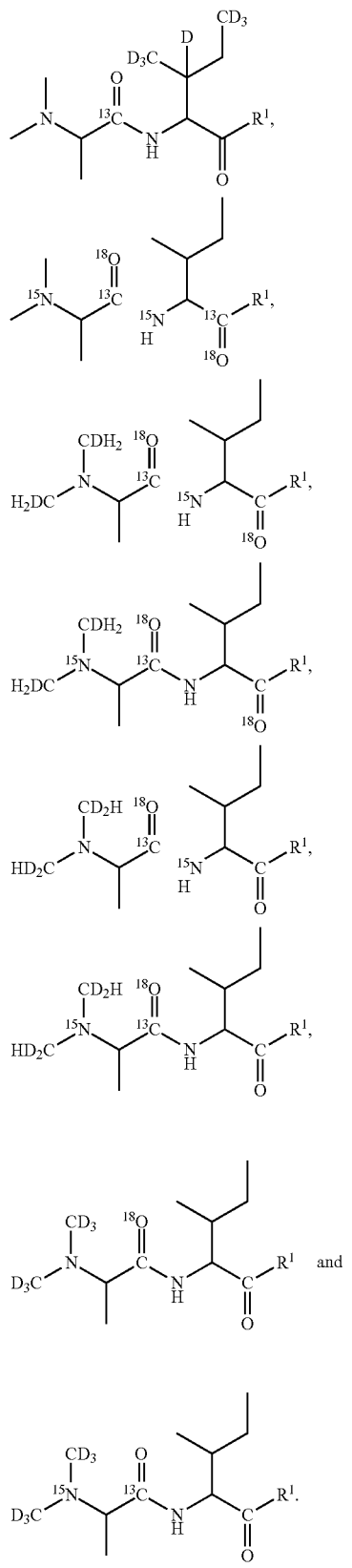
22
In a further embodiment, the compound is selected from:
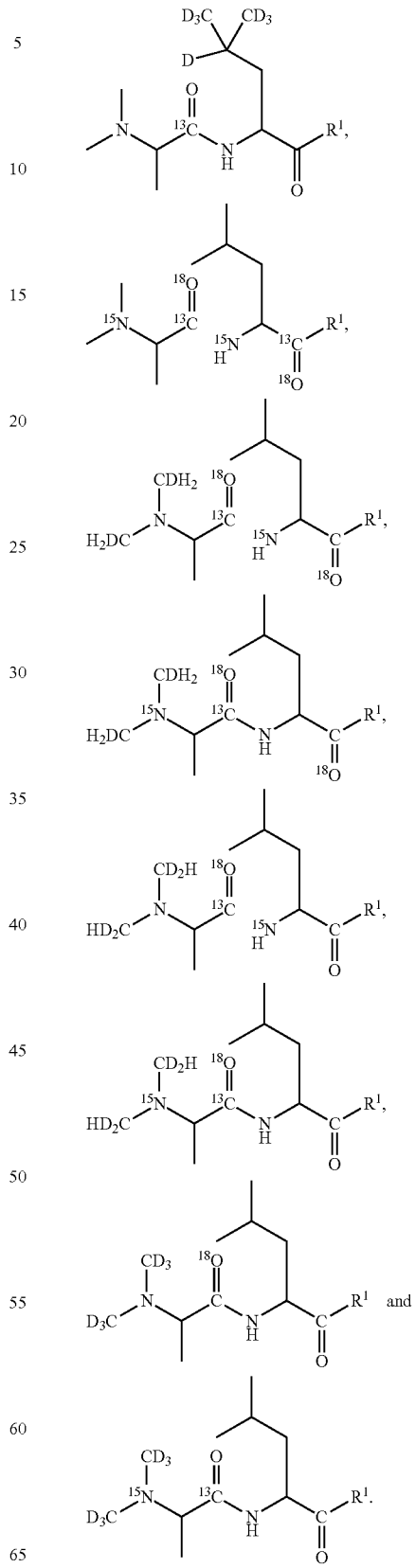

In one embodiment, the compound has the formula:

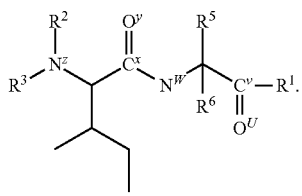

(formula 9)

In a further embodiment, $R^5$ is hydrogen or deuterium; $R^5$ is an isopropyl group optionally containing one or more deuterium atoms and one or more $^{13}C$ atoms; or $R^5$ is a methyl group optionally containing one or more deuterium atoms and wherein the carbon is $^{12}C$ or $^{13}C$.

In a further embodiment, the compound is selected from:

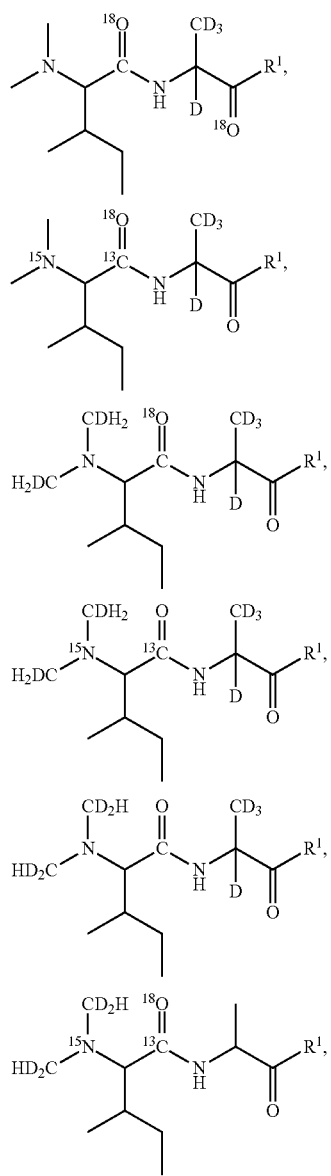

-continued

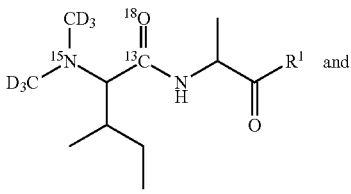

and

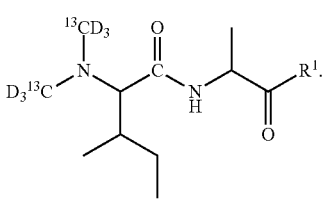

In a further embodiment, the compound is selected from:

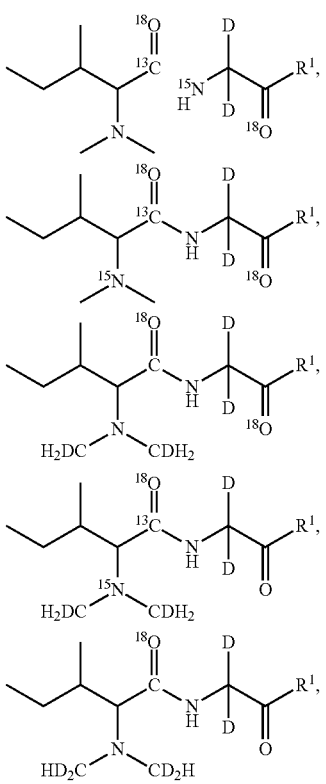

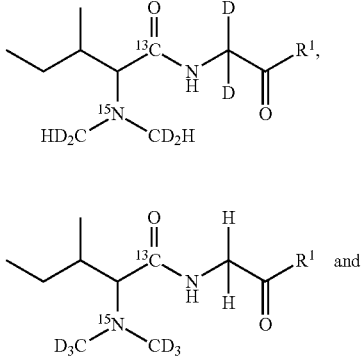

and

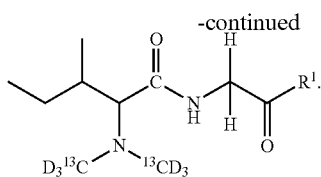

In a further embodiment, the compound is selected from:

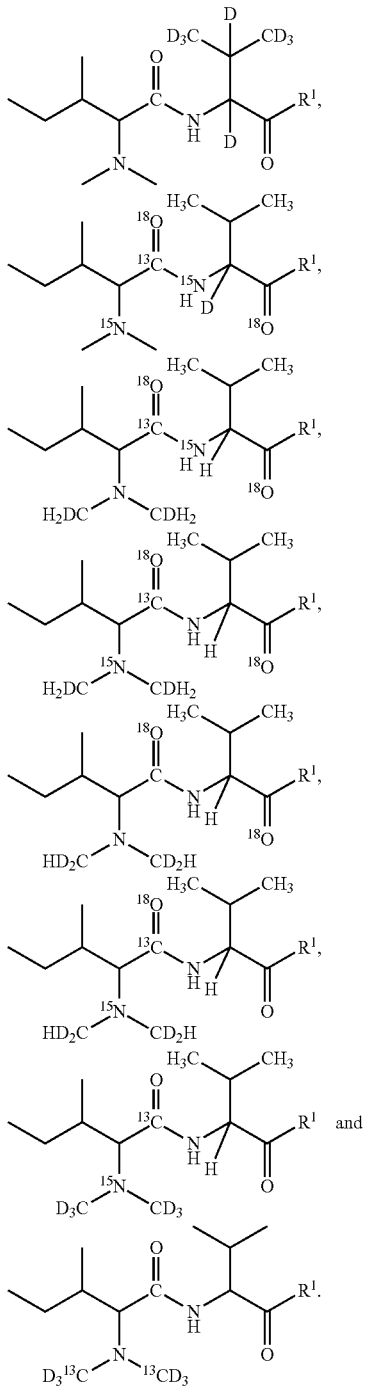

In the above embodiments, $R^2$, $R^3$, $R^4$, $R^5$, $R^6$, $C^x$, $C^v$, $O^y$, $O^U$, $N^z$ and $N^W$ are selected so that the mass of the reporter group and balancing group for each tagging reagent applied to a mixture are different while the overall mass of the tagging reagent remains the same. In one embodiment, $R^2$ and $R^3$ are $CDH_2$, $CD_2H$ or $CD_3$. In a further embodiment, $R^2$ and $R^3$ are $CDH_2$, $N^z$ is $^{15}N$, and $C^x$ is $^{13}C$. In a further embodiment, $R^2$ and $R^3$ are $CDH_2$ and $O^y$ is $^{18}O$. In a further embodiment, $N^z$ is $^{15}N$, $C^x$ is $^{13}C$, and $O^y$ is $^{18}O$.

While it is preferable for the balancing group of the tagging reagents to contain an amino acid as described above, it is also possible to provide 8-plex tagging reagents that use other balancing groups as long as the balancing group provides sufficient atoms able to be isotopically labeled in order to balance the isotopes in the reporter group and provide the same aggregate mass for each of the tagging reagents. One embodiment of the invention provides methods of labeling target molecules using a tagging reagent having the formula:

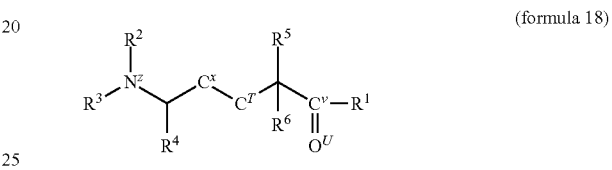

(formula 18)

wherein $R^1$ is an amine reactive group;

$R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$;

$R^4$ and $R^5$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^4$ and $R^5$ optionally contain one or more $^{13}C$ atoms and one or more deuterium atoms;

$R^6$ is hydrogen or deuterium;

$C^T$, $C^V$ and $C^x$, independently of one another, are $^{12}C$ or $^{13}C$, $O^y$ is $^{16}O$ or $^{18}O$; and $N^z$ is $^{14}N$ or $^{15}N$.

In one embodiment, the present invention provides a method of analyzing a mixture containing target molecules comprising the steps of: a) labeling target molecules within a first sample with a first tagging reagent, thereby generating first labeled target molecules; b) labeling target molecules within at least one additional sample with at least one additional tagging reagent, thereby generating additional labeled target molecules; c) combining the labeled target molecules of steps a) and b); d) fragmenting the combined labeled target molecules; and e) analyzing the fragments of the labeled target molecules. The fragments can be analyzed using mass spectrometry. Preferably, the fragmenting step generates immonium ions from the labeled target molecules. Additional tagging reagents having the same mass can be used to label peptides or small molecules in additional samples. The different samples are optionally combined and the relative amounts of the tagged proteins or tagged small molecules compared. One of the samples may be a protein or small molecule present in known amount, allowing the quantitative amounts of target molecules from the other samples to be determined.

A further embodiment comprises labeling target molecules within at least two additional samples with at least two additional tagging reagents; labeling target molecules within at least three additional samples with at least three additional tagging reagents; labeling target molecules within at least four additional samples with at least four additional tagging reagents; labeling target molecules within at least five additional samples with at least five additional tagging reagents; labeling target molecules within at least six additional samples with at least six additional tagging reagents; labeling target molecules within at least seven additional samples with at least seven additional tagging reagents; and labeling target molecules within at least eight additional samples with at least eight additional tagging reagents.

The present invention provides 8-plex and 16-plex tagging reagents able to produce reporter ions that differ by at least one Dalton from one another. Additionally, these tagging reagents can be used to provide 4-plex and 8-plex tagging reagents whose reporter ions differ by two or more Daltons from one another. In a further embodiment, the generated immonium ions of each tagging reagent have a mass that differs from any of the other tagging reagents by two or more Daltons.

In a further embodiment, each tagging reagent comprises a N,N-dimethylated amino acid based reporter group, an amine reactive group, and an amino acid based balancing group located between the reporter group and amine reactive group. One or more atoms in the reporter group, balancing group, or both, are isotopically heavy versions of the atom. The reporter group of each tagging reagent has a mass different than the reporter groups of the other tagging reagents, the balancing group of each tagging reagent has a mass different than the balancing groups of other tagging reagents, and the aggregate mass of the reporter groups plus the balancing group for each tagging reagent is the same.

By "amino acid based balancing group", it is meant that the balancing group comprises an amino acid, where the carboxyl group forms a bond with the amine reactive group or the target molecule, and the N-terminus forms a peptide bond with a second amino acid. The carbonyl group of the second amino acid will also be part of the balancing group. The balancing group of each tagging reagent has the formula:

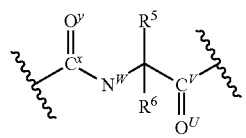

(formula 11)

wherein $R^5$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^5$ optionally contains one or more $^{13}C$ atoms and one or more deuterium atoms; $R^6$ is hydrogen or deuterium; $C^V$ and $C^x$, independently of one another, are $^{12}C$ or $^{13}C$, $O^U$ and $O^y$, independently of one another, are $^{16}O$ or $^{18}O$; and $N^W$ is $^{14}N$ or $^{15}N$.

Preferably, $R^5$ is selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^5$ is selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

By "N,N-dimethylated amino acid based reporter group", it is meant that reporter group comprises an N,N-dimethylated amino acid with the exception that the carbonyl group of the amino acid will not form part of the reporter group. The reporter group of each tagging reagent has the formula:

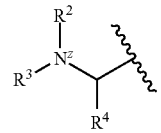

(formula 12)

wherein $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$; $R^4$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^4$ optionally contains one or more $^{13}C$ atoms and one or more deuterium atoms; and $N^z$ is $^{14}N$ or $^{15}N$.

Preferably, $R^4$ is selected from the group consisting of branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_6$ to $C_{18}$ aryl groups and $C_6$ to $C_{18}$ arylalkyl groups. In one embodiment, $R^4$ is selected from the group consisting of branched and unbranched $C_1$ to $C_3$ alkyl groups, $C_1$ to $C_3$ cycloalkyl groups, and $C_2$ to $C_3$ alkenyl groups. Preferably, at least one of $R^2$ or $R^3$ contains a deuterium atom, $N^z$ is $^{15}N$, or $N^W$ is $^{15}N$.

The amine reactive group of each tagging reagent can be any functional group able to react with an amine group of a peptide or small molecule, thereby forming bond between the peptide and the balancing group of the tagging reagent. In one embodiment, the amine reactive group has the formula:

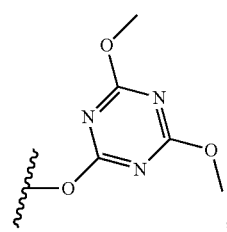

(formula 13)

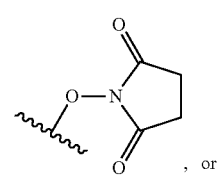

(formula 14)

, or

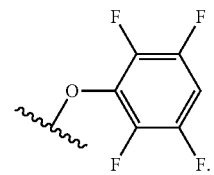

(formula 20)

In a further embodiment, the dimethylated amino acid based reporter group is selected from:
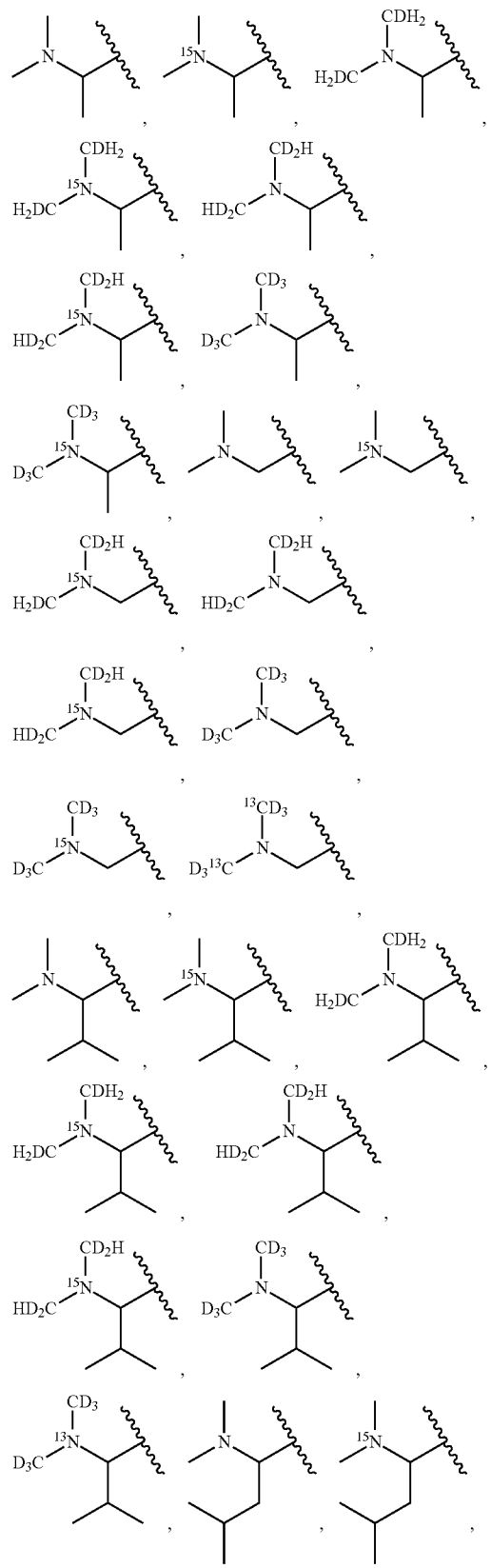
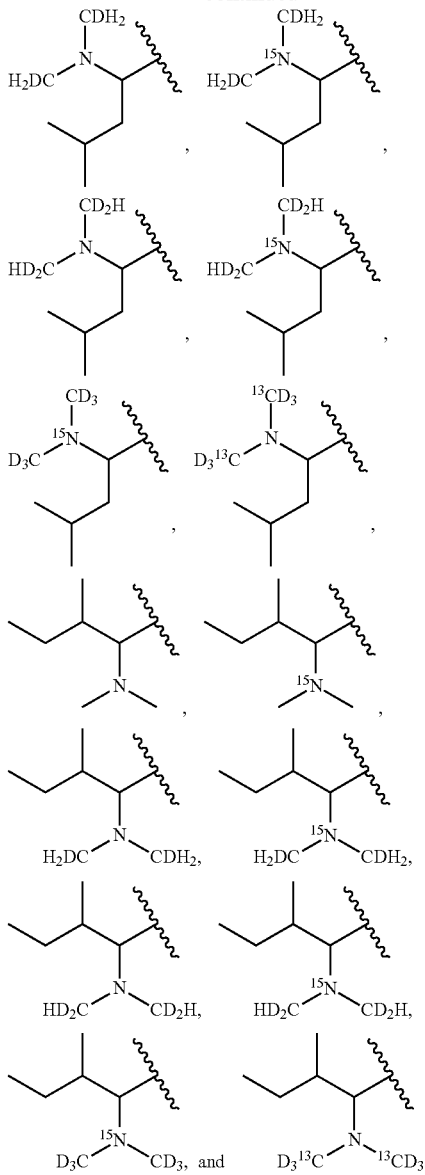
In a further embodiment, the amino acid based balancing group is selected from:
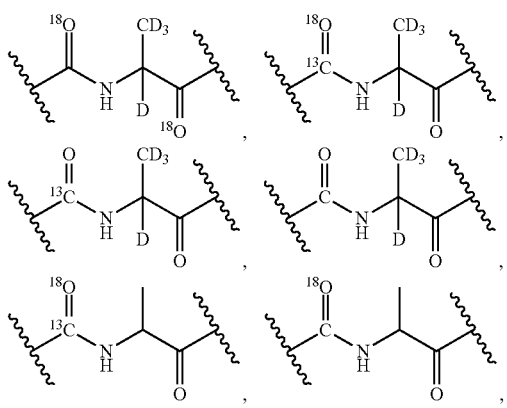

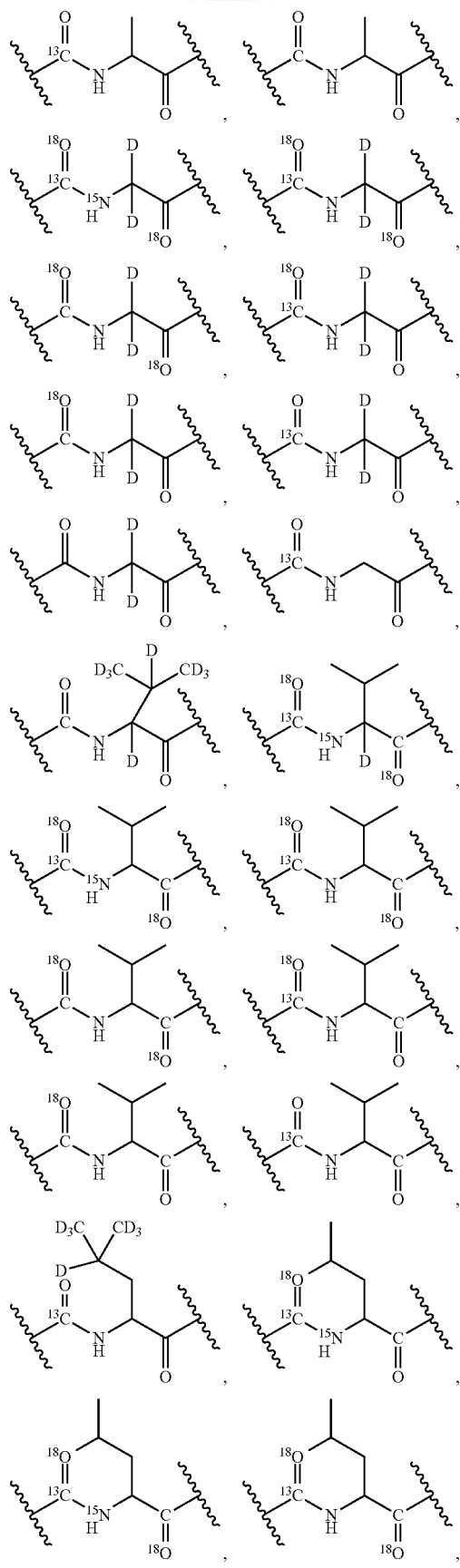
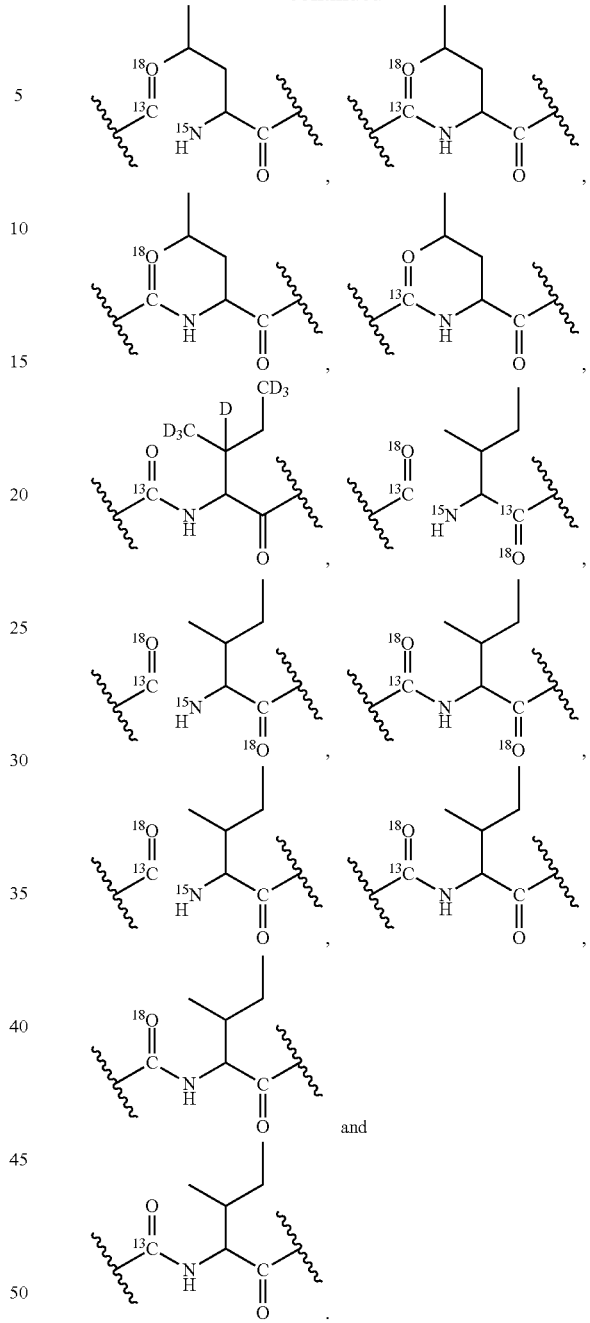

Labeling the target molecules comprises the step of reacting the amine reactive group of the tagging reagents with an amine group of the target molecule. In one embodiment, the target molecules are peptides, metabolites or neurotransmitters. For peptides, the amine reactive group is reacted with the N-terminus of the peptides, and/or with an ε-amino group within the peptides. In one embodiment, the peptides are enzyme digested peptides.

Methods of Analyzing a Mixture Using 16-plex Tagging Reagents

The tagging reagents of the present invention also allow samples to be labeled with up to 16 tagging reagents, where each of the tagging reagents have the same aggregate mass but where the mass of each reporter group and balancing group are different. Where the tagging reagents comprise two amino acids as described above, these 16-plex reagents are easily produced by swapping the amino acid of the balancing group with the amino acid of the reporter group. Because the same amino acids are used in the tagging reagent, the overall mass will remain the same. However, the mass of the reporter group, and its different isotopic variations, will be different because the reporter group has now been changed. This requires that the two amino acids used in the tagging reagents be different and that the two amino acids have different masses.

For example, an 8-plex series of tagging reagents can comprise N,N-dimethyl leucine (which will make up the reporter group) and alanine (which will make up the balancing group) as depicted in Scheme 2 below. This series of tagging reagents can be expanded to a 16-plex series by using tagging reagents that have switched the alanine and leucine amino acids resulting in a reporter group made from the N,N-dimethyl alanine and a balancing group made from leucine. The overall mass of the tagging reagents are the same, but the mass of the different reporter groups will be different for each 16-plex reagent.

Scheme 2

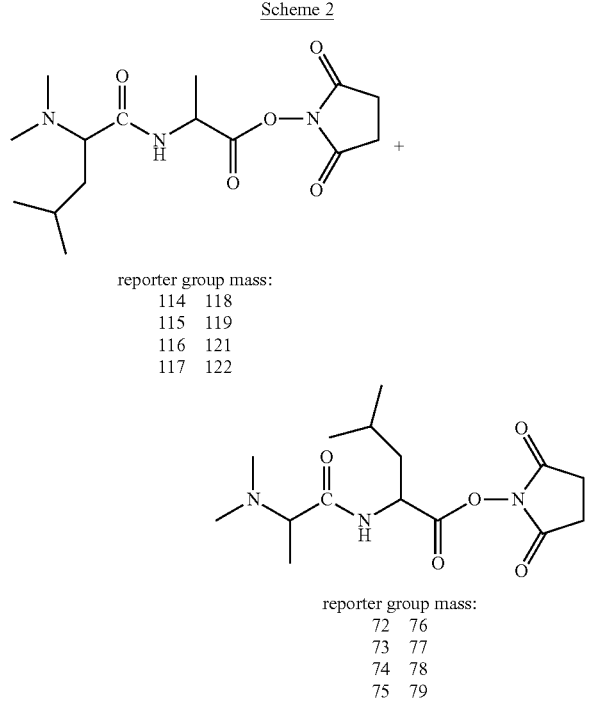

Accordingly, one embodiment of the present invention provides a method of analyzing a mixture containing target molecules comprising the steps of:

a) labeling target molecules within a first sample with a first tagging reagent, thereby generating first labeled target molecules, wherein the first tagging reagent has the formula:

$(CH_3)_2\text{-}AA^1\text{-}AA^2\text{-}R^1$ (formula 16)

where $R^1$ is an amine reactive group; $AA^1$ is a first amino acid having an N-terminus; $AA^2$ is a second amino acid having an N-terminus; and the two $CH_3$ groups are attached to the N-terminus of $AA^1$;

b) labeling target molecules within one or more additional samples with one or more additional tagging reagents, thereby generating additional labeled target molecules, wherein at least one of the additional tagging reagents has the formula:

$(CH_3)_2\text{-}AA^2\text{-}AA^1\text{-}R^1$ (formula 17)

where $AA^1$ and $AA^2$ in the additional tagging reagent are the same amino acids as in the first tagging reagent with the exception that the amino acids may contain different isotopes; and the two $CH_3$ groups are attached to the N-terminus of $AA^2$ in the additional tagging reagent;

c) combining the labeled target molecules of steps a) and b);

d) fragmenting the combined labeled target molecules; and e) analyzing the fragments of the labeled molecules.

In a further embodiment, $AA^1$ and $AA^2$, independently from one another, are any natural or synthetic amino acid with the provision that $AA^1$ and $AA^2$ cannot be the same amino acid. $AA^1$ and $AA^2$ also cannot have the same mass. Preferably, the amino acid is a natural amino acid selected from the group consisting of leucine, isoleucine, alanine, glycine, valine, histidine, phenylalanine, tryptophan, lysine and tyrosine. Even more preferably, the natural amino acid is selected from the group consisting of leucine, isoleucine, alanine, glycine and valine. Alternatively, $AA^1$, $AA^2$, or both, are unnatural, non-standard or synthetic amino acids including, but not limited to, β amino acids, norleucine, norvaline, 2-aminobutylric acid, 3-aminoisobutylric acid, and 3-aminobutylric acid.

Each tagging reagent comprises a reporter group, an amine reactive group, and a balancing group located between the reporter group and amine reactive group, wherein one or more atoms in the reporter group, balancing group, or both, are heavy isotope versions of the atom. The reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same.

Each tagging reagent is able to generate an immonium ion during the fragmentation step. This method allows for anywhere between 2 to 16 samples to be labeled with 2 to 16 tagging reagents. In one embodiment, 2 to 8 samples are labeled wherein the generated reporter ions from each tagging reagent has a mass that differs from the generated reporter ions from the other tagging reagents by two or more Daltons.

In a further embodiment, the balancing group of the 16-plex tagging reagents has the formula:

(formula 11)

wherein $R^5$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^5$ optionally contains one or more $^{13}C$ atoms and one or more deuterium atoms; $R^6$ is hydrogen or deuterium; $C^V$ and $C^x$, independently of one another, are $^{12}C$ or $^{13}C$; $O^U$ and $O^y$, independently of one another, are $^{16}O$ or $^{18}O$; $N^W$ is $^{14}N$ or $^{15}N$.

In a further embodiment, the reporter group of the 16-plex tagging reagents has the formula:

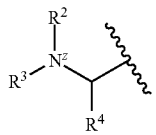
(formula 12)

wherein $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$; $R^4$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^4$ optionally contains one or more $^{13}C$ atoms and one or more deuterium atoms; and $N^z$ is $^{14}N$ or $^{15}N$. Preferably, at least one of $R^2$ or $R^3$ contains a deuterium atom, $N^z$ is $^{15}N$, or $N^W$ is $^{15}N$.

Preferably, $R^4$ and $R^5$ are selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^4$ and $R^5$ are selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

A further embodiment comprises labeling target molecules with from 2 to 8 tagging reagents having the formula $(CH_3)_2$-$AA^1$-$AA^2$-$R^1$. A further embodiment comprises labeling target molecules with from 2 to 8 tagging reagents having the formula $(CH_3)_2$-$AA^2$-$AA^1$-$R^1$.

In a further embodiment, $AA^1$ is leucine and $AA^2$ is selected from the group consisting of alanine, glycine and valine.

In a further embodiment, $AA^1$ is isoleucine and $AA^2$ is selected from the group consisting of alanine, glycine and valine.

In a further embodiment, $AA^1$ is alanine and $AA^2$ is selected from the group consisting of leucine, isoleucine, glycine and valine.

In a further embodiment, $AA^1$ is glycine and $AA^2$ is selected from the group consisting of leucine, isoleucine, alanine and valine.

In a further embodiment, $AA^1$ is valine and $AA^2$ is selected from the group consisting of leucine, isoleucine, glycine and alanine.

Tagging Reagent Compounds and Kits

In one embodiment, the present invention provides mass spectrometry tagging reagents comprising a compound having the formula of:

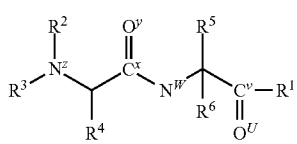
(formula 1)

wherein $R^1$ is an amine reactive group; $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$; $R^4$ and $R^5$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^4$ and $R^5$ optionally contain one or more $^{13}C$ atoms and one or more deuterium atoms; $R^6$ is hydrogen or deuterium; $C^V$ and $C^x$, independently of one another, are $^{12}C$ or $^{13}C$; $O^U$ and $O^y$, independently of one another, are $^{16}O$ or $^{18}O$; and $N^z$ and $N^W$, independently of one another, are $^{14}N$ or $^{15}N$. Preferably at least one of $R^2$ or $R^3$ contains a deuterium atom, $N^z$ is $^{15}N$, or $N^W$ is $^{15}N$. Preferably these tagging reagents are able to generate an immonium ion during fragmentation.

Preferably, $R^4$ and $R^5$ are selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^4$ and $R^5$ are selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

In a further embodiment, the compound has the formula:

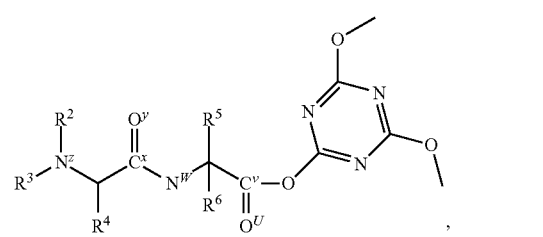
(formula 3)

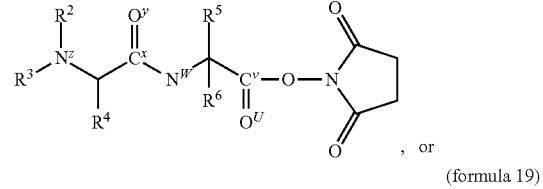
(formula 4)

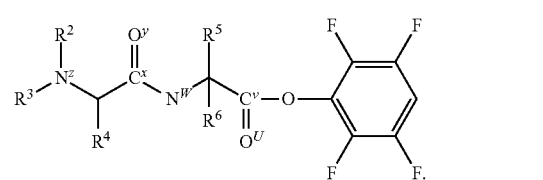
, or
(formula 19)

In a further embodiment, the tagging reagent comprises a compound having the formula:

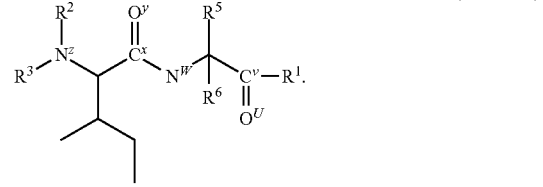
(formula 5)

where $R^5$ is selected from the group consisting of: a methyl group optionally containing one or more deuterium atoms and wherein the carbon is $^{12}C$ or $^{13}C$; hydrogen; deuterium; and an isopropyl group optionally containing one or more deuterium atoms and one or more $^{13}C$ atoms.

In a further embodiment, the tagging reagent comprises a compound having the formula:

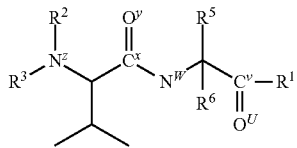

(formula 6)

where $R^5$ is selected from the group consisting of: a methyl group optionally containing one or more deuterium atoms and wherein the carbon is $^{12}C$ or $^{13}C$; hydrogen; deuterium; and a butyl group optionally containing one or more deuterium atoms and one or more $^{13}C$ atoms.

In a further embodiment, the tagging reagent comprises a compound having the formula:

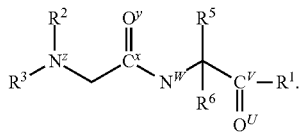

(formula 7)

where $R^5$ is selected from the group consisting of: a methyl group optionally containing one or more deuterium atoms and wherein the carbon is $^{12}C$ or $^{13}C$; an isopropyl group optionally containing one or more deuterium atoms and one or more $^{13}C$ atoms; and a butyl group optionally containing one or more deuterium atoms and one or more $^{13}C$ atoms.

In a further embodiment, the tagging reagent comprises a compound having the formula:

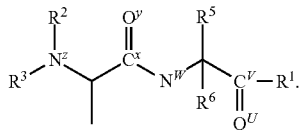

(formula 8)

where $R^5$ is selected from the group consisting of: hydrogen; deuterium; an isopropyl group optionally containing one or more deuterium atoms and one or more $^{13}C$ atoms; and a butyl group optionally containing one or more deuterium atoms and one or more $^{13}C$ atoms.

In a further embodiment, the tagging reagent comprises a compound having the formula:

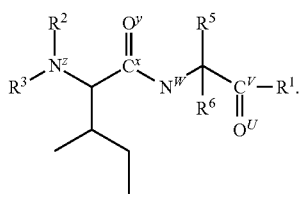

(formula 9)

where $R^5$ is selected from the group consisting of: a methyl group optionally containing one or more deuterium atoms and wherein the carbon is $^{12}C$ or $^{13}C$; hydrogen; deuterium; and an isopropyl group optionally containing one or more deuterium atoms and one or more $^{13}C$ atoms.

The present invention also provides a kit comprising two or more tagging reagents, wherein each tagging reagent comprises a reporter group, an amine reactive group, and a balancing group located between the reporter group and amine reactive group, wherein one or more atoms in the reporter group, balancing group, or both, are isotopically heavy versions of the atom; and wherein the reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same. Preferably, the tagging reagents are able to generate an immonium ion.

The balancing group of each tagging reagent has the formula:

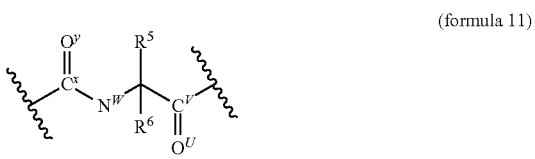

(formula 11)

wherein $R^5$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^5$ optionally contains one or more $^{13}C$ atoms and one or more deuterium atoms; $R^6$ is hydrogen or deuterium; $C^V$ and $C^x$, independently of one another, are $^{12}C$ or $^{13}C$, $O^U$ and $O^y$, independently of one another, are $^{16}O$ or $^{18}O$; and $N^W$ is $^{14}N$ or $^{15}N$.

Preferably, $R^5$ is selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^5$ is selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

The reporter group of each tagging reagent has the formula:

(formula 12)

wherein $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$; $R^4$ is selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein $R^4$ optionally contains one or more $^{13}C$ atoms and one or more deuterium atoms; and $N^z$ is $^{14}N$ or $^{15}N$; and wherein at least one of $R^2$ or $R^3$ contains a deuterium atom, $N^z$ is $^{15}N$, or $N^W$ is $^{15}N$.

Preferably, $R^4$ is selected from the group consisting of branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_6$ to $C_{18}$ aryl groups and $C_6$ to $C_{18}$ arylalkyl groups. In one embodiment, $R^4$ is selected from the group consisting of branched and unbranched $C_1$ to $C_3$ alkyl groups, $C_1$ to $C_3$ cycloalkyl groups, and $C_2$ to $C_3$ alkenyl groups. Preferably, at least one of $R^2$ or $R^3$ contains a deuterium atom, $N^z$ is $^{15}N$, or $N^W$ is $^{15}N$.

The amine reactive group of each tagging reagent can be any functional group able to react with an amine group of a peptide or small molecule, thereby forming bond between the peptide and the balancing group of the tagging reagent. In one embodiment, the amine reactive group has the formula:

(formula 13)

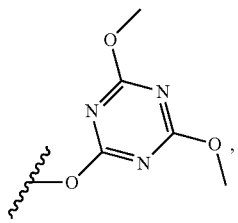

(formula 14)

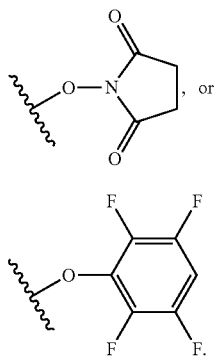, or (formula 20)

In one embodiment, the reporter groups of the tagging reagents of the present invention are derived from natural amino acids where the amino group in the amino acid which makes up the reporter group has been dimethylated.

The present invention also provides a kit where at least one tagging reagent has the formula:

$(CH_3)_2\text{-}AA^1\text{-}AA^2\text{-}R^1$ (formula 16)

where $R^1$ is an amine reactive group; $AA^1$ is a first amino acid having an N-terminus; $AA^2$ is a second amino acid having an N-terminus; and the two $CH_3$ groups are attached to the N-terminus of $AA^1$; and wherein at least one tagging reagent has the formula:

$(CH_3)_2\text{-}AA^2\text{-}AA^1\text{-}R^1$ (formula 17)

where $AA^1$ and $AA^2$ are the same amino acids as in the first tagging reagent with the exception that the amino acids may contain different isotopes; and the two $CH_3$ groups are attached to the N-terminus of $AA^2$;

$AA^1$ and $AA^2$, independently from one another, are any amino acid, preferably a natural amino acid, with the provision that $AA^1$ and $AA^2$ cannot be the same amino acid or have the same mass. Preferably, $AA^1$ and $AA^2$, independently from one another, are selected from the group consisting of leucine, isoleucine, alanine, glycine and valine.

In a further embodiment, the kit comprises 2 to 8 tagging reagents having the formula $(CH_3)_2\text{-}AA^1\text{-}AA^2\text{-}R^1$. In another embodiment, the kit comprises 2 to 8 tagging reagents having the formula $(CH_3)_2\text{-}AA^2\text{-}AA^1\text{-}R^1$.

In one embodiment, the kit comprises two or more tagging reagents, three or more tagging reagents, four or more tagging reagents, five or more tagging reagents, six or more tagging reagents, seven or more tagging reagents, eight or more tagging reagents, nine or more tagging reagents, ten or more tagging reagents, eleven or more tagging reagents, twelve or more tagging reagents, thirteen or more tagging reagents, fourteen or more tagging reagents, fifteen or more tagging reagents, or sixteen or more tagging reagents.

In a further embodiment, the tagging reagents of the present invention comprise a dimethylated leucine derived compound having the formula (the mass of the reporter groups are indicated):

114

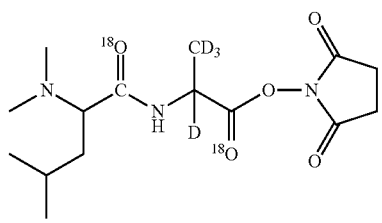

115

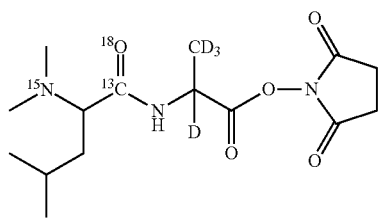

116

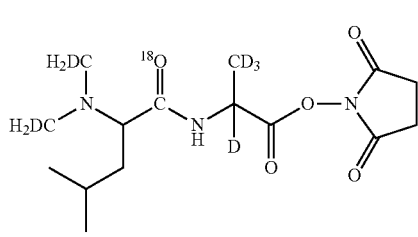

117

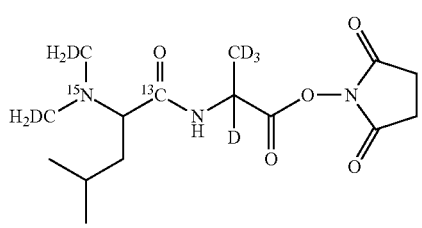

118

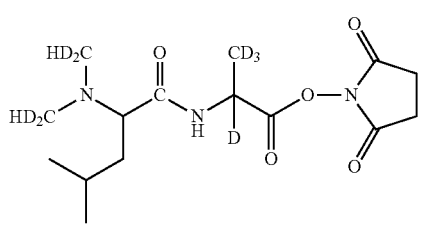

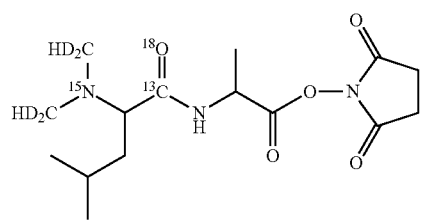
119
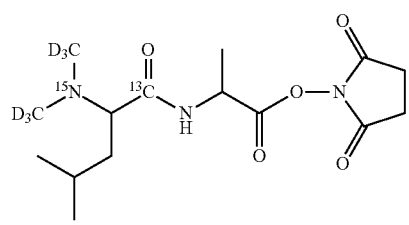
121
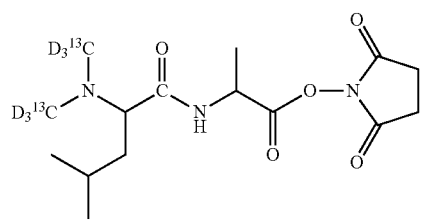
122
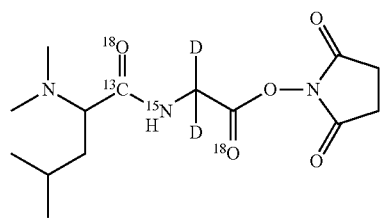
114
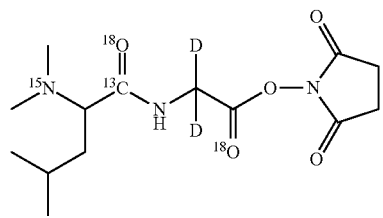
115
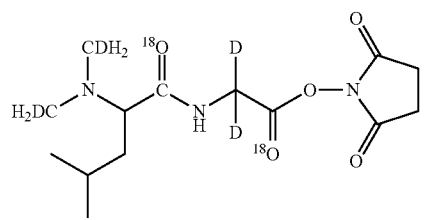
116
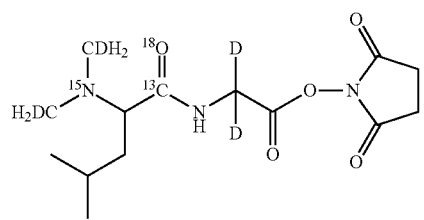
117
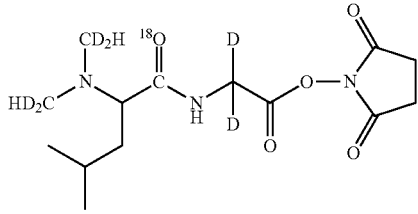
118
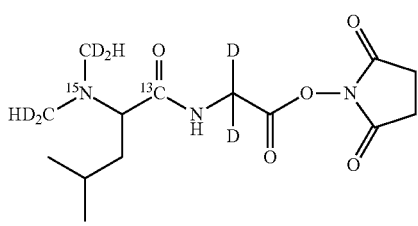
119
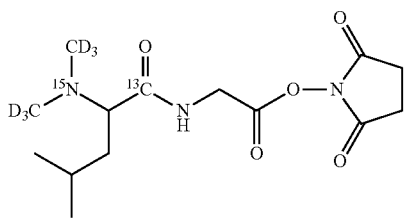
121
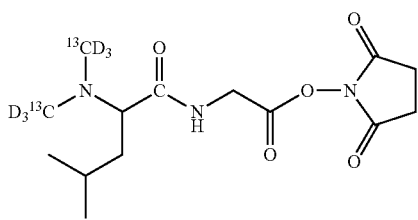
122
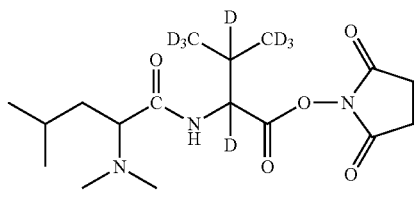
114
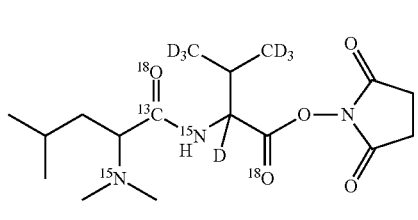
115
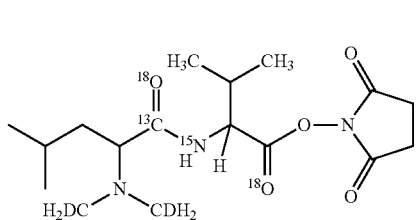
116

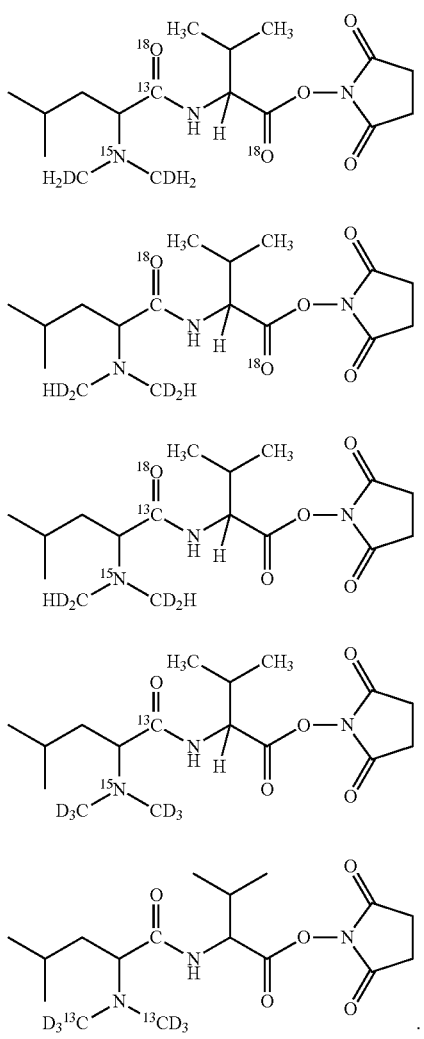
In a further embodiment, the tagging reagents of the present invention comprise a dimethylated alanine derived compound having the formula (the mass of the reporter groups are indicated):
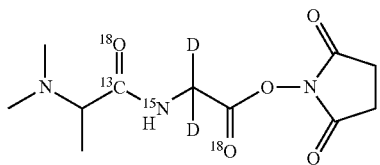
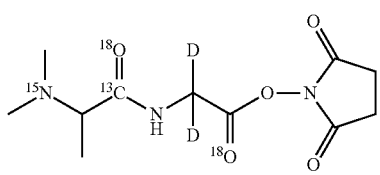
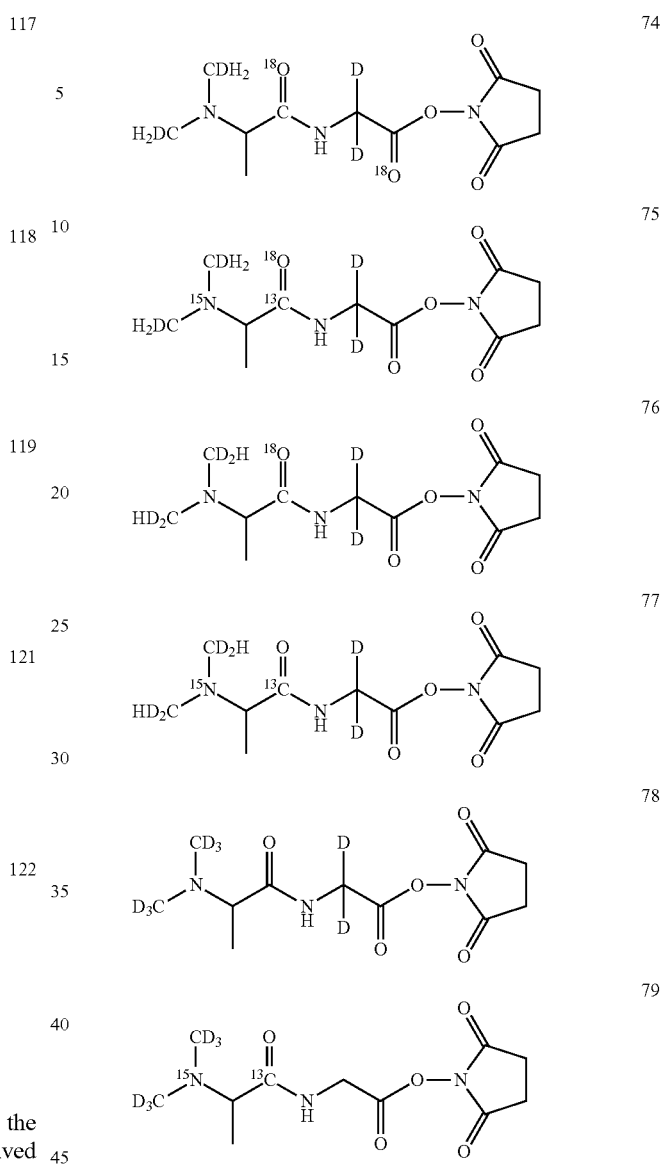

US 9,388,132 B2
45
-continued
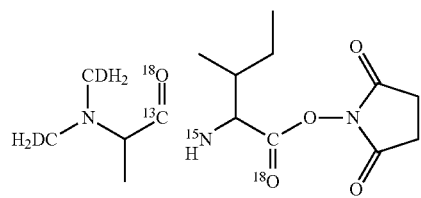
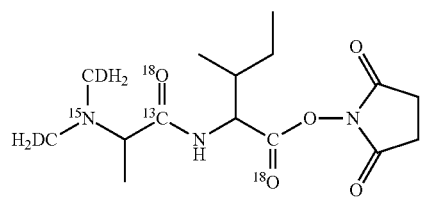
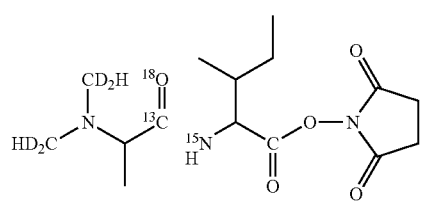
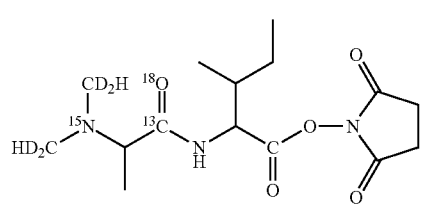
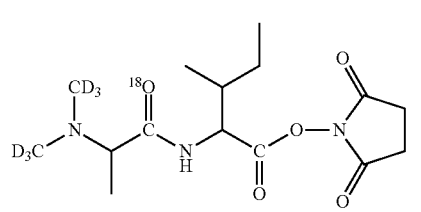
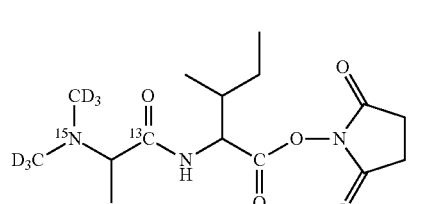
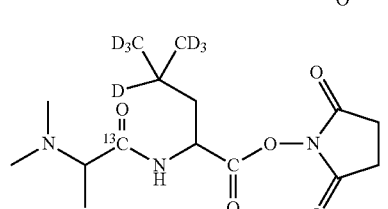
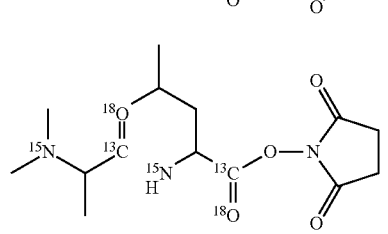
46
-continued
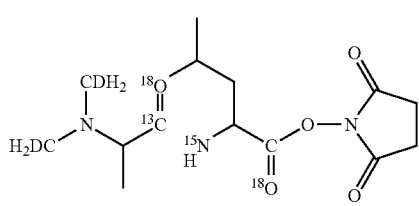
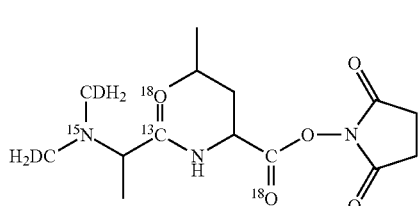
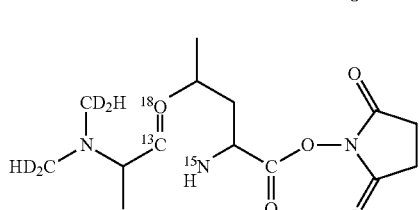
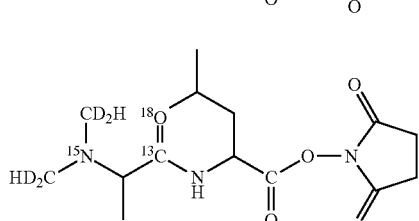
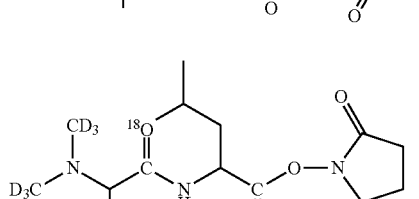
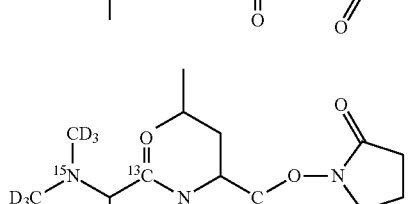
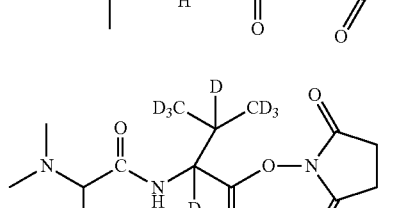
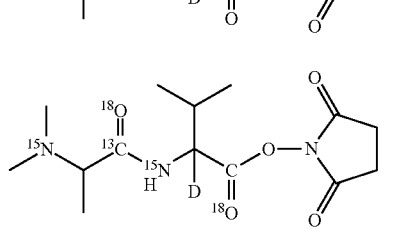

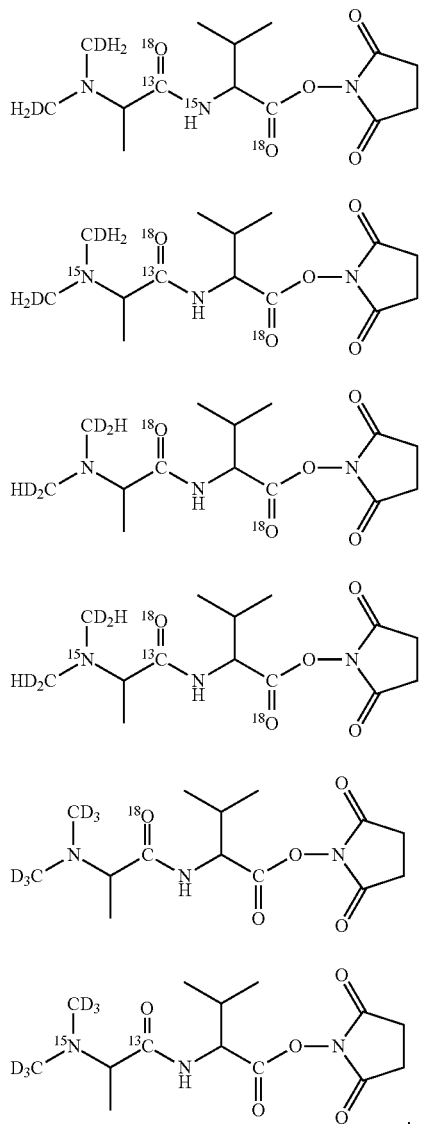
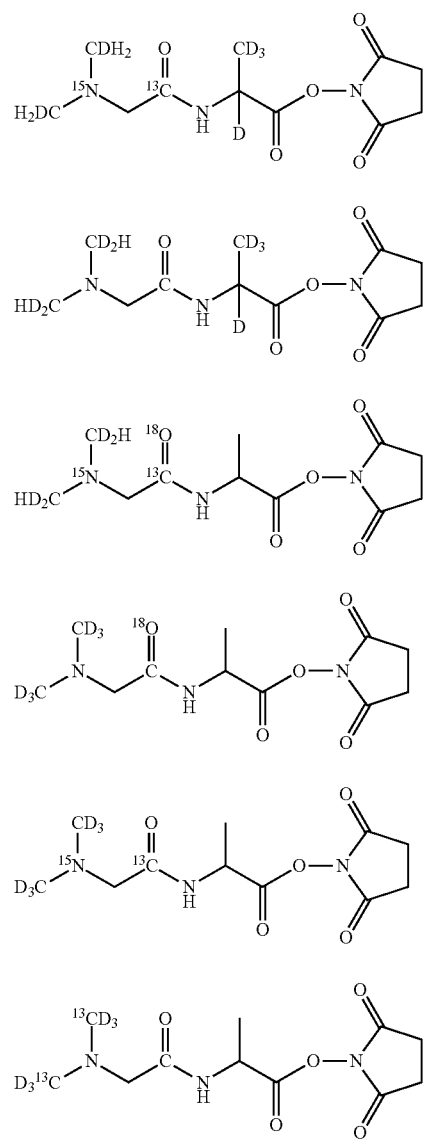
In a further embodiment, the tagging reagents of the present invention comprise a dimethylated glycine derived compound having the formula (the mass of the reporter groups are indicated):
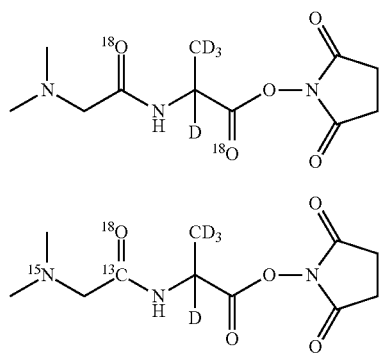
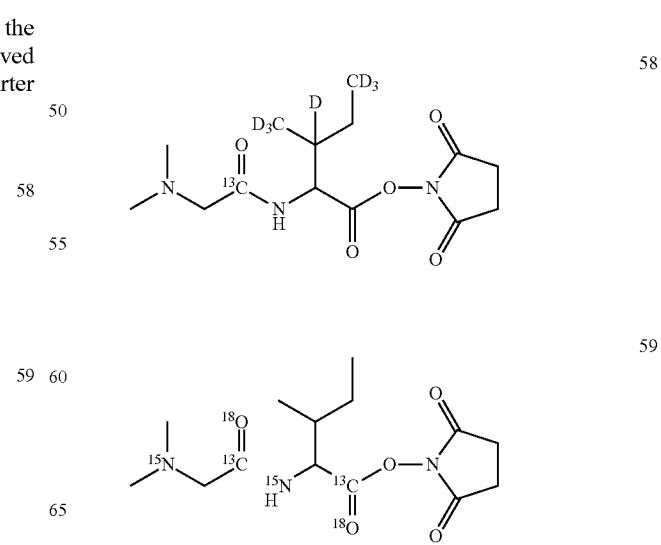

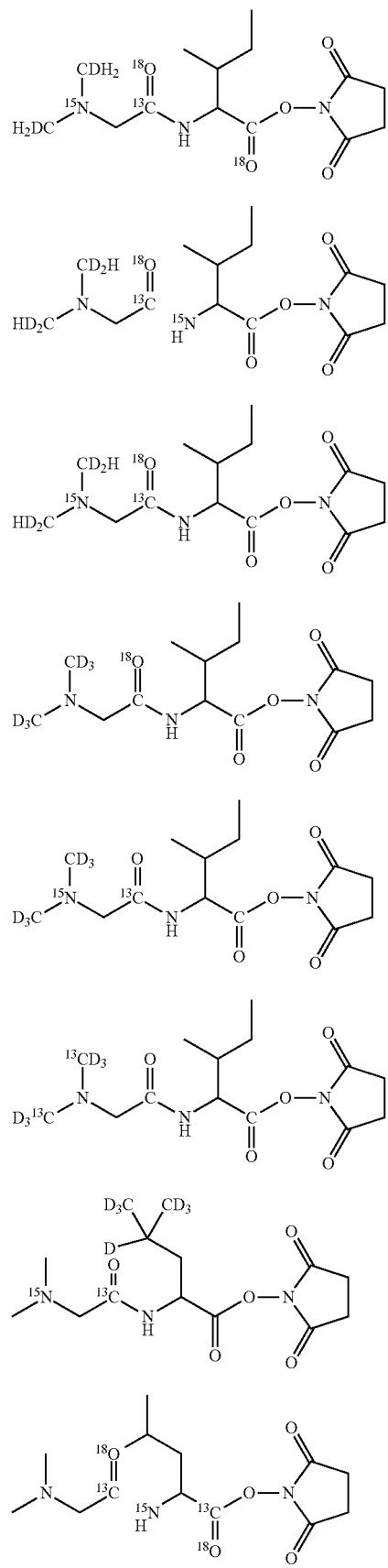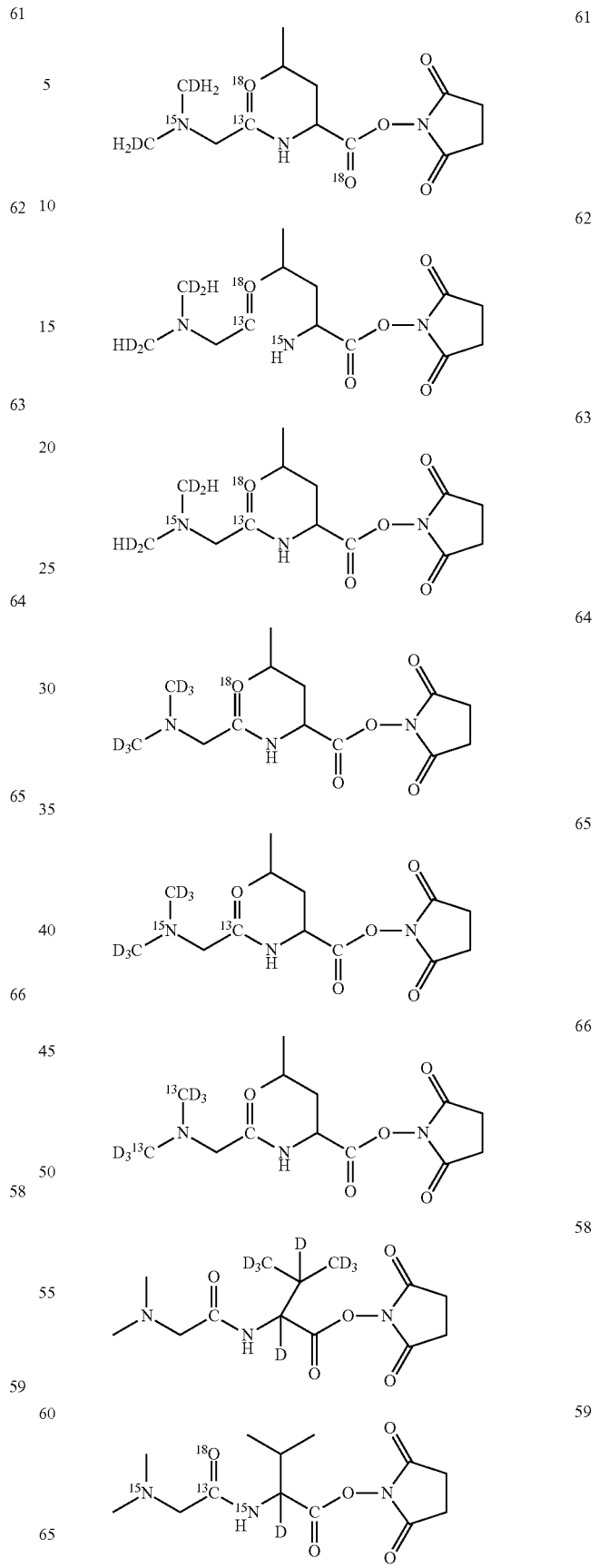

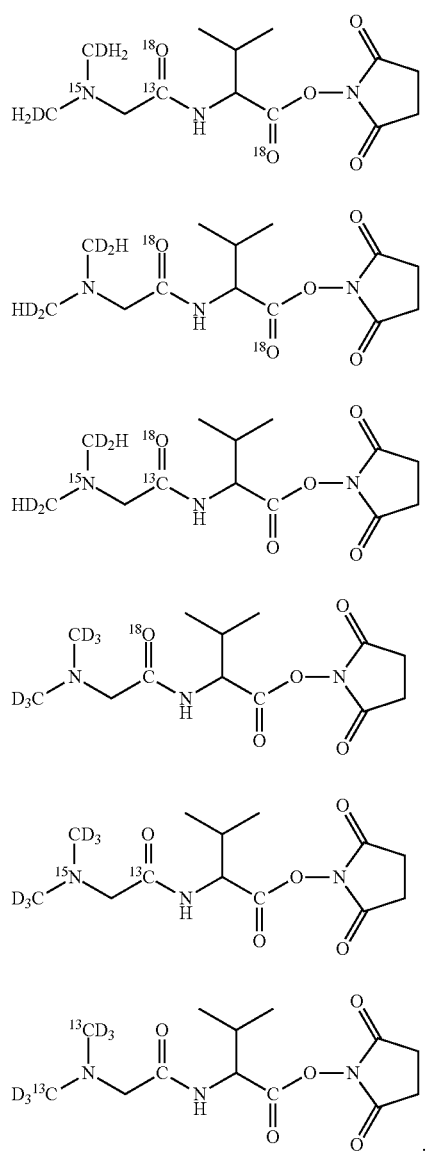
In a further embodiment, the tagging reagents of the present invention comprise a dimethylated isoleucine derived compound having the formula (the mass of the reporter groups are indicated):
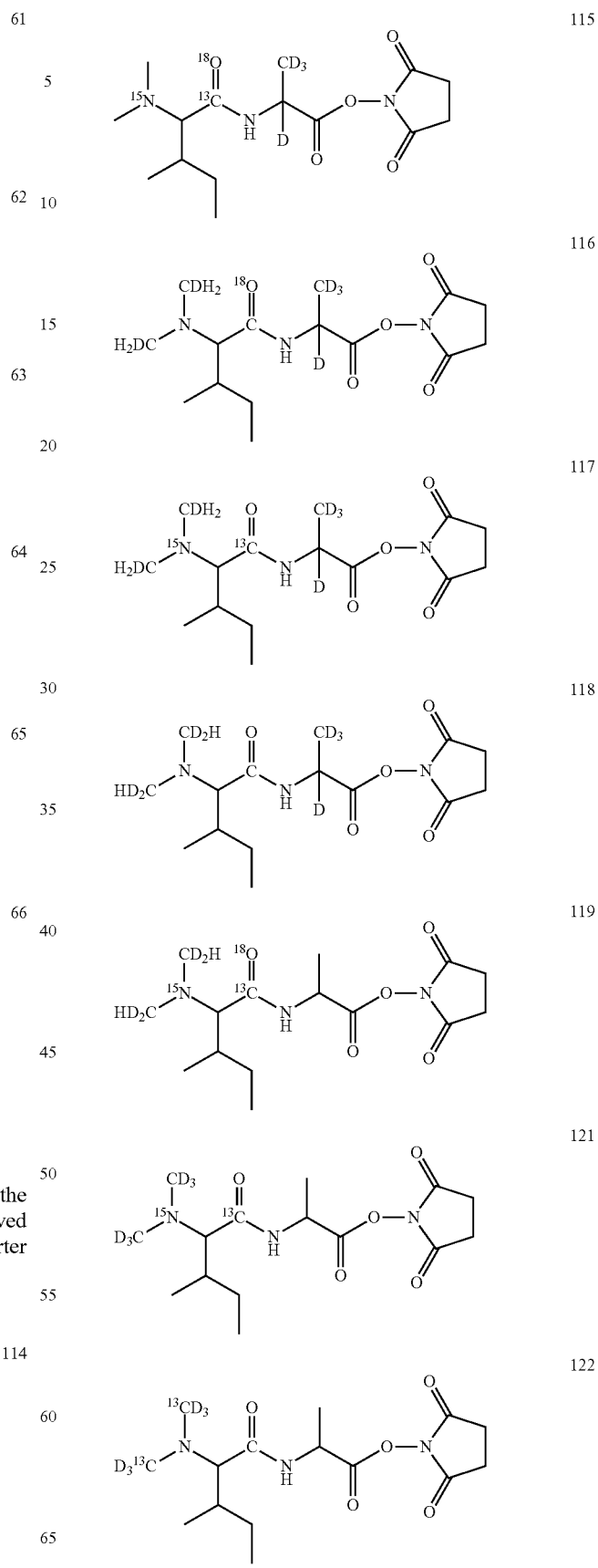

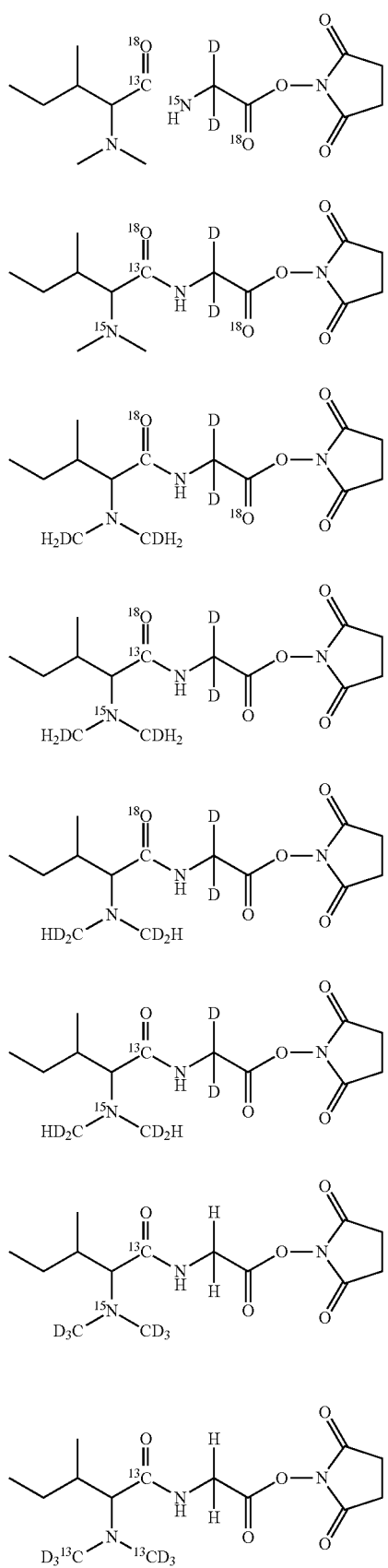

In a further embodiment, the tagging reagents of the present invention comprise a dimethylated valine derived compound having the formula (the mass of the reporter groups are indicated):
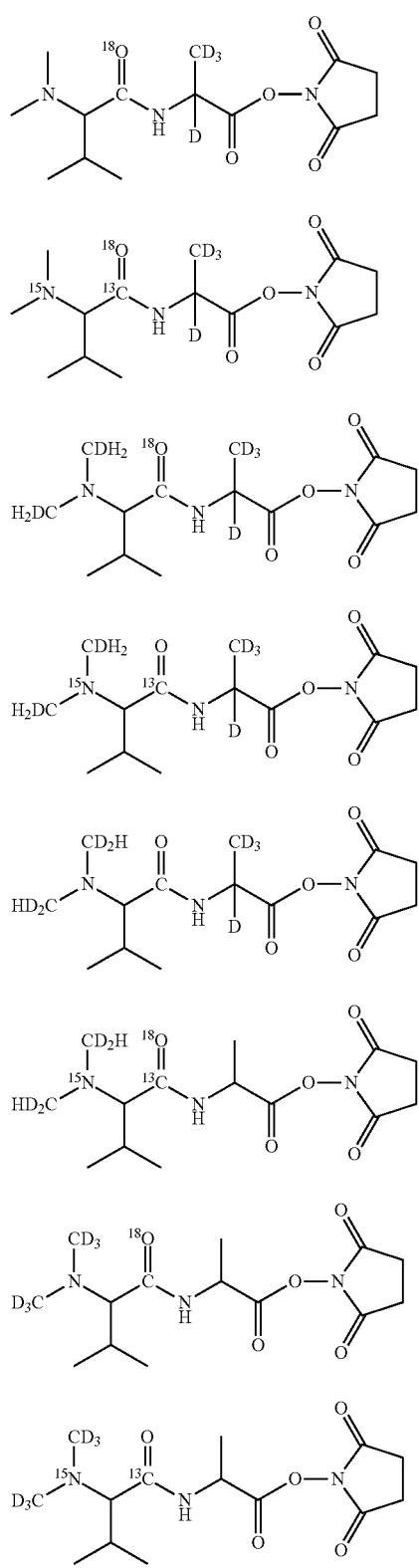
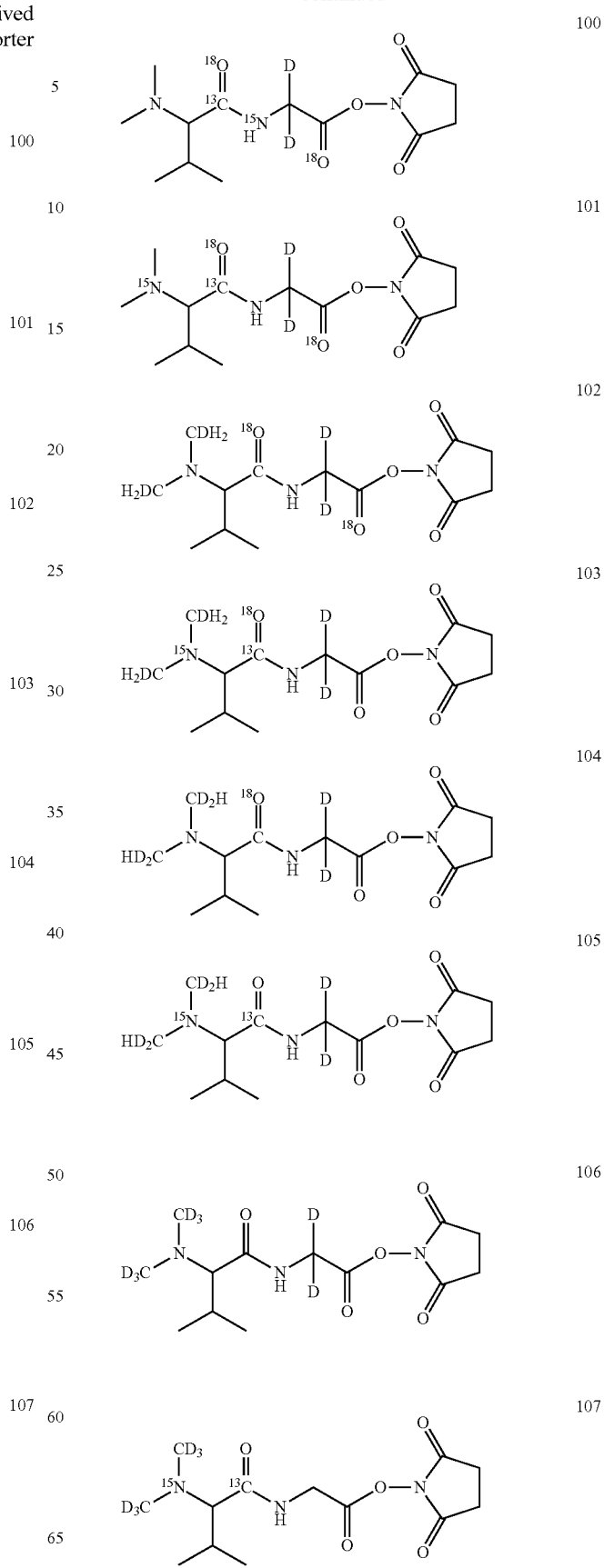

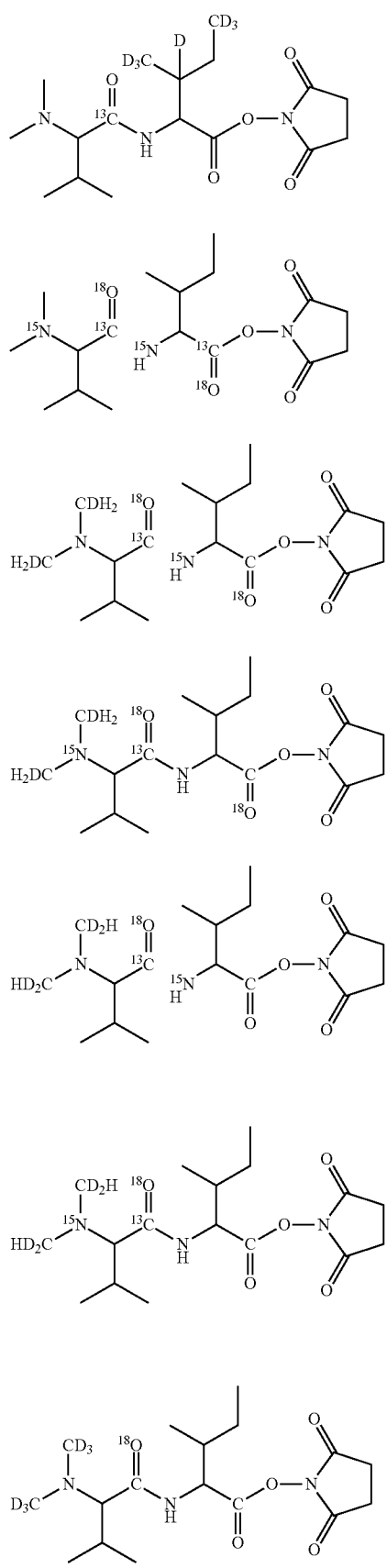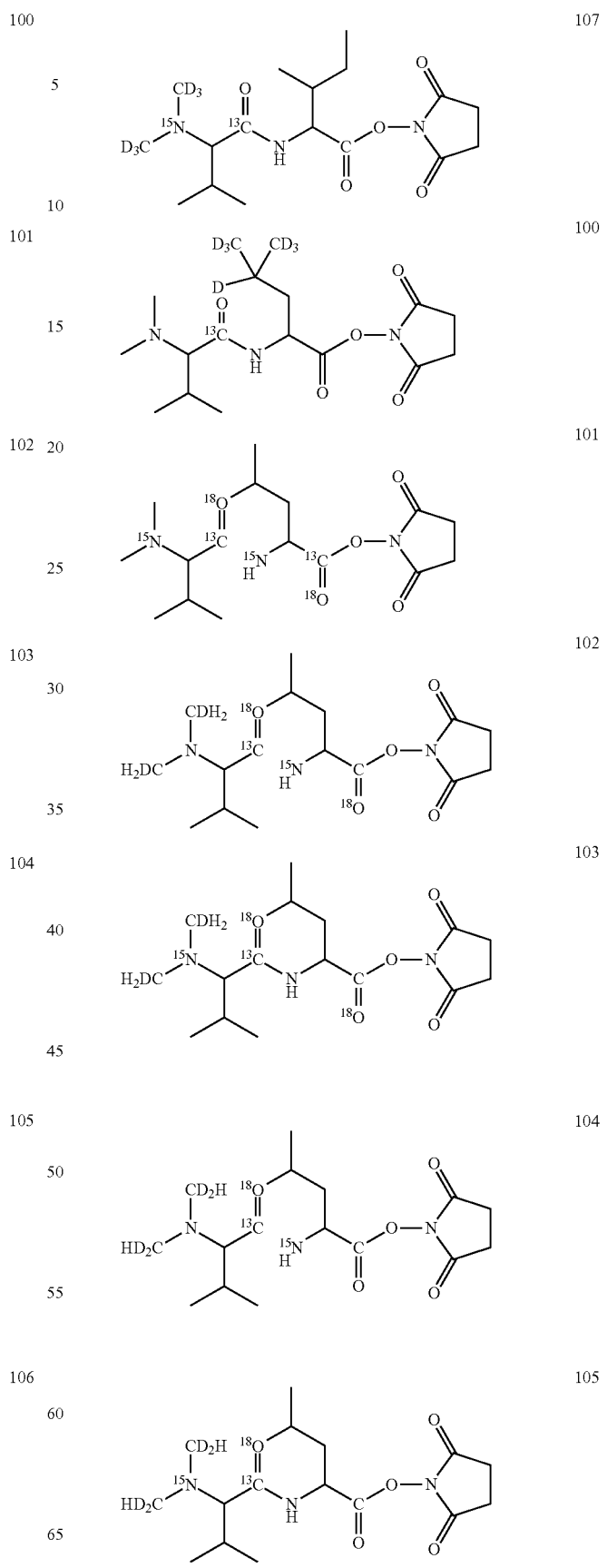

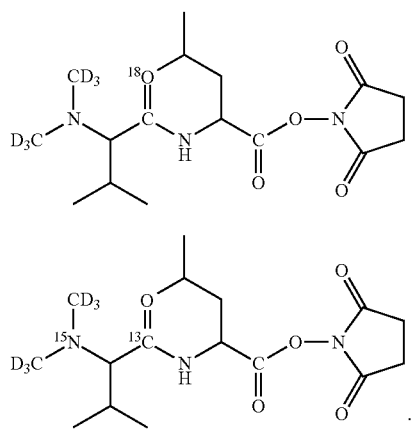

The tagging reagents disclosed herein serve as attractive alternatives for isobaric tag for relative and absolute quantitation (iTRAQ) and tandem mass tags (TMTs) due to their synthetic simplicity, labeling efficiency and improved fragmentation efficiency. The tagging reagents disclosed herein enable simultaneous quantitation of multiple protein/peptide or small molecule samples and identification based on sequence-specific fragmentation. The isobaric reagents can be synthesized in fewer steps using commercially available reagents (one step or two step synthesis), thus offering synthetic simplicity and much reduced cost as compared to other existing technology such as iTRAQ labeling. This feature allows the routine application of these isobaric tagging reagents to many large-scale proteomic and peptidomic studies. In addition to multiplexed quantitation, the reagents disclosed herein based on dimethylated amino acid tagging promote enhanced fragmentation, thus enabling more confident protein identification and superior capability for de novo sequencing. This feature makes the present invention an important tool for endogenous peptide discovery from organisms whose genomes have not been sequenced.

In an embodiment, the invention provides an isotopically enriched sample comprising any of the compounds disclosed herein, including the disclosed compounds having specific isotopic compositions, and methods of using an isotopically enriched sample comprising any of the compounds disclosed herein, including the disclosed compounds having specific isotopic compositions. In a specific embodiment, the invention provides an isotopically enriched sample comprising a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample, and related methods of using these samples, for example for use as a tagging reagent in mass spectrometry. In a specific embodiment, the invention provides an isotopically enriched sample having a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%, and related methods of using these samples, for example for use as a tagging reagent in mass spectrometry. In a specific embodiment, the invention provides an isotopically enriched sample that has been purified with respect to a compound of the invention having a specific isotopic composition, for example using isotope purification methods known in the art, and related methods of using these samples, for example for use as a tagging reagent in mass spectrometry.

BRIEF DESCRIPTION OF THE DRAWINGS

FIG. 3 lists various immonium ions formed by different amino acids. Immonium ions able to give strong signals in $MS^2$ are indicated in bold.

FIGS. 17a and 17b show synthesis steps used to form dimethylated leucine-alanine and dimethylated leucine-glycine, and QTOF MS spectra of the dimethylated amino acid tagging reagents showing the presence of the immonium reporter ions.

DETAILED DESCRIPTION OF THE INVENTION

Definitions

Figure 1:
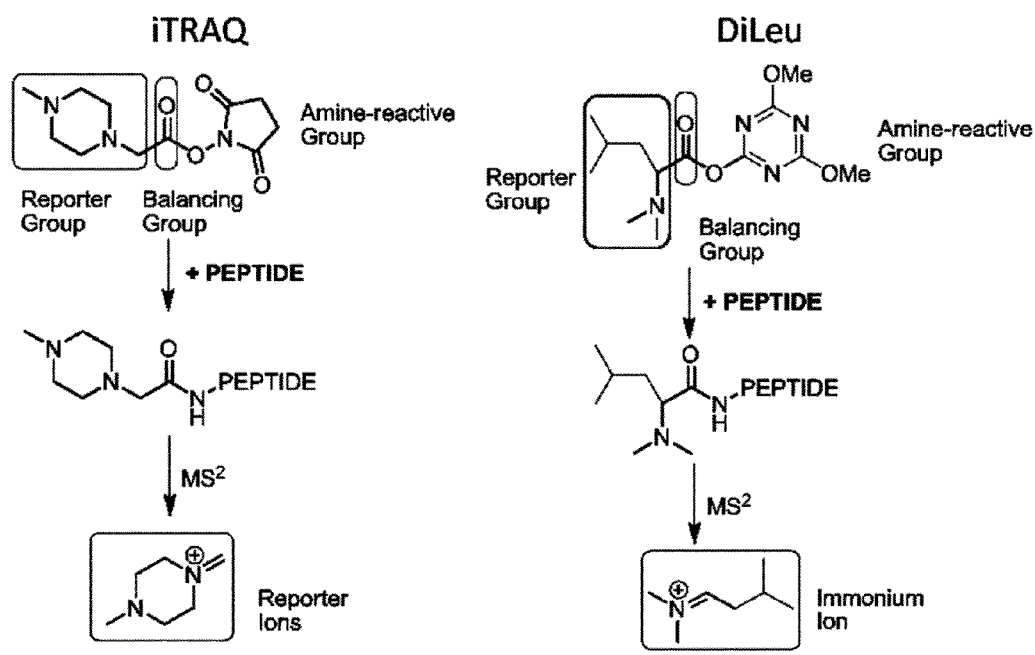
FIG. 1 shows the formation of immonium ions by 4-plex iTRAQ isobaric tags and 4-plex DiLeu isobaric tags.

As used herein the terms "tagging" and "labeling" refers to reacting a reagent or compound with a molecule of interest, including but not limited to peptides, so that one or more functional groups are attached to the molecule of interest. A "tagged" or "labeled" peptide or molecule of interest refers to a peptide or molecule of interest having the one or more functional groups attached.

The terms "peptide" and "polypeptide" are used synonymously in the present disclosure, and refer to a class of compounds composed of amino acid residues chemically bonded together by amide bonds (or peptide bonds). Peptides are polymeric compounds comprising at least two amino acid residues or modified amino acid residues. Peptides include compositions comprising a few amino acids and include compositions comprising intact proteins or modified proteins. Modifications can be naturally occurring or non-naturally occurring, such as modifications generated by chemical synthesis. Modifications to amino acids in polypeptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolytic digestion. Peptides and polypeptides may be generated by substantially complete digestion or by partial digestion of proteins. Identifying or sequencing a peptide refers to determination of is composition, particularly its amino acid sequence, and characterization of any modifications of one or more amino acids comprising the peptide or polypeptide.

"Protein" refers to a class of compounds comprising one or more polypeptide chains and/or modified polypeptide chains. Proteins may be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins may also include non-naturally occurring derivatives, analogues and functional mimetics generated by chemical synthesis. Exemplary derivatives include chemical modifications such as alkylation, acylation, carbamylation, iodination or any modification that derivatizes the protein. In the present invention, proteins may be modified by labeling methods, such as metabolic labeling, enzymatic labeling or by chemical reactions. Proteins may be modified by the introduction of stable isotope tags, for example as is typically done in a stable isotope dilution experiment. Proteins of the present invention may be derived from sources, which include but are not limited to cells, cell or tissue lysates, cell culture medium after cell growth, whole organisms or organism lysates or any excreted fluid or solid from a cell or organism.

"Fragment" refers to a portion of molecule, such as a peptide. Fragments may be singly or multiple charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), surface induced dissociation (SID), laser induced dissociation (LID), electron capture dissociation (ECD), electron transfer dissociation (ETD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a parent analyte, such as a polypeptide analyte, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

An "amine reactive group" of a tagging reagent can be any functional group able to react with an amine group of a peptide or small molecule, thereby forming bond between the peptide or small molecule and the balancing group of the tagging reagent.

An "amino acid" refers to an organic compound containing an amino group ($NH_2$), a carboxylic acid group (COON), and any of various organic side groups that have the basic formula $NH_2CHRCOOH$. Natural amino acids are those amino acids which are produced in nature, such as Isoleucine, alanine, leucine, asparagine, lysine, aspartic acid, methionine, cysteine, phenylalanine, glutamic acid, threonine, glutamine, tryptophan, glycine, valine, proline, serine, tyrosine, arginine, and histidine as well as ornithine and selenocysteine.

The term "alkyl" refers to a monoradical of a branched or unbranched (straight-chain or linear) saturated hydrocarbon and to cycloalkyl groups having one or more rings. Alkyl groups as used herein include those having from 1 to 30 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cycloalkyl groups include those having one or more rings. Cyclic alkyl groups include those having a 3-, 4-, 5-, 6-, 7-, 8-, 9-, 10-, 11- or 12-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 1 to 20 carbon atoms, preferably having from 1 to 12 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9-, 10-, 11- or 12-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocyclic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "halo" refers to a halogen group such as a fluoro (—F), chloro (–Cl), bromo (–Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

As used herein, "isotopically labeled", "isotopic", "isotopes", "isotope", "isotopically-different", "isotopically enriched" and the like refer to compounds (e.g., tagging reagents, target analytes, labeled samples and end-products, etc.) whereby a process has introduced one or more isotopes into the relevant compound in excess of the natural isotopic abundance. "Isotopically-heavy" refers to a compound or fragments/moieties thereof that have been enriched with one or more high mass, or heavy isotopes (e.g., stable isotopes such as deuterium, $^{13}C$, $^{15}N$, and $^{18}O$).

In an embodiment, an isotopically enriched sample comprises a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample. In another embodiment, an isotopically enriched sample has a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched sample is a sample that has been purified with respect to a compound of the invention having a specific isotopic composition, for example using isotope purification methods known in the art.

Novel Isobaric Tandem Mass Taqs

The present inventors previously described a set of novel N,N-dimethylated leucine (DiLeu) 4-plex reagents as an attractive alternative to isobaric tag for relative and absolute quantitation (iTRAQ) reagent for protein and peptide quantitation (F. Xiang, et al., Anal. Chem. 2010, 82. 2817-2825). A notable feature of this labeling approach is the production of intense immonium al ions when a dimethylated amino acid (such as a dimethylated leucine) undergoes tandem mass spectroscopy ($MS^2$) dissociation. The formation of the dimethylated al ion from the previous 4-plex reagent is shown in FIG. 1 along with the immonium ion formed by the iTRAQ reporter ion.

These DiLeu 4-plex isobaric $MS^2$ tagging reagents provided high quantitation efficacy and greatly reduced cost for peptidomics and proteomics. DiLeu reagents also serve as attractive alternatives for iTRAQ and tandem mass tags (TMTs) due to their synthetic simplicity, labeling efficiency and improved fragmentation efficiency. These reagents maintain the isobaric quantitation features present in the iTRAQ reagents, with comparable performance and greatly reduced cost. This makes the DiLeu tandem MS tags a more affordable tool for routine quantitation and methodology development as compared to commercially available 4-plex reagents.

While the previous 4-plex DiLeu reagents provide a cost effective alternative to previously existing isobaric labels (i.e. iTRAQ reagents) for peptide and protein quantitation, the demand for high throughput peptide/protein liquid chromatography $MS^2$ makes 8-plex reagents and 16-plex reagents an even more attractive alternative. Building off of their previous work with 4-plex isobaric tagging reagents, the inventors of the present invention have synthesized isobaric 8-plex tagging reagents which can also be used to provide 16-plex reagents. In the case of the 4-plex reagents, the number of reporter ions was limited by the balancing group, in that case a carbonyl group. Unfortunately, the carbonyl group could only be modified 4 different ways using $^{13}C$ and $^{18}O$. To overcome this limitation, the present invention uses an amino acid to form the balancing group. Amino acids were chosen for the balancing group for several reasons: they can bear more isotopes than a carbonyl group, isotopic amino acids with various isotopic combinations are readily commercially available, and the methods of coupling two amino acids are well established.

As shown below in Scheme 3, the general 8-plex reagent structure comprises a dimethylated amino acid based reporter group (in this example, leucine as shown on the left), an amino acid based balancing group (in this example, alanine as shown in the center), and an amine reactive group (in this example, an NHS ester as shown in the center).

Scheme 3

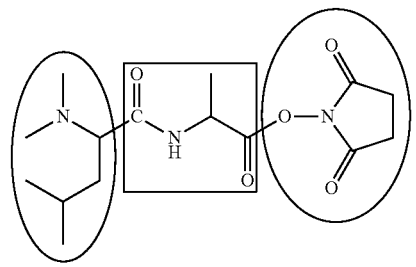

Figure 2:
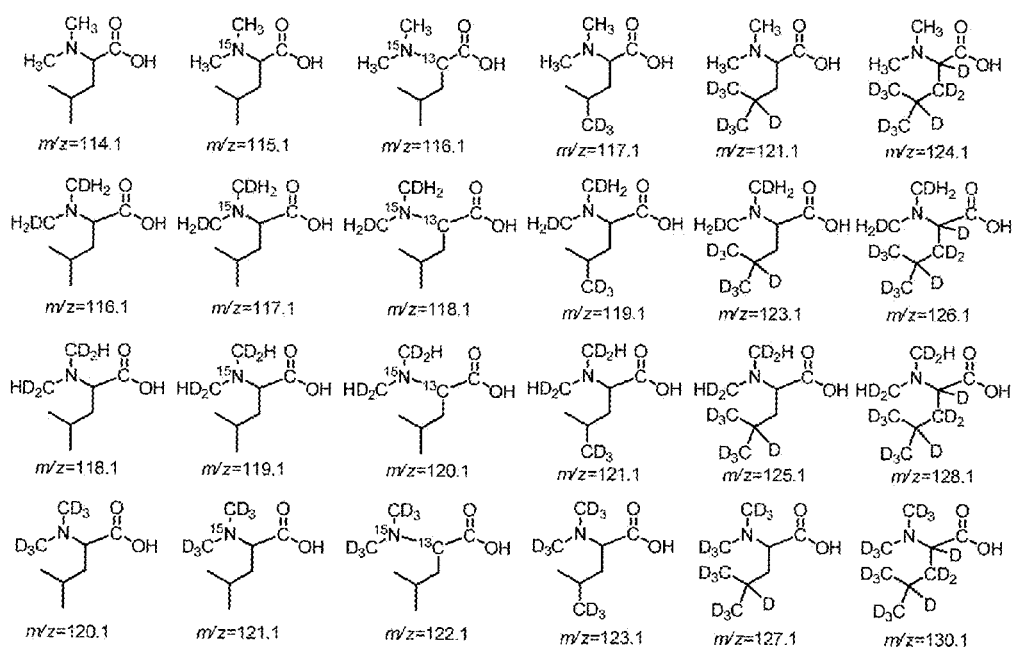
FIG. 2 shows various isotopic dimethylated leucines and the masses of the resulting $MS^2$ reporter ions (m/z).
Figure 4:
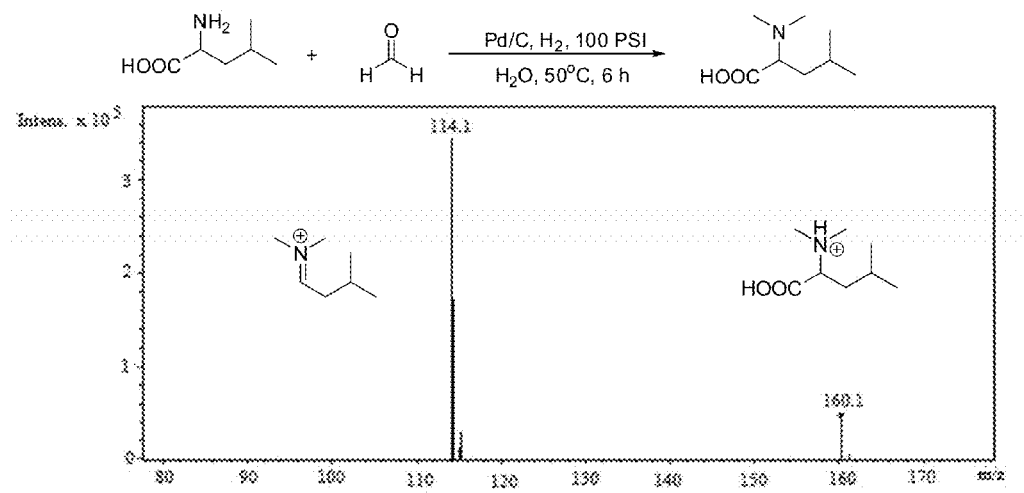
FIG. 4 shows synthesis steps used to form dimethylated leucine and a Quadrupole Time-of-Flight (QTOF) $MS^2$ spectrum of the dimethylated leucine showing the presence of the immonium reporter ion.
Figure 5:
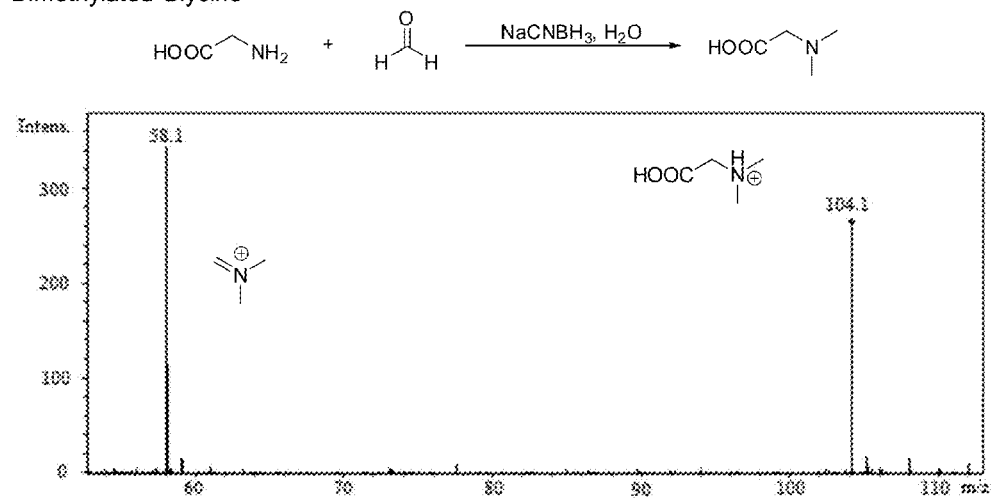
FIG. 5 shows synthesis steps used to form dimethylated glycine and a QTOF $MS^2$ spectrum of the dimethylated glycine showing the presence of the immonium reporter ion.
Figure 6:
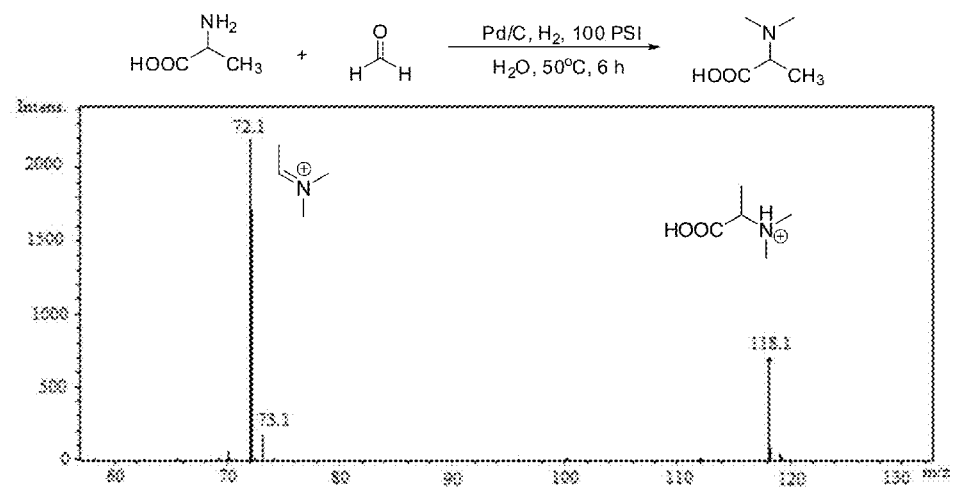
FIG. 6 shows synthesis steps used to form dimethylated alanine and a QTOF $MS^2$ spectrum of the dimethylated alanine showing the presence of the immonium reporter ion.
Figure 7:
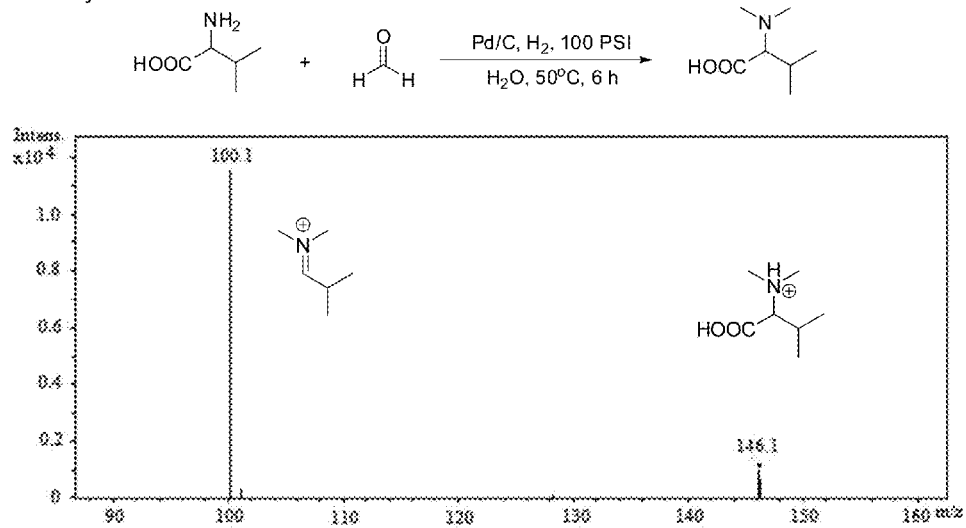
FIG. 7 shows synthesis steps used to form dimethylated valine and a QTOF $MS^2$ spectrum of the dimethylated valine showing the presence of the immonium reporter ion.
Figure 8:
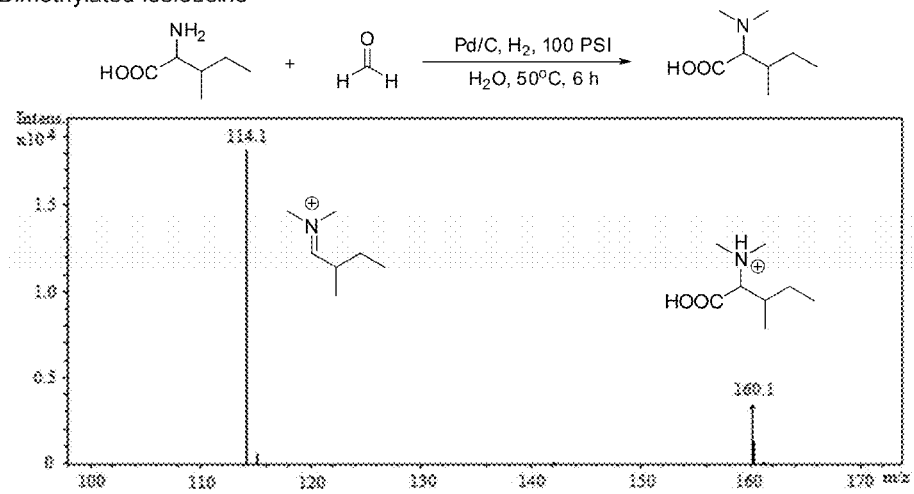
FIG. 8 shows synthesis steps used to form dimethylated isoleucine and a QTOF $MS^2$ spectrum of the dimethylated isoleucine showing the presence of the immonium reporter ion.
Figure 9:
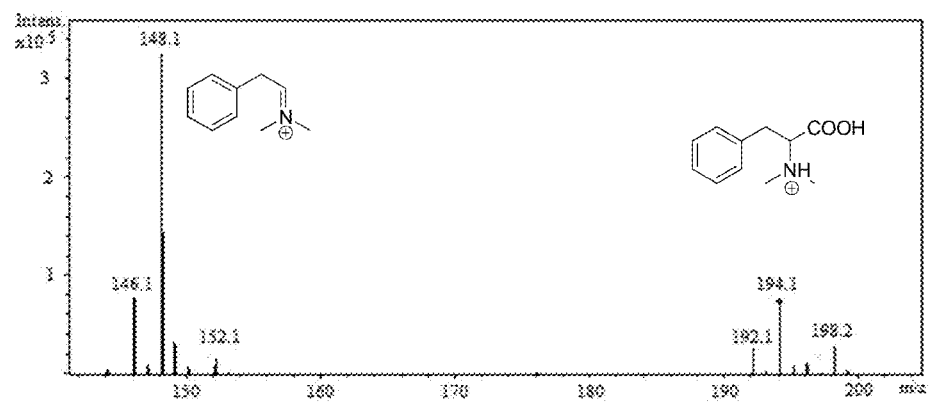
FIG. 9 shows synthesis steps used to form dimethylated phenylalanine and a QTOF $MS^2$ spectrum of the dimethylated phenylalanine showing the presence of the immonium reporter ion.

Isotopic dimethylated leucines can readily be made from commercially available leucine compounds. Different possible reporter ions and their corresponding mass (m/z) from isotopic dimethylated leucines are shown in FIG. 2. Similar reporter ions are also available for other dimethylated amino acids. The incorporation of other dimethylated amino acids into the tagging reagents is also useful since several amino acids are able to form strong immonium ions during fragmentation (see FIG. 3). For example, FIGS. 4-9 show synthesis steps used to form exemplary dimethylated amino acids and QTOF $MS^2$ spectra of those dimethylated amino acids showing the presence of the immonium reporter ions.

Figure 10:
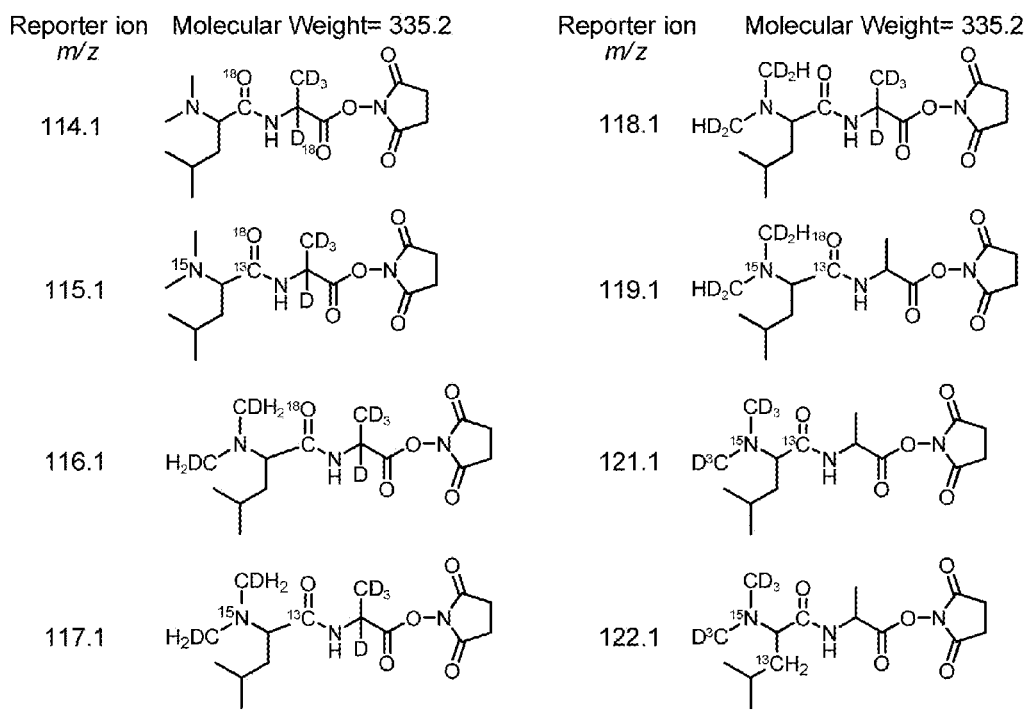
FIG. 10 shows different isotope combinations of isobaric dimethylated leucine-alanine (DiLeuAla) 8-plex tagging reagents.
Figure 11:
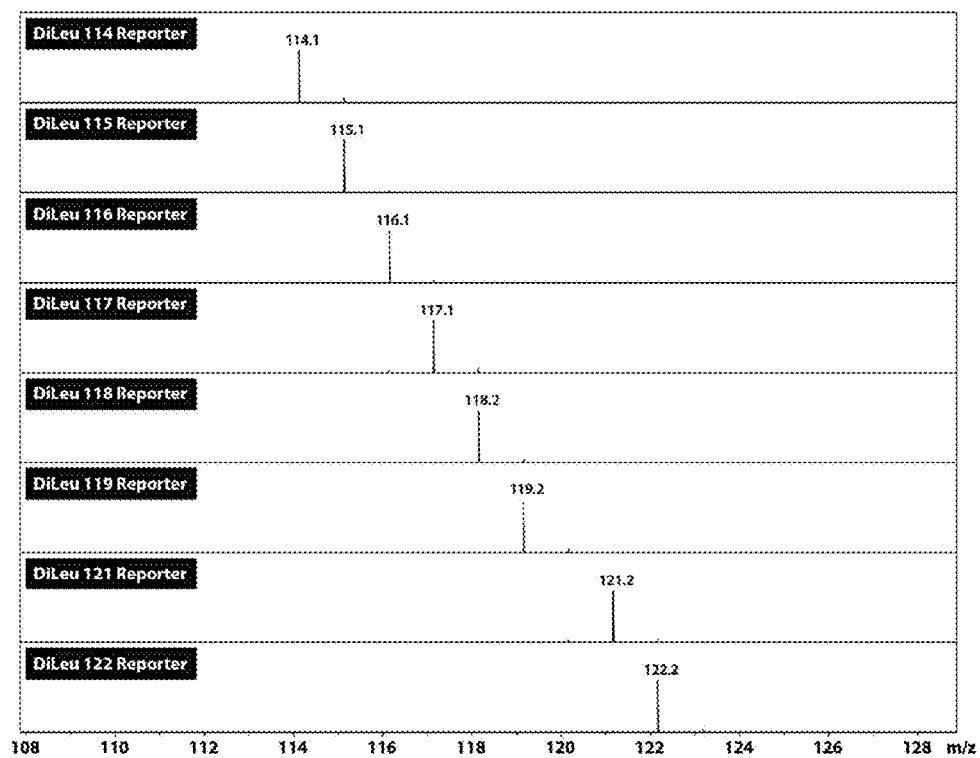
FIG. 11 shows QTOF $MS^2$ spectra of eight dimethylated leucine immonium ion reporter groups formed during fragmentation of the tagging reagents of FIG. 10.

With the general 8-plex reagent structure, instead of four reporter ions for four samples, eight reporter ions can be used to double the throughput. Introducing 8 or more mass differences to the same analyte allows 8 or more different concentrations of the same analyte to be detected in a single LC/MS run. The four reporter ions produced from the previous 4-plex dimethyl leucine tagging reagents (m/z 115.1, 116.1, 117.1, and 118.1) were extended to eight reporter ions (m/z 114.1, 115.1, 116.1, 117.1, 118.1, 119.1, 121.1, and 122.1) by incorporating different numbers of stable isotopes (deuterium, $^{13}C$, $^{15}N$, and $^{18}O$) in an alanine based balancing group. The chemical structure and isotopic combinations and reporter ion m/z of all eight of these reagents are shown in FIG. 10, and the QTOF $MS^2$ spectra of the dimethylated leucine immonium ion reporter groups are shown in FIG. 11.

In addition, the 8-plex reagents provide increased quantitation accuracy and a wider quantitation dynamic range. A common problem for quantitation with 4-plex reagents using reporter ions which are only 1 Da apart is the interference from adjacent isotopic peaks. Oftentimes, a mathematic algorithm is needed to achieve accurate quantitation, as is the case with the 4-plex reagents. In contrast, 8-plex and 16-plex reagents will offer a 2 Da separation between reporter ions if used in a 4-plex manner. This mitigates the isotope interferences present with 1 Da difference reporter ions thereby eliminating the need for complex mathematical processing in isobaric quantitative experiments.

Besides multiplex quantitation, the 8-plex and 16-plex dimethylated amino acid tags also promote enhanced fragmentation, thereby allowing more confident protein identification from tryptic peptides and de novo sequencing of neuropeptides and metabolites.

The isobaric tagging reagents of the present invention can generally be synthesized in simple three or four step synthesis. The ease of synthesis provides high yields lowering the cost as compared to other commercially available reagents. For example, 4-plex iTRAQ utilizes a 5 step synthesis with yields around 61%, and TMT requires a 14 step synthesis with yields around 1%. Data shows a high labeling efficiency using isobaric tagging reagents of the present invention for a number of peptides. Additionally, less tagging labels were cleaved from labeled peptides as compared to iTRAQ during MS analysis leading to a more complete peptide map which improves the accuracy of peptide identification. The ease of synthesis allows the synthesis of tagging reagents with varying numbers of isotopes (primarily deuterium). Because each tagging reagent would produce a reporter group having a unique molecular weight, each differently labeled molecule is able to be detected and relatively quantified by tandem mass spectrometry. It is believed using these different labels in a single experiment would act like multiple standards. The quantities of labeled molecules can be calculated from a standard curve created using the different amounts of the different isotopically labeled molecules. Instead of having to run multiple different analyses, the same information can be gleaned from a single experiment.

The development and application of a set of novel N,N-dimethylated amino acid 8-plex and 16-plex isobaric tandem mass ($MS^2$) tagging reagents with high quantitation efficacy and greatly reduced cost for neuropeptide, protein and small molecule analysis are described below. These tagging reagents resemble the general structure of a tandem mass tag in that it contains an amine reactive group (for example, triazine ester) targeting the N-terminus and ε-amino group of the lysine side chain of a peptide, a balance group, and a reporter group. All labeling reagents are readily synthesized from commercially available chemicals with greatly reduced cost.

EXAMPLES

Example 1

General Synthesis of Dimethylated Leucine 8-plex Reagents

All reagents were purchased from Sigma-Aldrich Chemical Company.

As illustrated in Schemes 4 and 5 presented below, synthesis of the 8-plex tagging reagents of the present invention involves coupling a dimethylated amino acid, dimethylated leucine (1) in this example, with an amino acid-benzyl ester hydrochloride, alanine benzyl ester hydrochloride (2) in this example, to yield dimethylated leucine alanine benzyl ester (3) followed by hydrogenation (4) and NHS ester activation (5). Different coupling agents as known in the art can be used to couple the dimethylated amino acid with the amino acid benzyl ester, such as DMTMM/NMM (Scheme 4) and EDC (Scheme 5). Alternative activation steps can also be employed as illustrated in Schemes 4 and 5.

Scheme 4 - General synthesis route of 8-plex reagent

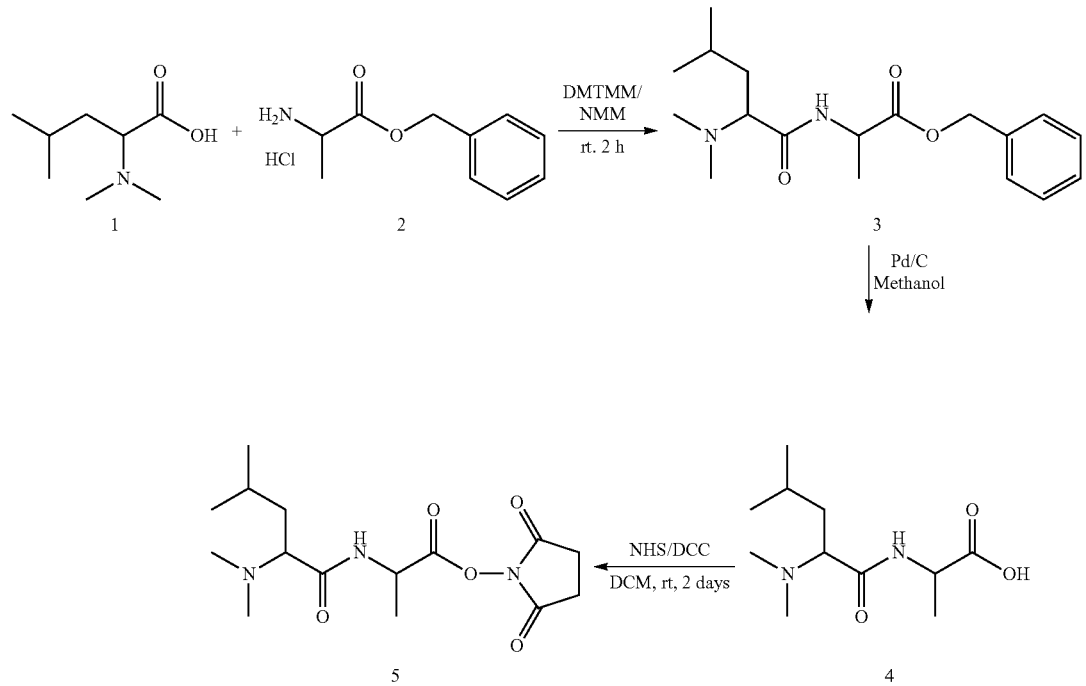

Scheme 5 - Alternate general synthesis route of 8-plex reagent

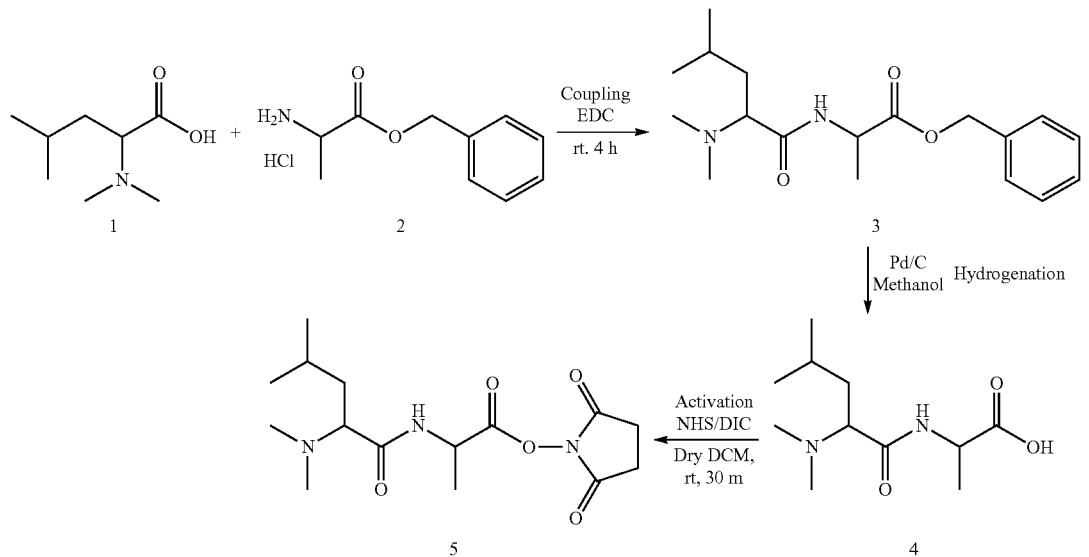

Figure 12:
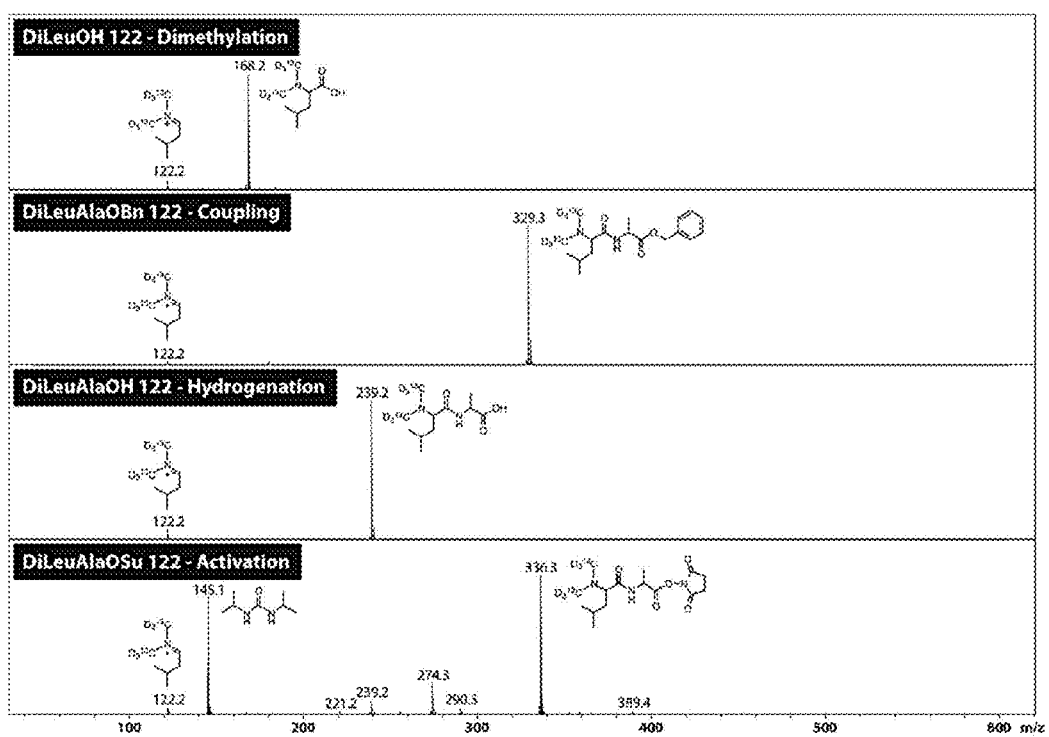
FIG. 12 shows QTOF MS spectra of products after the dimethylation, coupling, hydrogenation and activation steps used for making a dimethylated leucine-alanine tagging reagent.

FIG. 12 shows QTOF MS spectra validating products at each of the above synthetic steps: (1) dimethylated leucine, (3) coupling of dimethylated leucine and alanine benzyl ester to form DiLeuAlaOBn, (4) hydrogenation of DiLeuAlaOBn to form DiLeuAlaOH, (5) activation of DiLeuAlaOH to form DiLeuAlaOSu (NHS ester). The isobaric tagging reagent having a reporting group having a molecular mass of 122 was used as a representative example as shown in FIG. 12.

Example 2

Synthesis of Isotopic HCl.NH$_2$-Ala-OBn (2)

The general scheme for synthesizing alanine benzyl ester HCl (2) is shown in Scheme 6 below, which is adapted from Guo, et al., J. Am. Chem. Soc. 2009, 131. 16018-16020.

Scheme 6

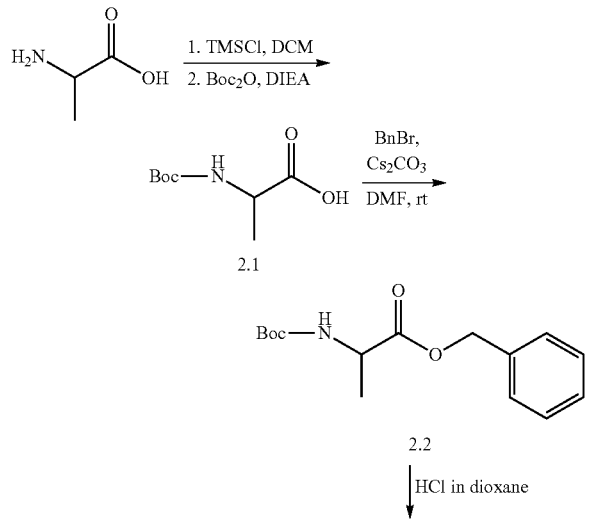

-continued

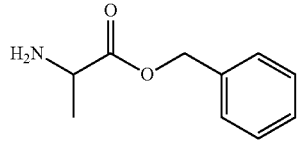

Boc-D4 Ala-OH (2.1). One gram D4 alanine (10.7 mmol) was suspended in anhydrous CH$_2$Cl$_2$ (20 mL) and stirred vigorously. Trimethylchlorosilane (TMSCl, 3 mL, 23.6 mmol, 2.2 times excess to alanine) was added in one portion and stirred at room temperature for 2 h. The mixture was cooled to 0° C., and N,N-diisopropylethylamine (DIEA, 3.35 mL, 19.26 mmol, 1.8 times excess to alanine) and Boc$_2$O (3.5 g, 16.05 mmol, 1.5 times excess) were added sequentially. The reaction was allowed to proceed to room temperature and stirred for overnight. The resulting mixture was concentrated to provide an oily looking mixture which was then dissolved in EtOAc (100 mL). To this mixture, water was added (40 mL), and the solution was acidified with 1 N HCl. The separated organic layer was dried (MgSO$_4$), filtered and concentrated to give a white solid. The desired Boc protected product was purified via column chromatography eluting with EtOAc/hexane (1:10 to 1:1; v/v) to give pure product.

Boc-Ala-OBn (2.2). Boc protected alanine and same molar ratio Cs$_2$CO$_3$ were dissolved in DMF (10-20 mL). Benzyl bromide (1.2 times molar excess to alanine) was added. The mixture was stirred at the room temperature for overnight. The mixture was diluted with ethyl acetate (50-100 mL) and washed with saturated aqueous NaHCO$_3$ and brine. The organic layers were collected, dried over MgSO$_4$ and filtered. The filtrate was concentrated to give the crude product, which was purified via column chromatography eluting with EtOAc/hexane to give the desired benzyl ester.

NH$_2$-Ala-OBn HCl (2). Boc-Ala-OBn was dissolved in 4N HCl in dioxane (10 mL) and stirred for three hours at room temperature. The solvent was blown off under a stream of N$_2$. The residue was placed under high vacuum for one hour. Re-dissolved in CH$_2$Cl$_2$ (50 mL) and rotovap dry. Repeat the drying circle for three times till the white powder forms.

Example 3

Synthesis of DiLeu-Ala-OBn (3)

Compound 1 from Scheme 4 (175 mg, 1.1 mmol) was mixed with (326 mg, 1.18 mmol) 4-(4,6-Dimethoxy-1,3,5-triazin-2-yl)-4-methylmorpholinium chloride (DMTMM) and 390 μL (3.54 mmol) N-methylmorpholine (NMM) and compound 2 (216 mg, 1 mmol) in 10 mL of N,N-dimethylformamide (DMF). Reaction mixture was stirred at room temperature for 3-4 h till the solution became clear. Reaction completeness was monitored by thin-layer chromatography (TLC). Upon reaction completion, 100 mL of ethyl acetate (EtOAC) was added to the reaction mixture followed by 20 mL of saturated aqueous $NaHCO_3$ and brine wash three times to pre-purify compound 3. Compound 3 was further purified by flash column chromatography (hexane/EtOAc). Alternatively, synthesis of compound 3 can be achieved using EDC as shown in Scheme 5.

Example 4 of DiLeu-Ala (4)

Compound 3 (320 mg, 1 mmol) was dissolved in 20 mL of methanol and stirred with a suspension of 10% Pd/C (320 mg) in a round bottom flask (50 mL capacity) at room temperature under atmosphere pressure hydrogen for 12 h. Reaction suspension was filtered and evaporated.

Example 5

Synthesis of DiLeu-Ala NHS Ester (5)

Compound 4 (115 mg, 0.50 mmol) was added to the mixture of NHS (59 mg, 0.51 mmol) and DCC (113 mg, 0.55 mmol) in 10 mL DCM. The reaction mixture was stirred for 2 days at room temperature and insoluble solid was filtered out. The filtrate was dried by rotorvap. Alternatively, activation of Compound 4 to form DiLeu-Ala NHS Ester (5) can be achieved using NHS/DIC as shown in Scheme 5. While the above examples illustrate formation of dimethylated leucine alanine, the above methodology can also be used to synthesize sets of isobaric 8-plex reagents using other amino acids.

Example 6

Protocol for Peptide Labeling

Ten μL of neuropeptide standard bradykinin ($10^{-5}$M) was dried and reconstituted in 10 μL of EtOH. The prepared sample solution was labeled by 20 μL of activated labeling solution at room temperature for 1 h with vortexing.

The labeled bradykinin was dried, reconstituted in 100 μL of 0.1% FA water solution and subjected for QTOF direct infusion to acquire the labeled peptide tandem mass spectrum. The flow rate used for direct infusion was 0.3 μL/min.

Example 7

Discussion of Synthesis Steps and Potential Alternatives

There are multiple steps involved in the synthesis of the dimethylated amino acid 8-plex reagents. With regard to Scheme 4 described above, the hydrogenation reaction of dimethylated leucine alanine benzyl ester yields almost quantitative conversion. The two bottlenecks of the current synthesis schemes are: the synthesis of dimethylated leucine alanine benzyl ester (3) and its activated NHS ester (5) purification. N-α-Methylation causes additional steric hindrance during coupling and it should be noted that N,N-methylated amino acids are bulkier than their unsubstituted counterparts. The alkylated amino component may be more basic, but the slight gain in reactivity is more than outweighed by the additional steric hindrance. Therefore, highly efficient activating reagents and protocols may be required for obtaining satisfactory conversion.

The current dimethylated leucine and alanine benzyl ester coupling step using DMTMM/NMM in Scheme 4 results in less than 40% yield. Accordingly, optimization of the coupling condition can help increase the overall yield of the DiLeu 8-plex synthesis. Besides the DMTMM/NMM coupling system, several coupling reagents which have been successfully employed for coupling to N-α-methylated amino acids may improve the coupling efficiency, such as EDC shown in Scheme 5 (F. Albericio, et al., J. Org. Chem. 1998, 63. 9678-9683; L. A. Carpino, A. El-Faham, J. Am. Chem. Soc. 1995, 117. 5401-5402; 8. J. Coste, et al., J. Org. Chem. 1994, 59. 2437-2446; and E. Falb, et al., J. Pept. Res. 1999, 53. 507-517).

An alternative to the liquid phase synthesis would be the solid phase synthesis (R. B. Merrifield, J. Am. Chem. Soc. 1963, 85. 2149-2154). Briefly, 9-fluorenylmethyloxycarbonyl group (Fmoc) protected alanine is bound to a solid phase resin, forming a covalent bond between the carbonyl group and the resin. Then the alanine amino group is de-protected and coupled to the carboxyl group of the dimethylated leucine. After coupling, the target molecule can be obtained by cleaving the product from the resin (illustrated in Scheme 7). Both the amino acid resin loading step and amino acid coupling step require four times excess amount of amino acid to the resin loading capacity. The advantages of solid phase synthesis of our reagents are that all eight reagents can be synthesized simultaneously and minimum labor is needed.

Scheme 7-Solid phase peptide synthesis (SPPS) of Ala-DiLeu reagent

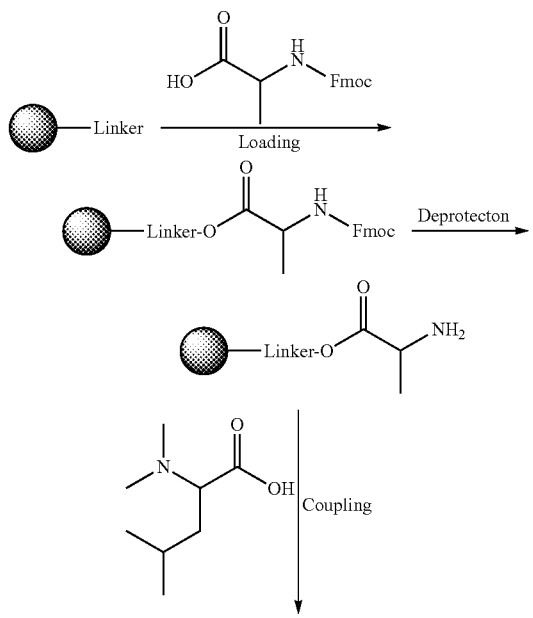

-continued

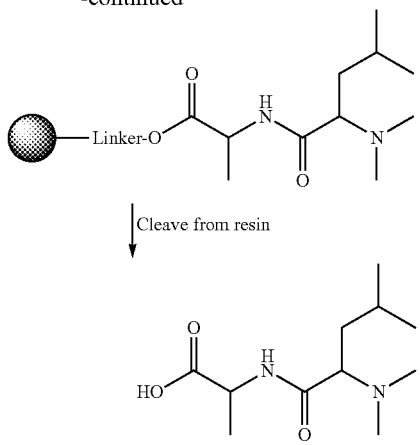

Purified DiLeu 8-plex NHS ester is crucial for accurate quantitation. Initial attempt of purifying DiLeu 8-plex NHS ester by diisopropyl ether re-crystallization was not successful. This was largely due to the small amount of DiLeu 8-plex reagent synthesized in the initial experiment, resulting from the low reaction yield of DiLeu and alanine benzyl ester coupling. Enhancing the coupling reaction efficiency is the key to successful purification of activated DiLeu 8-plex NHS ester.

Example 8

Discussion of Peptide Labeling and Quantitation

Figure 13:
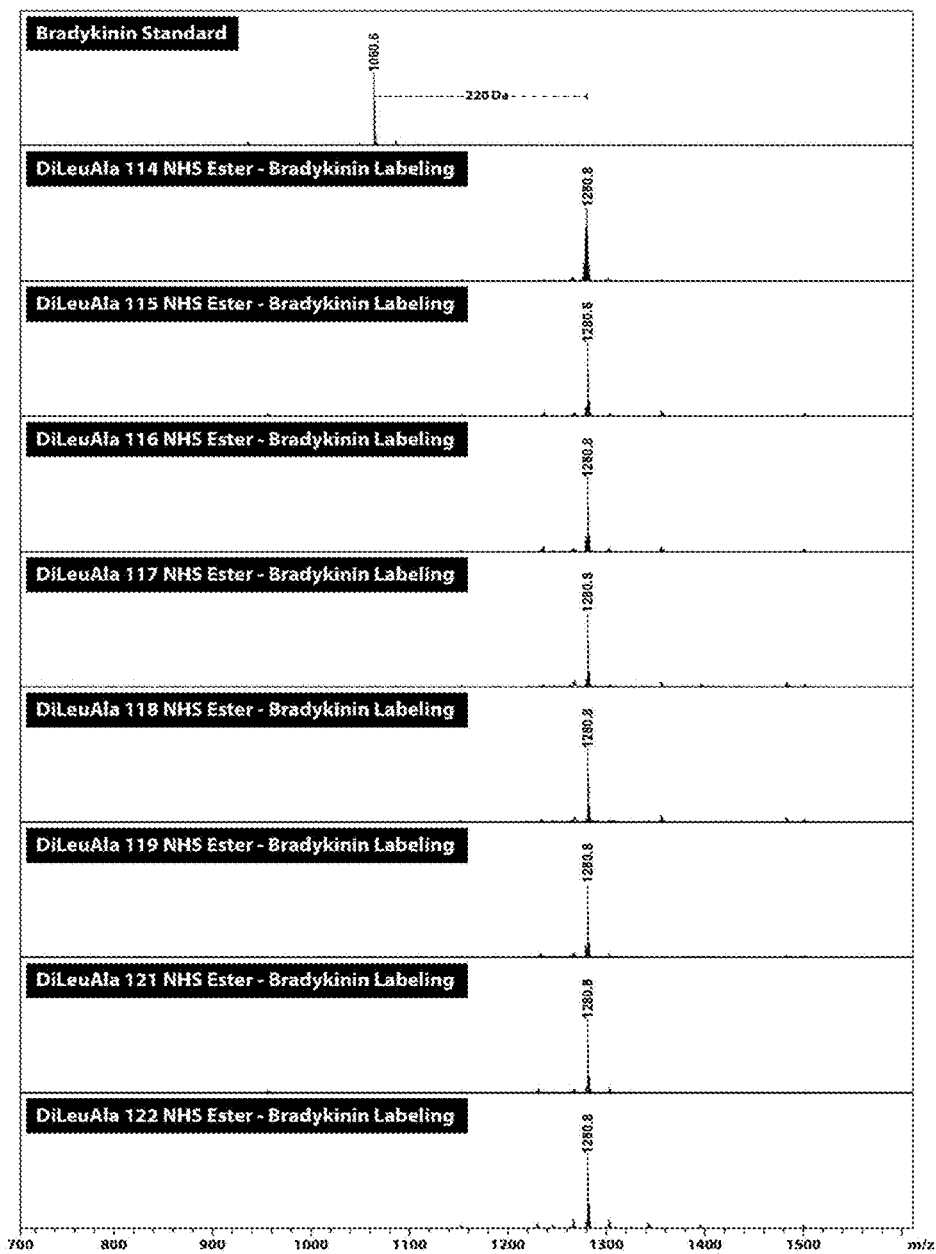
FIG. 13 shows MALDI-TOF MS spectra of a bradykinin neuropeptide standard (1060.6 Da) labeled with activated isobaric 8-plex DiLeuAla tagging reagents yielding a 220 Da mass shift. Complete labeling was observed after 2 hours.

In an initial labeling reaction, isotopically labeled DiLeuAla tagging reagents, as shown in FIG. 10, were used to label the neuropeptide standard bradykinin (RPPGFSPFR), resulting in a 220 Da mass shift:

FIG. 13 shows MALDI-TOF MS spectra of the bradykinin neuropeptide standard labeled with the activated isobaric 8-plex DiLeuAla tagging reagents resulting in a consistent 220 Da mass shift for each tagging reagent. Complete labeling was observed after 2 hours.

Figure 14:
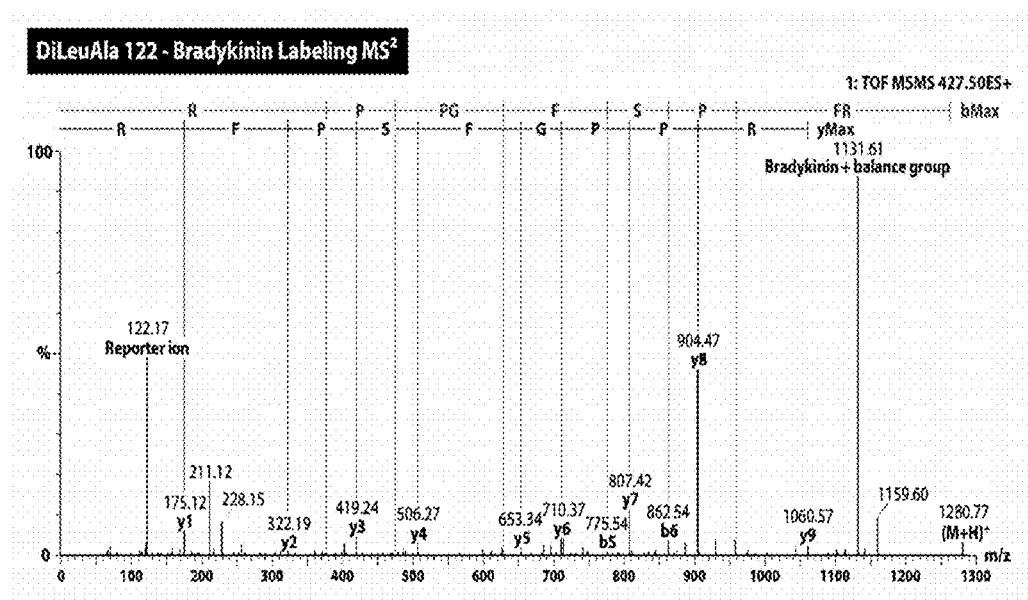
FIG. 14 shows a QTOF $MS^2$ spectrum of the bradykinin neuropeptide standard labeled with a DiLeuAla 122 tagging reagent. Complete peptide backbone cleavage y-ions are observed for structural identification as well as a strong 122 immonium ion observed for quantitation.

During fragmentation, the reporter group from each tagging reagent will form a detectable immonium ion which can then be used for quantitation. FIG. 14 shows QTOF $MS^2$ spectrum of the bradykinin neuropeptide standard labeled with an isotopically labeled DiLeuAla tagging reagent having a reporter group with a molecular mass of 122. Complete peptide backbone cleavage y-ions are observed for structural identification as well as a strong 122 immonium ion.

Figure 15:
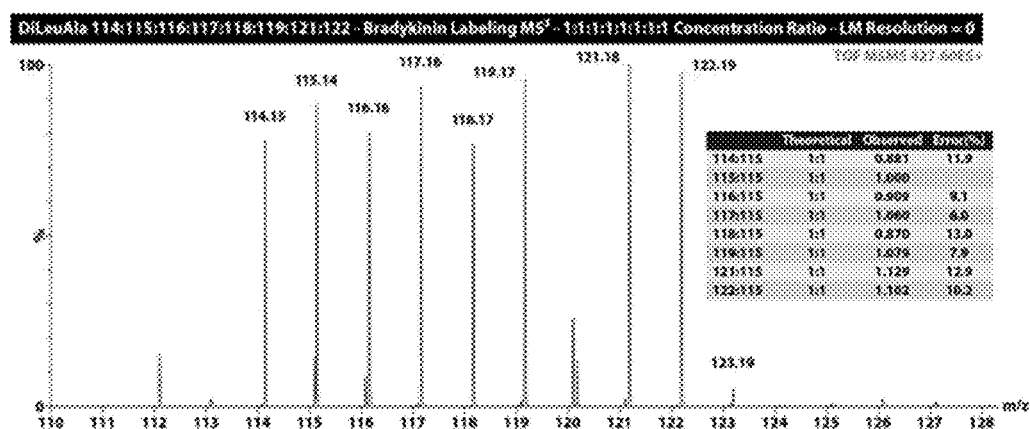
FIG. 15 shows a QTOF $MS^2$ spectrum of the reporter ion region of the bradykinin neuropeptide standard labeled with the isobaric 8-plex DiLeuAla tagging reagents of FIG. 10 combined into a single mixture at a 1:1:1:1:1:1:1:1 concentration ratio. The observed ratio is calculated for each tagging reagent in relation to the tagging reagent having the reporter ion mass of 115 along with the absolute value of the percent error from 1:1.

During quantitation, the samples labeled by each tagging reagent can be combined into a single mixture in known ratios and the amounts of each sample calculated by the relative peak size from the $MS^2$ scans. For example, FIG. 15 shows a QTOF $MS^2$ spectrum of the reporter ion region of the bradykinin neuropeptide standard labeled with the isobaric 8-plex DiLeuAla tagging reagents of FIG. 10 combined into a single mixture at a 1:1:1:1:1:1:1:1 concentration ratio. The observed ratio is calculated for each tagging reagent in relation to the tagging reagent having the reporter ion mass of 115 along with the absolute value of the percent error from 1:1.

Figure 16:
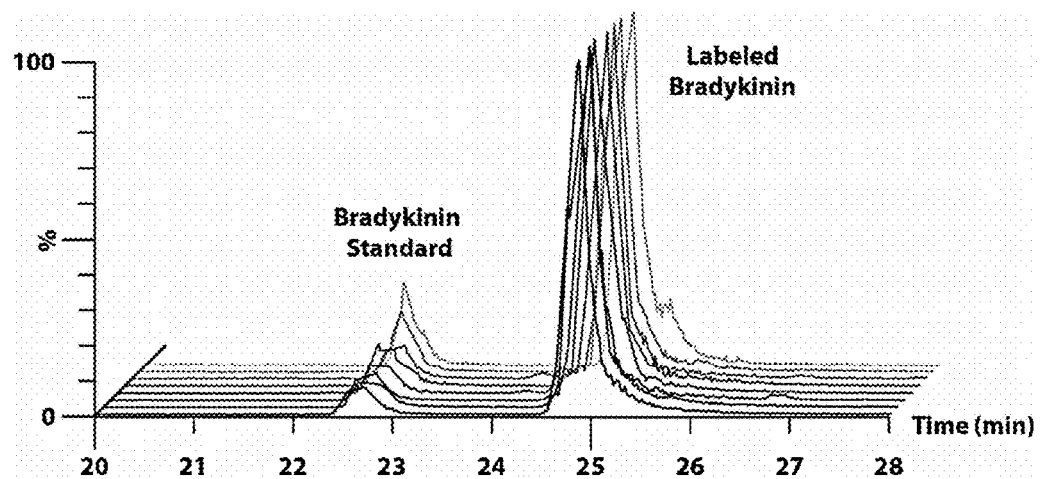
FIG. 16 shows the chromatographic retention time of the bradykinin neuropeptide standard labeled with the isobaric 8-plex DiLeuAla tagging reagents of FIG. 10. Each chromatogram is offset by 45° for clarity, with the bradykinin labeled with the tagging reagent having the reporter ion mass of 122 in front and the bradykinin labeled with the tagging reagent having the reporter ion mass of 114 in the back.

FIG. 16 shows the NanoUPLC base-peak chromatograms of mixtures of the unlabeled bradykinin peptide standard and the bradykinin neuropeptide standard labeled with the isobaric 8-plex DiLeuAla tagging reagents of FIG. 10. Each chromatogram is offset by 45° for clarity, with the bradykinin labeled with the 122 tagging reagent in front and the bradykinin labeled with the 114 tagging reagent in the back. No significant retention time difference is observed between the eight labeled peptides.

Similar results were achieved using isobaric tagging reagents other than the DiLeuAla tagging reagents described above. For example, as shown in FIGS. 17a and 17b, a dimethylated leucine-glycine tagging reagent was synthesized similar to the DiLeuAla tagging reagents described above and resulted in a reporter ion having the same molecular mass. Additionally, a dimethylated leucine-glycine tagging reagent, dimethylated glycine tagging reagent and dimethylated alanine tagging reagent were similarly used to successfully label the neuropeptide standard bradykinin (RPPGFSPFR):

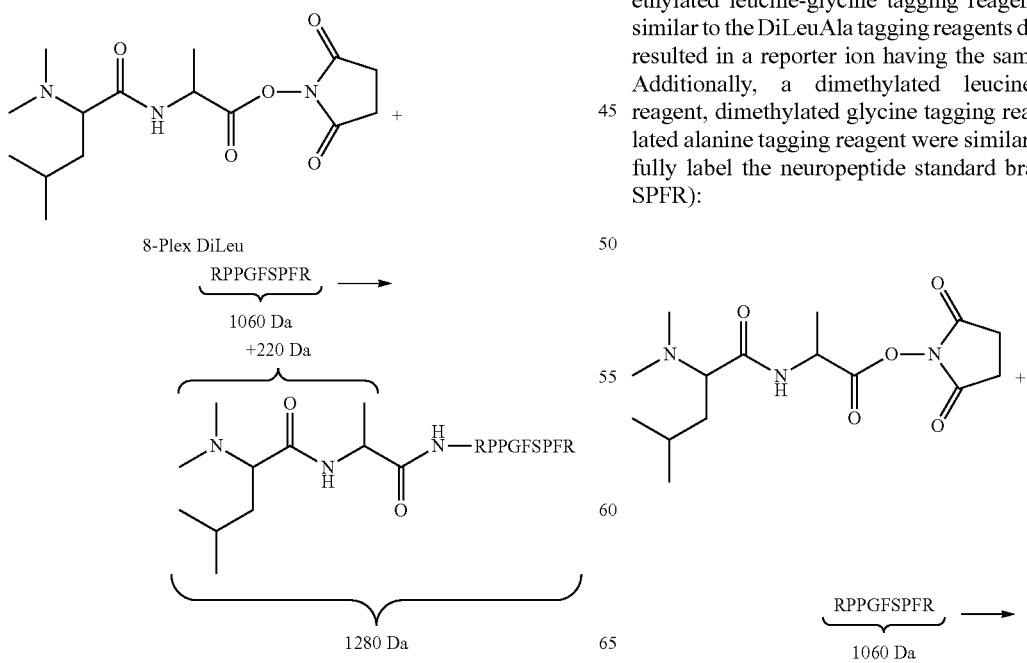

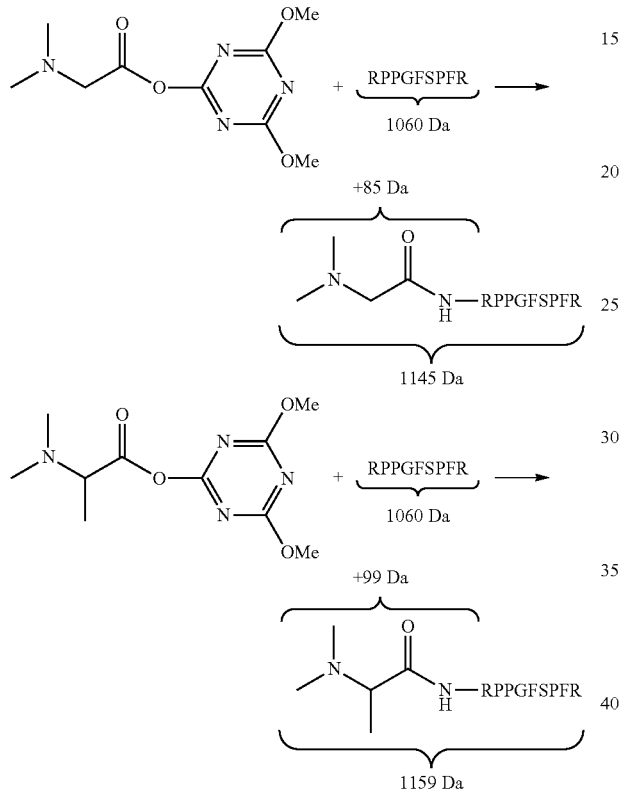

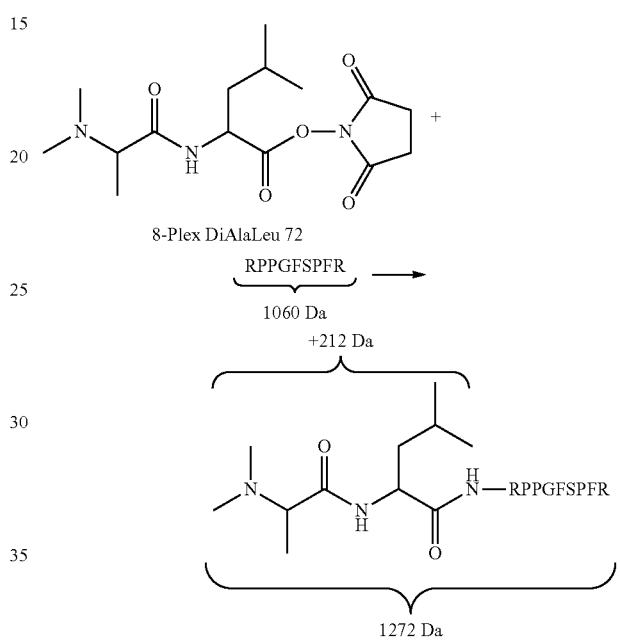

Figure 18:
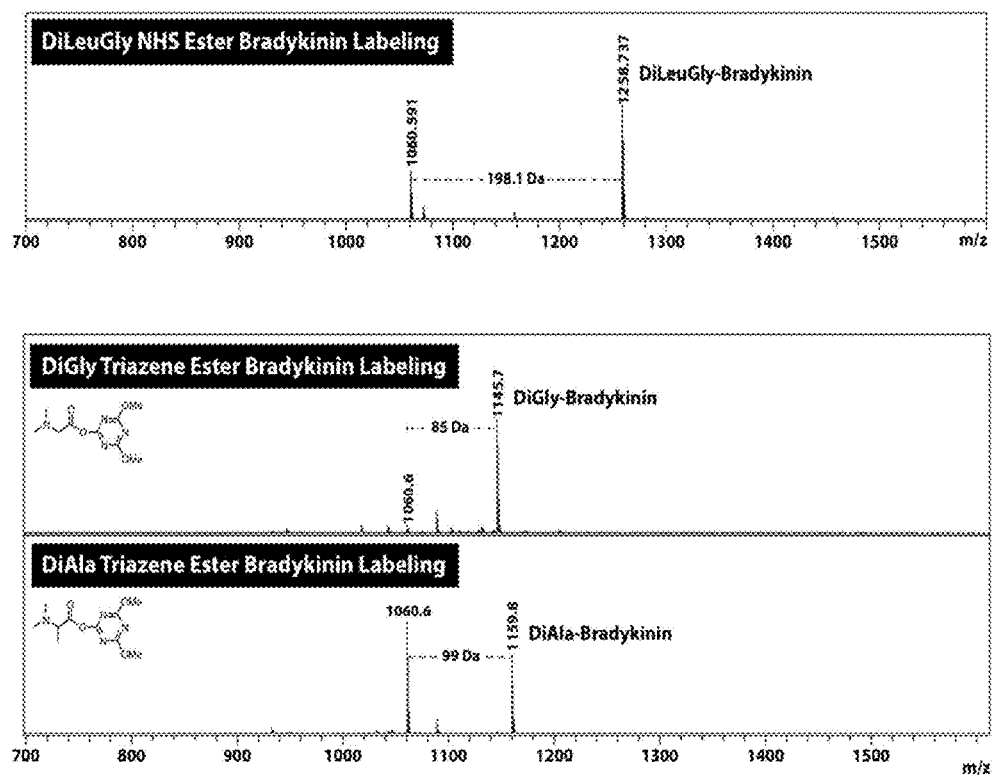
FIG. 18 shows MALDI-TOF MS spectrum of the bradykinin neuropeptide standard (1060.6 Da) labeled with: a dimethylated leucine-glycine tagging reagent resulting in a 198 Da mass shift; a dimethylated glycine tagging reagent resulting in a 85 Da mass shift; and a dimethylated alanine tagging reagent resulting in a 99 Da mass shift.

FIG. 18 shows a MALDI-TOF MS spectrum of the bradykinin neuropeptide standard labeled with the dimethylated leucine-glycine tagging reagent resulting in a 198 Da mass shift; the dimethylated glycine tagging reagent resulting in a 85 Da mass shift; and the dimethylated alanine tagging reagent resulting in a 99 Da mass shift.

Example 9

Synthesis and Use of 16-plex Reagents

The preliminary data showed that the 8-plex tagging reagents of the present invention can be used to label peptides resulting into detectable reporter ions during fragmentation. The above methodology for dimethylated leucine-alanine 8-plex reagents can also be used to synthesize sets of isobaric 8-plex reagents using other amino acids. Furthermore, the additional set of 8-plex reagents can be achieved by simply switching the amino acids used in the reporter group and balance group.

Figure 19:
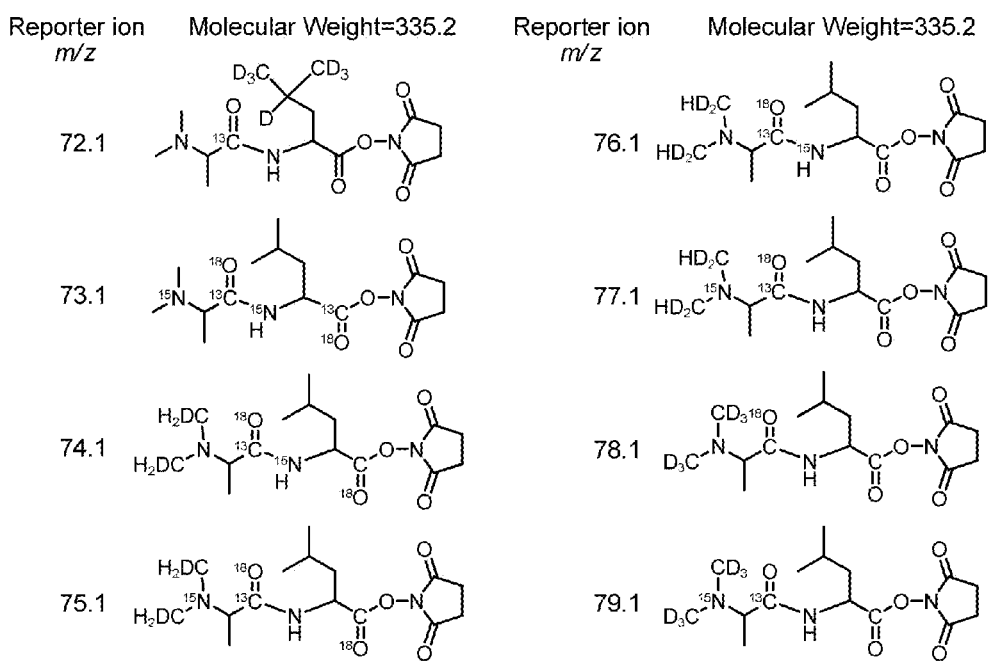
FIG. 19 shows the structure and different isotope combinations of isobaric dimethylated alanine-leucine 8-plex tagging reagents.
Figure 20:
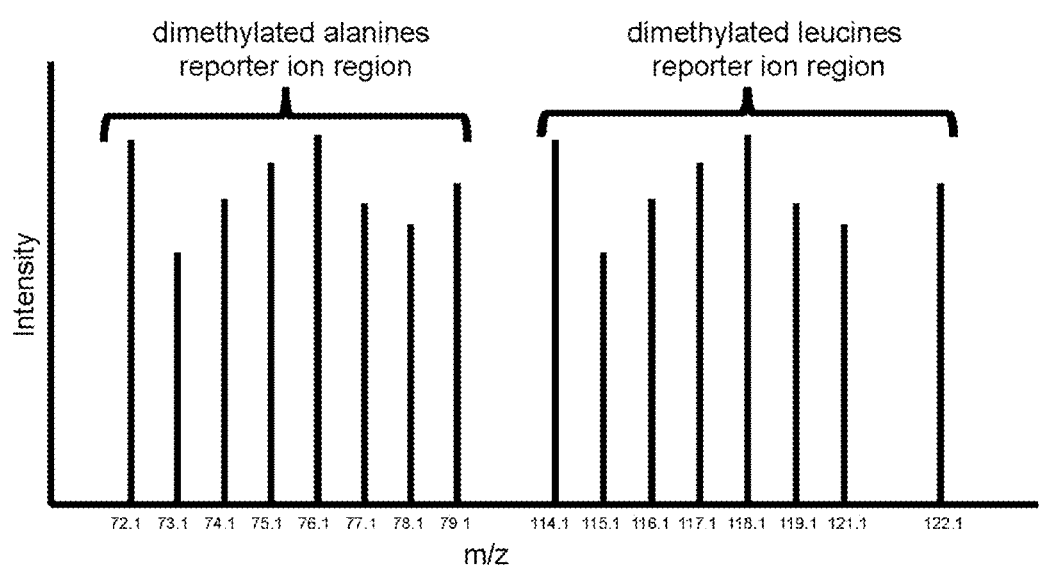
FIG. 20 illustrates the distribution of reporter ions for isobaric dimethylated leucine-alanine and dimethylated alanine-leucine 16-plex reagents.

FIG. 19 shows the chemical structure, isotope combinations and reporter ion m/z of the corresponding isotopic dimethylated alanine-leucine reagents. The reporter ions m/z are: 72.1, 73.1, 74.1, 75.1, 76.1, 77.1, 78.1 and 79.1. It is worth noting that the set of dimethylated alanine-leucine reagents have the same total molecular weight as the dimethylated leucine-alanine reagents. Combining these two sets of 8-plex isobaric reagents thus makes a set of 16-plex isobaric reagents for MS quantitation. The predicted distribution of reporter ions for this 16-plex set is illustrated in FIG. 20.

An activated light version of an 8-plex DiAlaLeu tagging reagent was used to label the bradykinin neuropeptide standard showing a 212 Da mass shift with the reporter group and balancing group (220 Da mass shift for the isobaric version):

The combination of isobaric 8-plex DiLeuAla and isobaric 8-plex DiAlaLeu, both of which feature the same isobaric mass for each label, would allow 16-plex quantitation in a single run.

Figure 21:
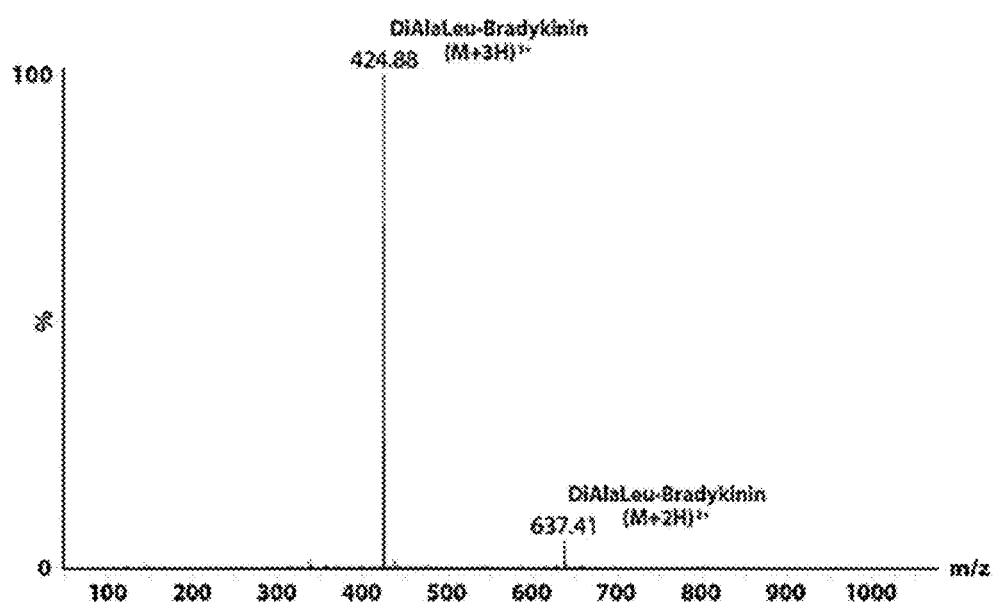
FIG. 21 shows a QTOF MS spectrum of the bradykinin neuropeptide standard labeled with a light version of the 8-plex DiAlaLeu. Observed are the 3+ and 2+ ions of the labeled bradykinin (1272 Da) at m/z 424.88 and 637.41, respectively.
Figure 22:
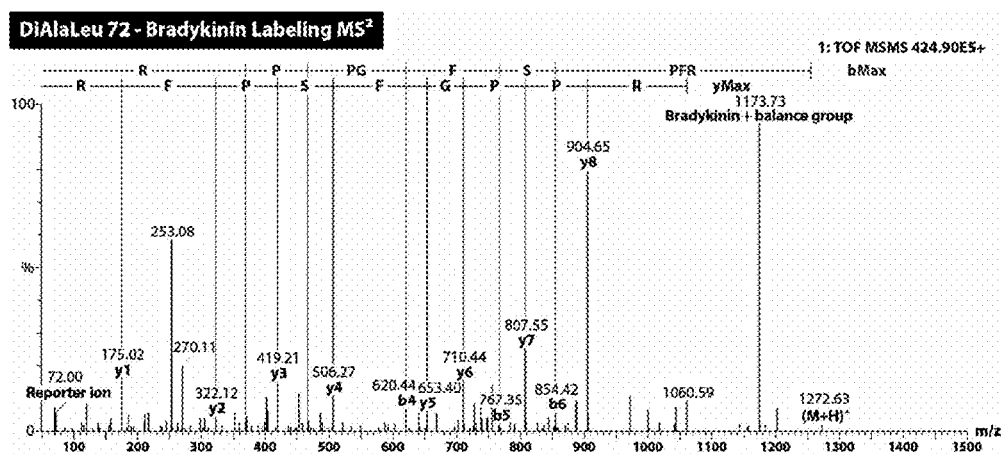
FIG. 22 shows a QTOF MS/MS spectrum of the bradykinin neuropeptide standard labeled with a light version of the 8-plex DiAlaLeu as a representative example. Complete peptide backbone cleavage of the y-ions is observed for structural identification. The immonium reporter ion for quantitation is observed at m/z 72 and a non-interfering proline immonium ion is observed nearby at m/z 70.

FIG. 21 shows a QTOF MS spectrum of the bradykinin neuropeptide standard labeled with a light version of the 8-plex DiAlaLeu (having a reporter ion at m/z 72). Observed are the 3+ and 2+ ions of the labeled bradykinin (1272 Da) at m/z 424.88 and 637.41, respectively. FIG. 22 shows a QTOF MS/MS spectrum of the bradykinin neuropeptide standard labeled with the 8-plex DiAlaLeu 72 as a representative example. Complete peptide backbone cleavage of the y-ions is observed for structural identification. The immonium reporter ion for quantitation is observed at m/z 72 and a non-interfering proline immonium ion is observed nearby at m/z 70

Accordingly, up to 16 different analytes could be tagged in a single experiment. Alternatively, these tagging reagents can be used to provide up to 4-plex and 8-plex tagging reagents whose reporter ions differ by two or more Daltons from one another. The two Dalton spacing allows for increased accuracy during MS analysis. For example, FIG. 23 shows QTOF MS² spectra of the reporter ion region of the bradykinin neuropeptide standard labeled with four of the isobaric DiLeuAla tagging reagents of FIG. 10 (m/z 427.6, 3+ charge) demonstrating a dynamic range advantage in 4-plex quantitation.

Figure 23:
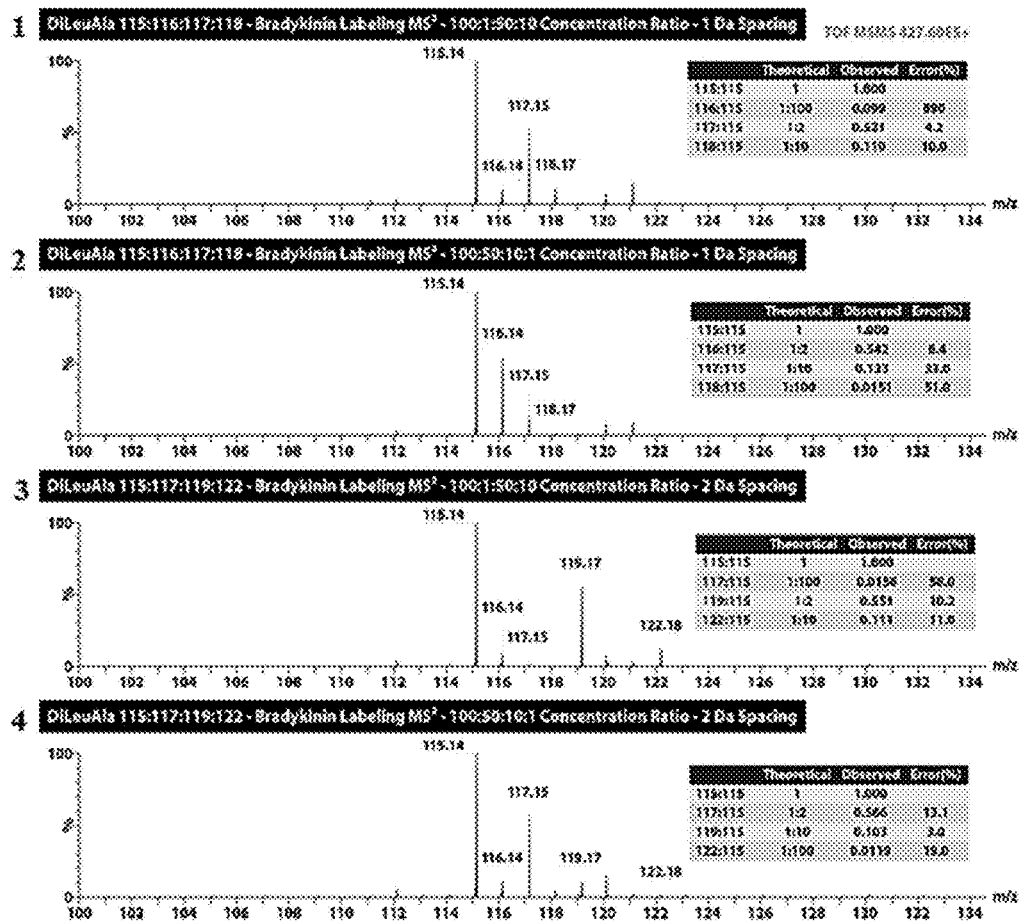
FIG. 23 shows QTOF $MS^2$ spectra of the reporter ion region of the bradykinin neuropeptide standard labeled with four of the isobaric DiLeuAla tagging reagents of FIG. 10 demonstrating 4-plex quantitation with either one- or two-Dalton tag spacing.

The first spectrum in FIG. 23 shows quantitation of a bradykinin mixture labeled with isobaric 8-plex DiLeuAla 115:116:117:118 in a ratio of 100:1:50:10. Using one-Dalton spacing, the 116 reporter peak, which is in a 1:100 ratio to the neighboring 115 reporter peak, is incorrectly observed as being in a 0.099 ratio to 115 rather than the expected ratio of 0.010. The isotopic peak of the 115 reporter that overlaps at m/z 116 masks the signal from the 116 reporter entirely in this case and results in inaccurate quantitation.

The third spectrum in FIG. 23 shows quantitation of a bradykinin mixture labeled with isobaric 8-plex DiLeuAla 115:117:119:122 in a similar ratio of 100:1:50:10. Using two-Dalton spacing, the 117 reporter peak, which is in a 1:100 ratio to the 115 reporter peak, is observed with a 58% error. This error can be attributed to the second isotopic peak of the 115 reporter that is present at m/z 117. The 117:115 ratio of 0.0158 observed with two-Dalton spacing of the tags is significantly more accurate than the 116:115 ratio of 0.099 observed with one-Dalton spacing of the tags.

The second spectrum in FIG. 23 shows quantitation of a bradykinin mixture labeled with isobaric 8-plex DiLeuAla 115:116:117:118 in a ratio of 100:50:10:1. Using one-Dalton spacing, the 118 reporter peaks displays a significant % error due to isotopic peak of the higher abundance 117 reporter peak. Likewise, the 117 reporter also displays a significant % due to the isotopic peak of the 116 reporter peak.

The fourth spectrum in FIG. 23 shows quantitation of a bradykinin mixture labeled with isobaric 8-plex DiLeuAla 115:117:119:122 in a similar ratio of 100:50:10:1. Using two-Dalton spacing, the 122 reporter peak in 1:100 ratio to the 115 reporter peak is observed with a 19% error (compared to the 51% error using one-Dalton spacing with the same ratios). Because the 122 reporter peak is free from the influence of isotopic peaks from neighboring reporter peaks, 4-plex quantitation using isobaric 8-plex DiLeuAla with two-Dalton spacing of the tags is shown to be accurate within a more acceptable error range.

Example 10

Figure 24:
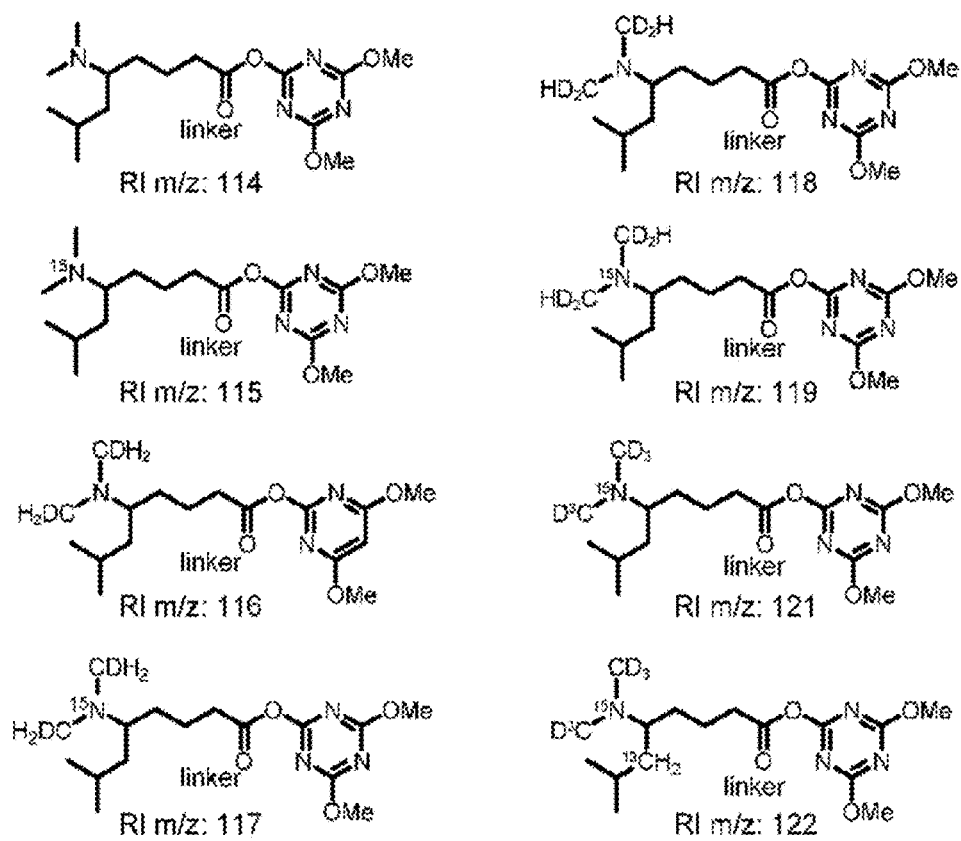
FIG. 24 shows a set of dimethylated leucine 8-plex reagents which do not contain an amino acid as part of the balancing group.

8-plex Tagging Reagents that do not Contain Standard Natural Amino Acid Derived Reporter Groups and Balancing Groups While it is preferable for the reporter and balancing group of the tagging reagents to contain standard natural amino acid as described above, it is also possible to provide 8-plex tagging reagents that use reporter and balancing groups which do not contain amino acids or contain amino acids which are not derived from standard natural amino acids. For example, FIG. 24 shows a set of dimethylated leucine 8-plex reagents which do not contain an amino acid as part of the balancing group. This can be permissible as long as the balancing group provides sufficient atoms able to be isotopically labeled in order to balance the isotopes in the reporter group and provide the same aggregate mass for each of the tagging reagents. In FIG. 24, the balancing group would have to contain multiple $^{13}C$ atoms and deuterium atoms to match the isotopes in the reporter group.

Figure 25:
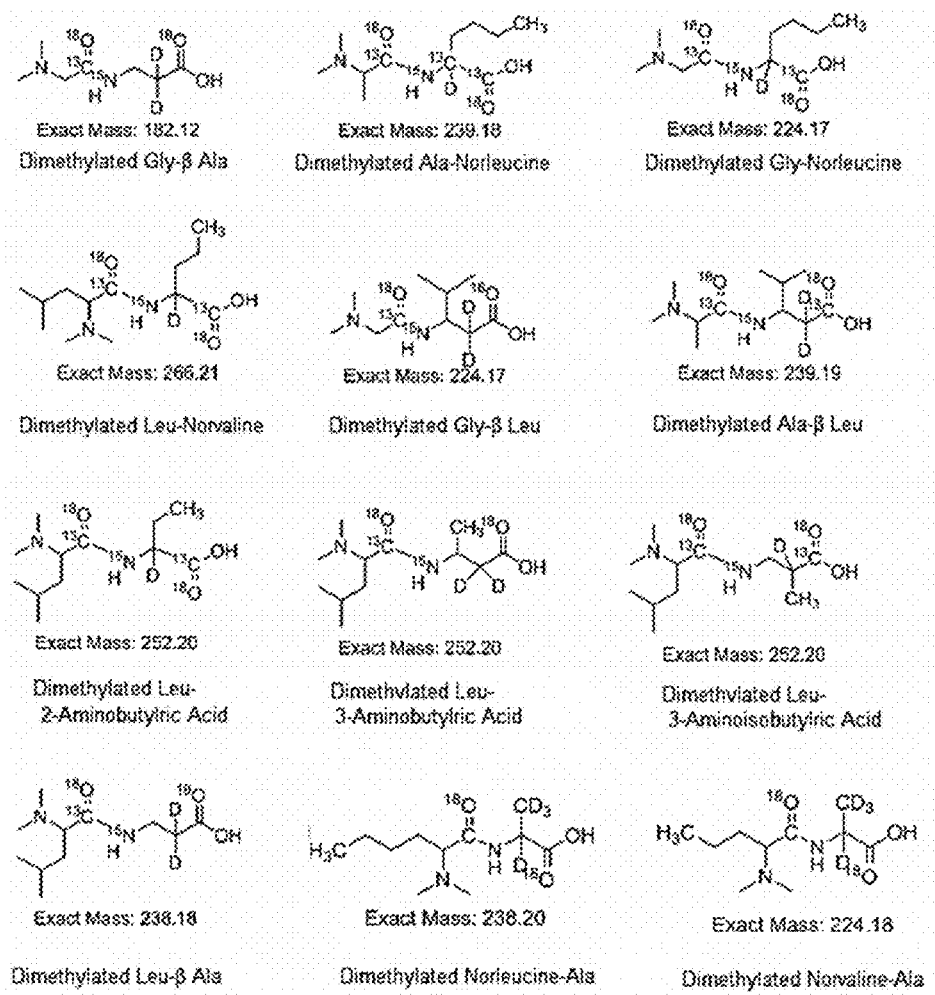
FIG. 25 shows exemplary tagging reagents which contain non-standard or synthetic amino acids.
Figure 26:
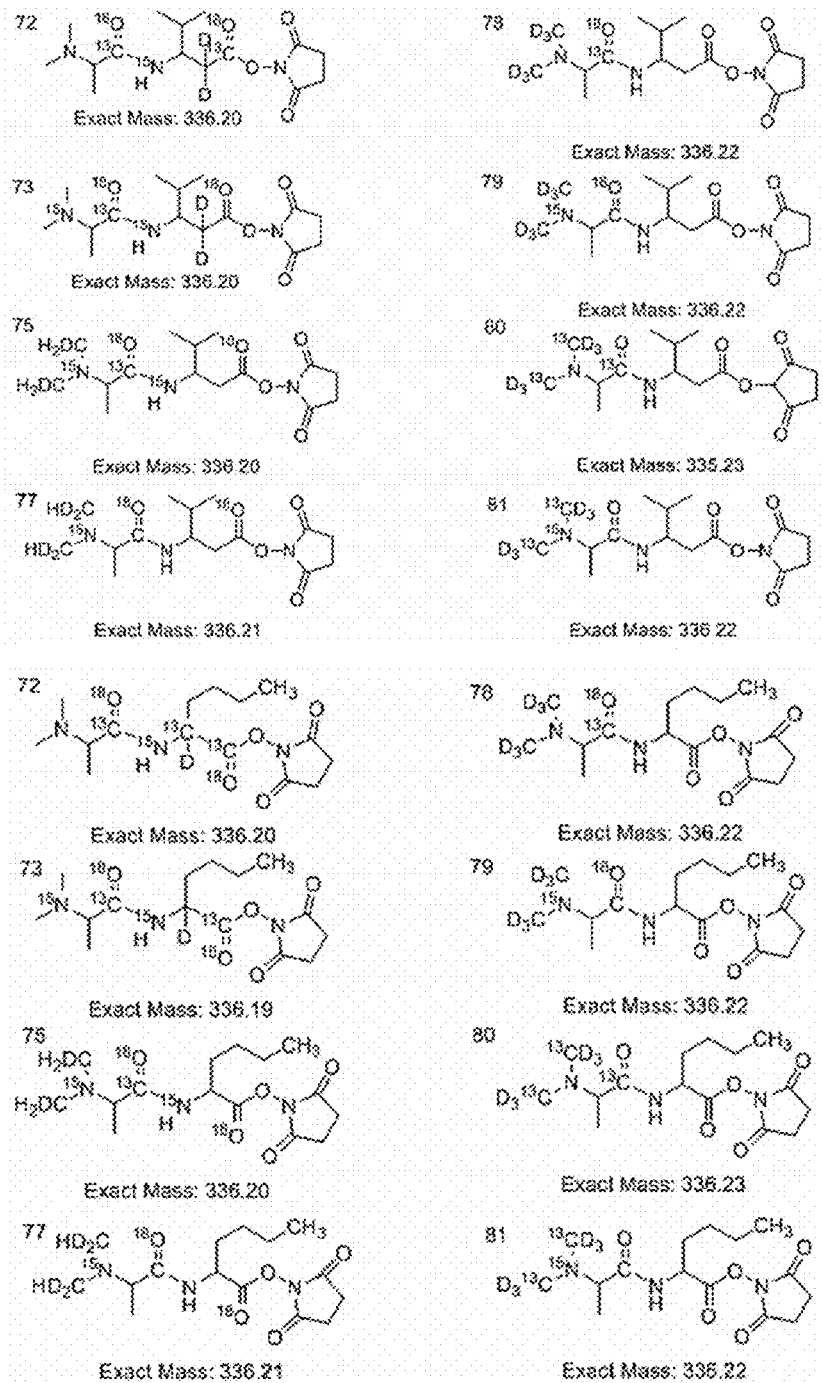
FIG. 26 shows isobaric dimethylated alanine-β leucine and dimethylated alanine-norleucine tagging reagents.
Figure 27:
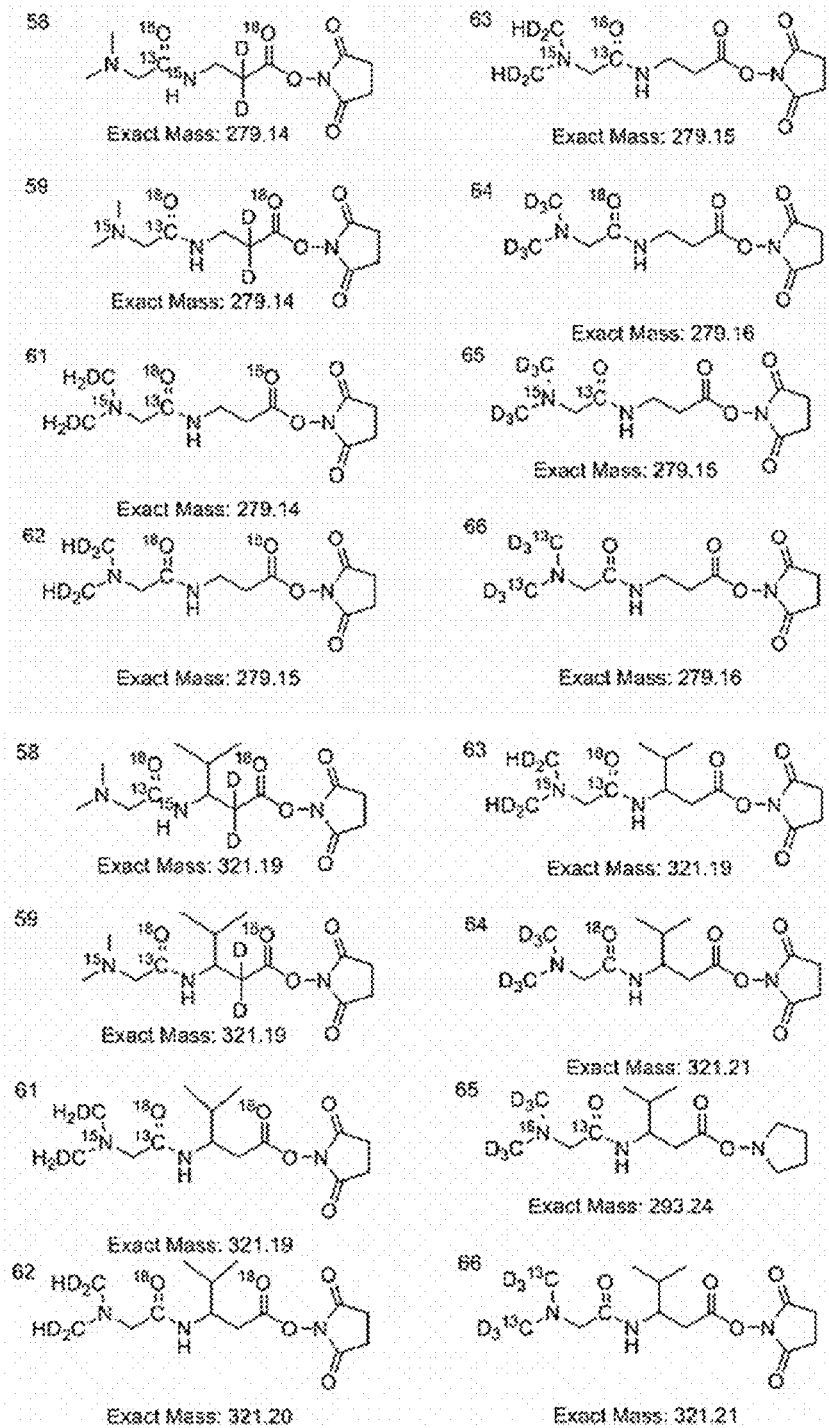
FIG. 27 shows isobaric dimethylated glycine-β alanine and dimethylated glycine-β leucine tagging reagents.
Figure 28:
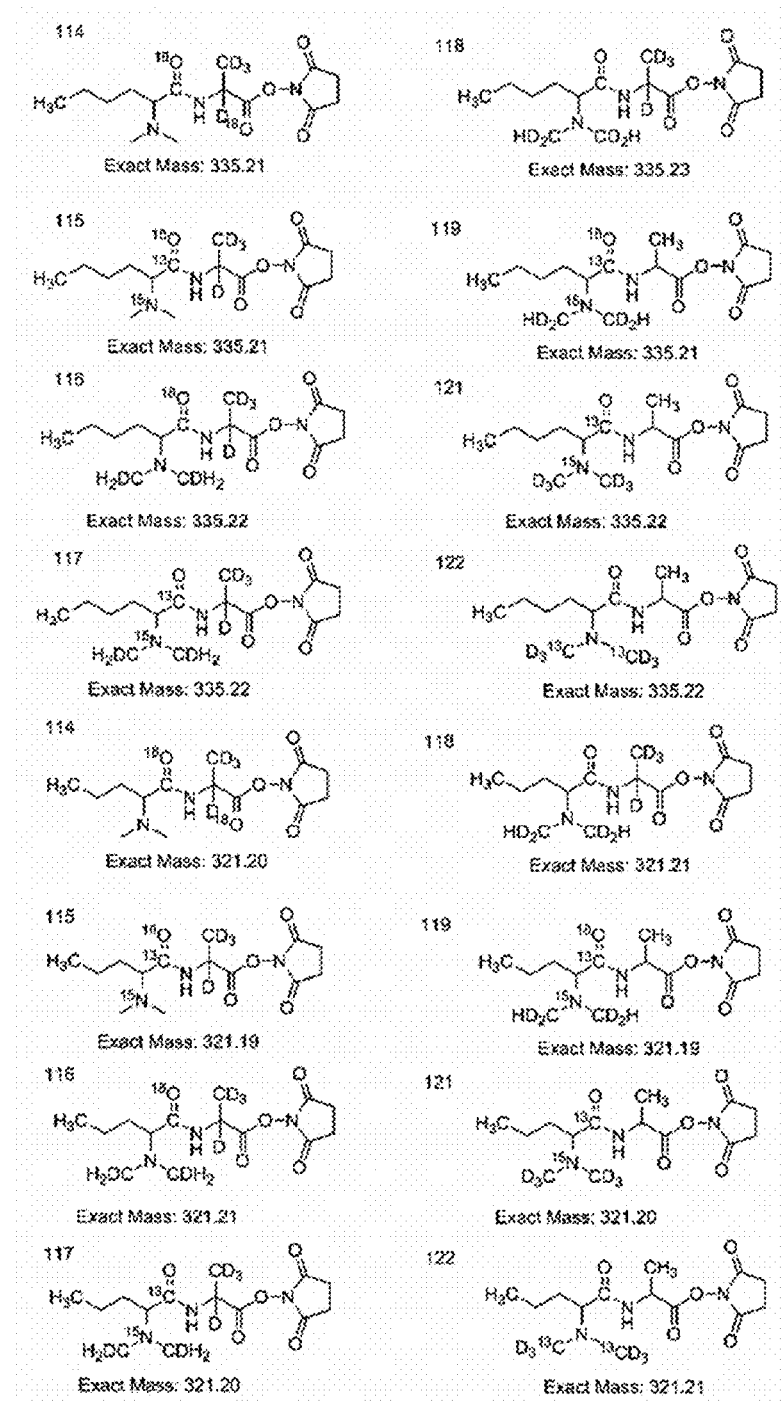
FIG. 28 shows isobaric dimethylated norleucine-alanine and dimethylated norvaline-alanine tagging reagents.
Figure 29:
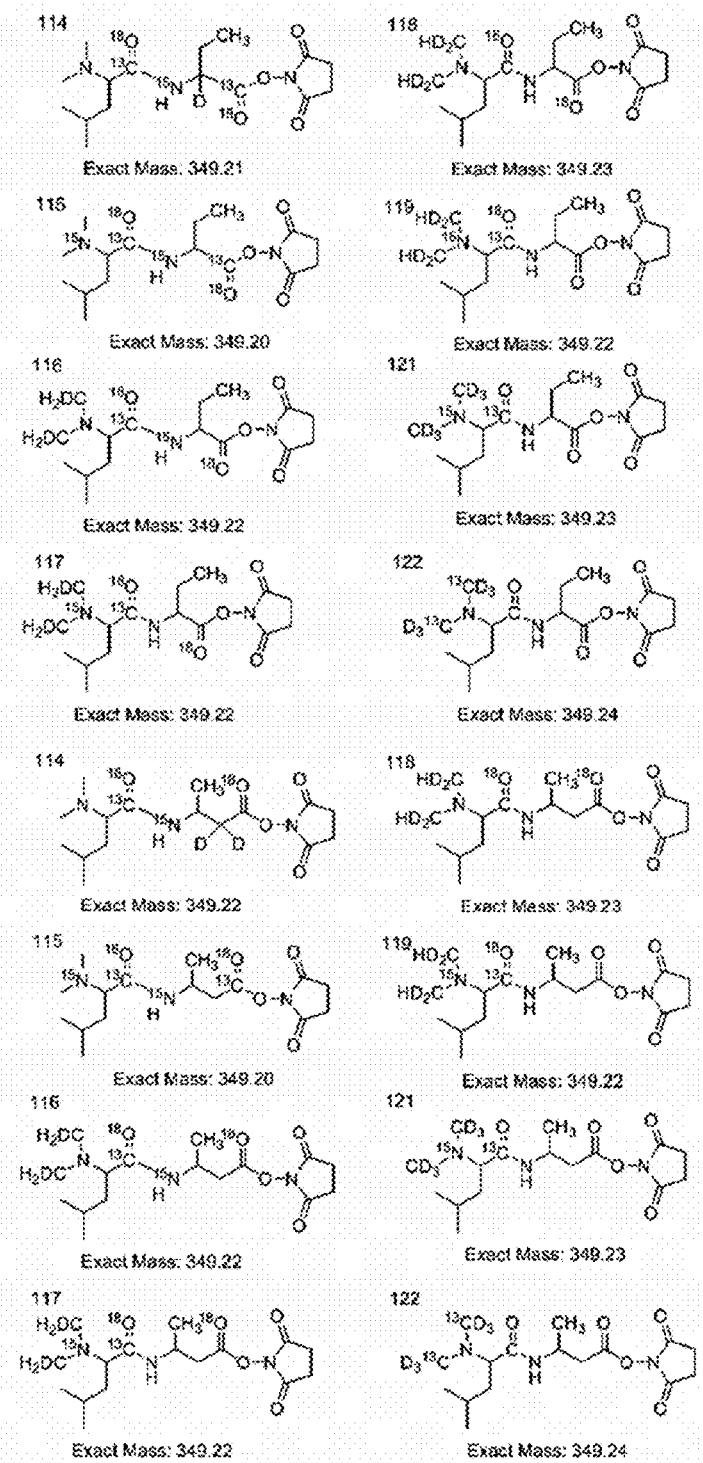
FIG. 29 shows isobaric dimethylated leucine-2-aminobutylric acid and dimethylated leucine-3-aminobutylric acid tagging reagents.
Figure 30:
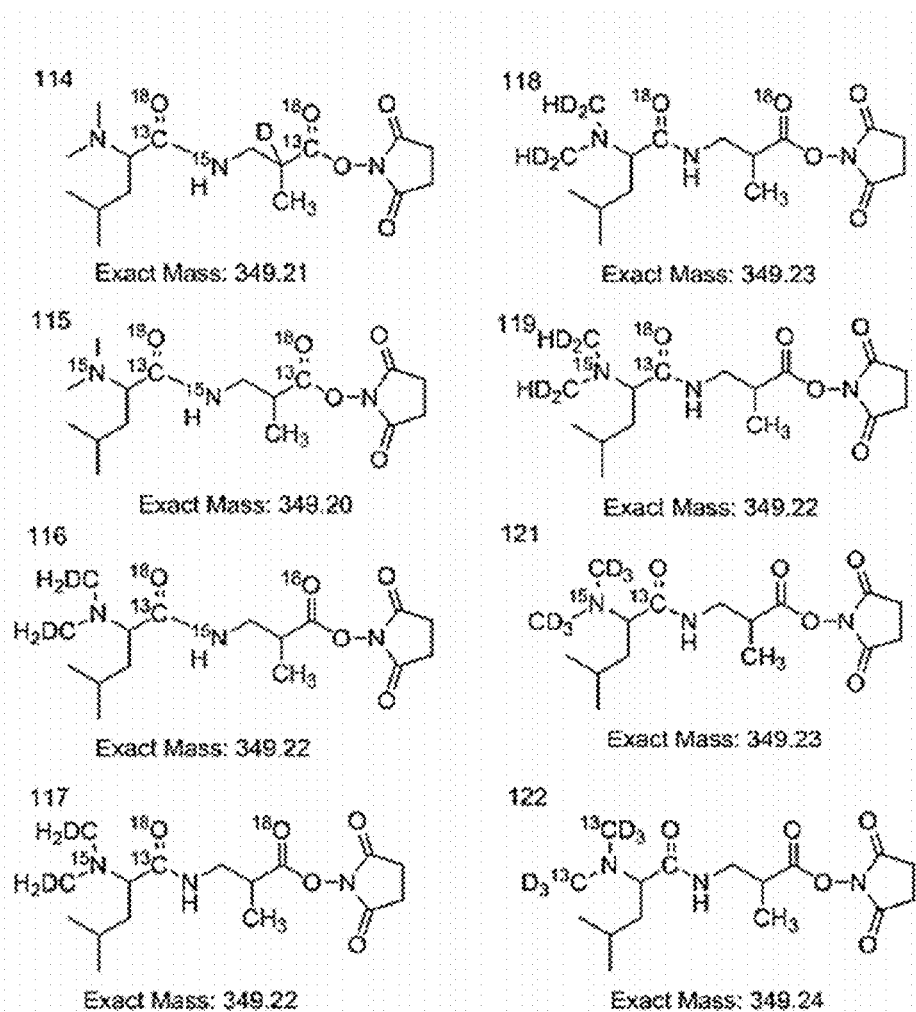
FIG. 30 shows isobaric dimethylated leucine-3-aminobutylric acid tagging reagents.

FIG. 25 shows exemplary tagging reagents which contain non-standard or synthetic amino acids, such as β alanine, β leucine, norleucine, norvaline, 2-aminobutylric acid, 3-aminoisobutylric acid, and 3-aminobutylric acid. Isotopic labeling of atoms in 8-plex tagging reagents utilizing non-standard or synthetic amino acids, such as shown in FIGS. 26-30, would be similar to tagging reagents utilizing natural amino acids.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional peptides, chemically modified peptides, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicants invention, including compounds for which an enabling disclosure is provided in the references cited herein, are not intended to be included in the composition of matter claims herein.

The invention claimed is:

1. A method of analyzing a target molecule having an amine group, said method comprising the steps of:
    a) providing the target molecule;
    b) labeling the target molecule with a tagging reagent, wherein said tagging reagent comprises a N,N-dimethylated based amino acid reporter group, an amine reactive group, and an amino acid based balancing group located between the reporter group and amine reactive group, wherein one or more atoms in the reporter group, balancing group, or both, are isotopically heavy versions of the atom, said tagging reagent having the formula of:

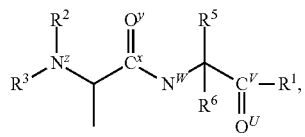

(formula 8)

wherein
$R^1$ is an amine reactive group;
$R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$;
$R^5$ is a hydrogen; deuterium; an isopropyl group optionally containing one or more deuterium atoms and one or more $^{13}C$ atoms; and a butyl group optionally containing one or more deuterium atoms and one or more $^{13}C$ atoms;
$R^6$ is hydrogen or deuterium;
$C^V$ and $C^x$, independently of one another, are $^{12}C$ or $^{13}C$,
$O^U$ and $O^y$, independently of one another, are $^{16}O$ or $^{18}O$; and
$N^z$ and $N^W$, independently of one another, are $^{14}N$ or $^{15}N$, wherein at least one of $R^2$ or $R^3$ contains a deuterium atom, $N^z$ is $^{15}N$, or $N^W$ is $^{15}N$, and at least one of $O^U$ or $O^y$ is $^{18}O$,
    c) fragmenting the labeled target molecule to generate an immonium ion from the labeled molecule; and
    d) detecting and analyzing fragments of the labeled target molecule.

2. The method of claim 1 further comprising identifying one or more fragments of the labeled target molecule using mass spectrometry.

3. The method of claim 1 further comprising quantifying amounts of said one or more fragments of the labeled target molecule.

4. The method of claim 1 wherein $R^5$ is selected from the group consisting of:

a) an isopropyl group containing one or more deuterium atoms and one or more $^{13}C$ atoms; and
    b) a butyl group containing one or more deuterium atoms and one or more $^{13}C$ atoms.

5. The method of claim 1 wherein said target molecule is a peptide, metabolite or neurotransmitter.

6. The method of claim 5 where labeling the peptide comprises the step of reacting the amine reactive group of the tagging reagent with the N-terminus of the peptide or with an ε-amino group within peptide.

7. The method of claim 1 comprising the steps of:
    e) labeling target molecules within at least one additional sample with at least one additional tagging reagent, thereby generating additional labeled target molecules, wherein each of the at least one additional tagging reagent has the formula of:

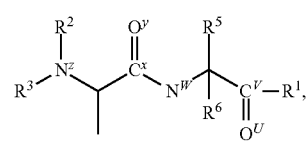

(formula 8)

wherein
$R^1$ is an amine reactive group;
$R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$;
$R^5$ is a; hydrogen; deuterium; an isopropyl group optionally containing one or more deuterium atoms and one or more $^{13}C$ atoms; and a butyl group optionally containing one or more deuterium atoms and one or more $^{13}C$ atoms;
$R^6$ is hydrogen or deuterium;
$C^V$ and $C^x$, independently of one another, are $^{12}C$ or $^{13}C$,
$O^U$ and $O^y$, independently of one another, are $^{16}O$ or $^{18}O$; and
$N^z$ and $N^W$, independently of one another, are $^{14}N$ or $^{15}N$, wherein at least one of $R^2$ or $R^3$ contains a deuterium atom, $N^z$ is $^{15}N$, or $N^W$ is $^{15}N$;
    f) combining the labeled target molecules of steps b) and e);
    g) fragmenting the combined labeled target molecules, wherein the fragmenting step comprises generating an immonium ion from the labeled target molecules; and
    h) analyzing the fragments of the labeled molecules using mass spectrometry,
    wherein each additional tagging reagent has the same chemical structure as the tagging reagent in step b) but contains one or more different isotopically labeled atoms such that the reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same.

8. The method of claim 7 wherein the balancing group of each tagging reagent has the formula:

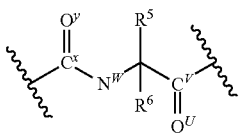

(formula 11)

wherein $R^5$ is selected from the group consisting of an isopropyl group containing one or more deuterium atoms and one or more $^{13}C$ atoms; and a butyl group containing one or more deuterium atoms and one or more $^{13}C$ atoms;

$R^6$ is hydrogen or deuterium;

$C^V$ and $C^x$, independently of one another, are $^{12}C$ or $^{13}C$, $O^U$ and $O^y$, independently of one another, are $^{16}O$ or $^{18}O$, wherein at least one of $O^U$ or $O^y$ is $^{18}O$;

$N^W$ is $^{14}N$ or $^{15}N$.

9. The method of claim 8 wherein the reporter group of each tagging reagent has the formula:

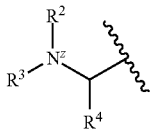

(formula 12)

wherein $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$;

$R^4$ is a methyl group; and $N^z$ is $^{14}N$ or $^{15}N$, wherein at least one of $R^2$ or $R^3$ contains a deuterium atom, $N^z$ is $^{15}N$, or $N^W$ is $^{15}N$.

10. The method of claim 7 further comprising quantifying amounts of said one or more fragments of the labeled target molecules.

11. The method of claim 7 comprising labeling target molecules within at least three additional samples with at least three additional tagging reagents.

12. The method of claim 7 comprising labeling target molecules within at least seven additional samples with at least seven additional tagging reagents.

13. The method of claim 7 comprising labeling target molecules within at least fifteen additional samples with at least fifteen additional tagging reagents.

14. The method of claim 7 wherein the fragmenting step comprises generating an immonium ion from the labeled target molecules, wherein the generated immonium ions from each additional tagging reagent and the first tagging reagent have a mass that differ from one another by two or more Daltons.

15. The method of claim 6 further comprising the step of generating the tagging reagent which comprises coupling a first amino acid with a dimethylated amino acid, wherein the first amino acid, the dimethylated amino acid, or both, are isotopically labeled.

* * * * *